US011202707B2

(12) United States Patent
Shaolian et al.

(10) Patent No.: US 11,202,707 B2
(45) Date of Patent: *Dec. 21, 2021

(54) ADJUSTABLE IMPLANT SYSTEM

(71) Applicant: NuVasive Specialized Orthopedics Inc., San Diego, CA (US)

(72) Inventors: Samuel Shaolian, Newport Beach, CA (US); Scott Pool, Laguna Hills, CA (US); Ross Tsukashima, San Diego, CA (US); Daniel Anderson, Brea, CA (US)

(73) Assignee: NUVASIVE SPECIALIZED ORTHOPEDICS, INC., San Diego, CA (US)

(*) Notice: Subject to any disclaimer, the term of this patent is extended or adjusted under 35 U.S.C. 154(b) by 268 days.

This patent is subject to a terminal disclaimer.

(21) Appl. No.: 16/103,710

(22) Filed: Aug. 14, 2018

(65) Prior Publication Data
US 2019/0000620 A1 Jan. 3, 2019

Related U.S. Application Data

(63) Continuation of application No. 14/885,749, filed on Oct. 16, 2015, now Pat. No. 10,076,413, which is a (Continued)

(51) Int. Cl.
*A61F 2/24* (2006.01)

(52) U.S. Cl.
CPC .......... *A61F 2/2442* (2013.01); *A61F 2/2448* (2013.01); *A61F 2/2445* (2013.01); (Continued)

(58) Field of Classification Search
CPC .... A61F 2/2442; A61F 2/2445; A61F 2/2448; A61F 2/24
See application file for complete search history.

(56) References Cited

U.S. PATENT DOCUMENTS 1,599,538 A 9/1926 Ludger
3,111,945 A 11/1963 Von
(Continued)

FOREIGN PATENT DOCUMENTS

WO WO8604498 8/1986
WO WO0158390 11/1998
(Continued)

OTHER PUBLICATIONS

US 9,161,784 B2, 10/2015, Buttermann (withdrawn)
(Continued)

*Primary Examiner* — Seema Mathew
(74) *Attorney, Agent, or Firm* — Hoffman Warnick LLC

(57) ABSTRACT

Systems and methods treat a heart valve using a magnetically adjustable annuloplasty ring attached to or near a cardiac valve annulus. A changing magnetic field may be used to selectively increase or decrease a circumference of, or otherwise modify the shape of, the implanted annuloplasty ring. The adjustable annuloplasty ring includes a tubular body member, one or more adjustable members, and an internal magnet within the tubular body member. The tubular body member and the one or more adjustable members form a ring shape. The internal magnet is configured to rotate in response to a rotating external magnetic field. The internal magnet is coupled to the one or more adjustable members to change a dimension of the ring shape as the internal magnet rotates. A system for treating a heart valve may include an external adjustment device having one or more external magnets to generate the rotating external magnetic field.

19 Claims, 38 Drawing Sheets

Related U.S. Application Data continuation of application No. 13/625,725, filed on Sep. 24, 2012, now Pat. No. 9,198,755, which is a continuation of application No. 12/411,107, filed on Mar. 25, 2009, now abandoned.

(60) Provisional application No. 61/039,349, filed on Mar. 25, 2008.

(52) U.S. Cl.
CPC . *A61F 2210/009* (2013.01); *A61F 2250/0001* (2013.01); *A61F 2250/0004* (2013.01)

(56) References Cited

U.S. PATENT DOCUMENTS

| | | |
|---|---|---|
| 3,372,476 A | 3/1968 | Richard et al. |
| 3,377,576 A | 4/1968 | Edwin et al. |
| 3,397,928 A | 8/1968 | Galle |
| 3,512,901 A | 5/1970 | Law |
| 3,527,220 A | 9/1970 | Summers |
| 3,597,781 A | 8/1971 | Eibes et al. |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,866,510 A | 2/1975 | Eibes et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,286,584 A | 9/1981 | Sampson et al. |
| 4,300,223 A | 11/1981 | Maire |
| 4,357,946 A | 11/1982 | Dutcher et al. |
| 4,386,603 A | 6/1983 | Mayfield |
| 4,395,259 A | 7/1983 | Prestele et al. |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,339 A | 6/1986 | Kuzmak et al. |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,696,288 A | 9/1987 | Kuzmak et al. |
| 4,700,091 A | 10/1987 | Wuthrich |
| 4,747,832 A | 5/1988 | Buffet |
| 4,760,837 A | 8/1988 | Petit |
| 4,854,304 A | 8/1989 | Zielke |
| 4,872,515 A | 10/1989 | Lundell |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 4,978,323 A | 12/1990 | Freedman |
| 4,998,013 A | 3/1991 | Epstein et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,053,047 A | 10/1991 | Yoon |
| 5,064,004 A | 11/1991 | Lundell |
| 5,074,868 A | 12/1991 | Kuzmak |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,152,770 A | 10/1992 | Bengmark et al. |
| 5,156,605 A | 10/1992 | Pursley et al. |
| 5,176,618 A | 1/1993 | Freedman |
| 5,180,380 A | 1/1993 | Pursley et al. |
| 5,222,976 A | 6/1993 | Yoon |
| 5,226,429 A | 7/1993 | Kuzmak |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,360,407 A | 11/1994 | Leonard et al. |
| 5,364,396 A | 11/1994 | Robinson et al. |
| 5,381,943 A | 1/1995 | Allen et al. |
| 5,399,168 A | 3/1995 | Wadsworth, Jr. et al. |
| 5,403,322 A | 4/1995 | Herzenberg et al. |
| 5,429,638 A | 7/1995 | Muschler et al. |
| 5,433,721 A | 7/1995 | Hooven et al. |
| 5,437,266 A | 8/1995 | McPherson et al. |
| 5,449,368 A | 9/1995 | Kuzmak |
| 5,466,261 A | 11/1995 | Richelsoph |
| 5,468,030 A | 11/1995 | Walling |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Eyck et al. |
| 5,549,610 A | 8/1996 | Russell et al. |
| 5,573,496 A | 11/1996 | McPherson et al. |
| 5,575,790 A | 11/1996 | Chen et al. |
| 5,582,616 A | 12/1996 | Bolduc et al. |
| 5,601,224 A | 2/1997 | Bishop et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,628,888 A | 5/1997 | Bakhir et al. |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,676,162 A | 10/1997 | Larson, Jr. et al. |
| 5,693,091 A | 12/1997 | Larson, Jr. et al. |
| 5,700,263 A | 12/1997 | Schendel |
| 5,702,430 A | 12/1997 | Larson, Jr. et al. |
| 5,704,893 A | 1/1998 | Timm |
| 5,704,938 A | 1/1998 | Staehlin et al. |
| 5,704,939 A | 1/1998 | Justin |
| 5,720,746 A | 2/1998 | Soubeiran |
| 5,722,429 A | 3/1998 | Larson, Jr. et al. |
| 5,722,930 A | 3/1998 | Larson, Jr. et al. |
| 5,743,910 A | 4/1998 | Bays et al. |
| 5,758,666 A | 6/1998 | Larson, Jr. et al. |
| 5,762,599 A | 6/1998 | Sohn |
| 5,766,208 A | 6/1998 | McEwan |
| 5,771,903 A | 6/1998 | Jakobsson |
| 5,800,434 A | 9/1998 | Campbell, Jr. |
| 5,810,815 A | 9/1998 | Morales |
| 5,824,008 A | 10/1998 | Bolduc et al. |
| 5,827,286 A | 10/1998 | Incavo et al. |
| 5,829,662 A | 11/1998 | Allen et al. |
| 5,830,221 A | 11/1998 | Stein et al. |
| 5,843,129 A | 12/1998 | Larson, Jr. et al. |
| 5,874,796 A | 2/1999 | Petersen |
| 5,879,375 A | 3/1999 | Larson, Jr. et al. |

(56) References Cited

U.S. PATENT DOCUMENTS

| | | |
|---|---|---|
| 5,902,304 A | 5/1999 | Walker et al. |
| 5,935,127 A | 8/1999 | Border |
| 5,938,669 A | 8/1999 | Klaiber et al. |
| 5,945,762 A | 8/1999 | Chen et al. |
| 5,954,915 A | 9/1999 | Voorhees et al. |
| 5,961,553 A | 10/1999 | Coty et al. |
| 5,964,763 A | 10/1999 | Incavo et al. |
| 5,976,138 A | 11/1999 | Baumgart et al. |
| 5,979,456 A | 11/1999 | Magovern |
| 5,985,110 A | 11/1999 | Bakhir et al. |
| 5,997,490 A | 12/1999 | McLeod et al. |
| 6,009,837 A | 1/2000 | McClasky |
| 6,022,349 A | 2/2000 | McLeod et al. |
| 6,033,412 A | 3/2000 | Losken et al. |
| 6,034,296 A | 3/2000 | Elvin et al. |
| 6,067,991 A | 5/2000 | Forsell |
| 6,074,341 A | 6/2000 | Anderson et al. |
| 6,074,882 A | 6/2000 | Eckardt |
| 6,092,531 A | 7/2000 | Chen et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,210,347 B1 | 4/2001 | Forsell |
| 6,217,847 B1 | 4/2001 | Contag et al. |
| 6,221,074 B1 | 4/2001 | Cole et al. |
| 6,234,299 B1 | 5/2001 | Voorhees et al. |
| 6,234,956 B1 | 5/2001 | He et al. |
| 6,241,730 B1 | 6/2001 | Alby |
| 6,245,075 B1 | 6/2001 | Betz et al. |
| 6,283,156 B1 | 9/2001 | Motley |
| 6,296,643 B1 | 10/2001 | Hopf et al. |
| 6,296,656 B1 | 10/2001 | Bolduc et al. |
| 6,299,613 B1 | 10/2001 | Ogilvie et al. |
| 6,315,784 B1 | 11/2001 | Djurovic |
| 6,319,255 B1 | 11/2001 | Grundei et al. |
| 6,321,106 B1 | 11/2001 | Lemelson |
| 6,325,805 B1 | 12/2001 | Ogilvie et al. |
| 6,327,492 B1 | 12/2001 | Lemelson |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,386,083 B1 | 5/2002 | Hwang |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,423,061 B1 | 7/2002 | Bryant |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,508,820 B2 | 1/2003 | Bales |
| 6,510,345 B1 | 1/2003 | Van Bentem |
| 6,511,490 B2 | 1/2003 | Robert |
| 6,527,701 B1 | 3/2003 | Sayet et al. |
| 6,527,702 B2 | 3/2003 | Whalen et al. |
| 6,536,499 B2 | 3/2003 | Voorhees et al. |
| 6,537,196 B1 | 3/2003 | Creighton, IV et al. |
| 6,547,801 B1 | 4/2003 | Dargent et al. |
| 6,554,831 B1 | 4/2003 | Rivard et al. |
| 6,558,400 B2 | 5/2003 | Deem et al. |
| 6,562,051 B1 | 5/2003 | Bolduc et al. |
| 6,565,573 B1 | 5/2003 | Ferrante et al. |
| 6,565,576 B1 | 5/2003 | Stauch et al. |
| 6,573,706 B2 | 6/2003 | Mendes et al. |
| 6,582,313 B2 | 6/2003 | Perrow |
| 6,583,630 B2 | 6/2003 | Mendes et al. |
| 6,587,719 B1 | 7/2003 | Barrett et al. |
| 6,595,912 B2 | 7/2003 | Lau et al. |
| 6,602,184 B2 | 8/2003 | Lau et al. |
| 6,604,529 B2 | 8/2003 | Kim |
| 6,607,363 B1 | 8/2003 | Domroese |
| 6,609,025 B2 | 8/2003 | Barrett et al. |
| 6,612,978 B2 | 9/2003 | Lau et al. |
| 6,612,979 B2 | 9/2003 | Lau et al. |
| 6,616,669 B2 | 9/2003 | Ogilvie et al. |
| 6,621,956 B2 | 9/2003 | Greenaway et al. |
| 6,626,899 B2 | 9/2003 | Houser et al. |
| 6,626,917 B1 | 9/2003 | Craig |
| 6,627,206 B2 | 9/2003 | Lloyd |
| 6,649,143 B1 | 11/2003 | Contag et al. |
| 6,656,135 B2 | 12/2003 | Zogbi et al. |
| 6,656,194 B1 | 12/2003 | Gannoe et al. |
| 6,657,351 B2 | 12/2003 | Chen et al. |
| 6,667,725 B1 | 12/2003 | Simons et al. |
| 6,669,687 B1 | 12/2003 | Saadat |
| 6,673,079 B1 | 1/2004 | Kane |
| 6,676,674 B1 | 1/2004 | Dudai |
| 6,682,474 B2 | 1/2004 | Lau et al. |
| 6,689,046 B2 | 2/2004 | Sayet et al. |
| 6,702,732 B1 | 3/2004 | Lau et al. |
| 6,702,816 B2 | 3/2004 | Buhler |
| 6,706,042 B2 | 3/2004 | Taylor |
| 6,709,293 B2 | 3/2004 | Mori et al. |
| 6,709,385 B2 | 3/2004 | Forsell |
| 6,730,087 B1 | 5/2004 | Butsch |
| 6,749,556 B2 | 6/2004 | Banik |
| 6,752,754 B1 | 6/2004 | Feng et al. |
| 6,761,503 B2 | 7/2004 | Breese |
| 6,765,330 B2 | 7/2004 | Baur |
| 6,769,499 B2 | 8/2004 | Cargill et al. |
| 6,773,437 B2 | 8/2004 | Ogilvie et al. |
| 6,774,624 B2 | 8/2004 | Anderson et al. |
| 6,789,442 B2 | 9/2004 | Forch |
| 6,796,984 B2 | 9/2004 | Soubeiran |
| 6,802,844 B2 | 10/2004 | Ferree |
| 6,802,847 B1 | 10/2004 | Carson et al. |
| 6,809,434 B1 | 10/2004 | Duncan et al. |
| 6,835,183 B2 | 12/2004 | Lennox et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,864,647 B2 | 3/2005 | Duncan et al. |
| 6,884,248 B2 | 4/2005 | Bolduc et al. |
| 6,890,515 B2 | 5/2005 | Contag et al. |
| 6,908,605 B2 | 6/2005 | Contag et al. |
| 6,915,165 B2 | 7/2005 | Forsell |
| 6,916,462 B2 | 7/2005 | Contag et al. |
| 6,918,838 B2 | 7/2005 | Schwarzler et al. |
| 6,918,910 B2 | 7/2005 | Smith et al. |
| 6,921,360 B2 | 7/2005 | Banik |
| 6,921,400 B2 | 7/2005 | Sohngen |
| 6,923,951 B2 | 8/2005 | Contag et al. |
| 6,926,719 B2 | 8/2005 | Sohngen et al. |
| 6,939,533 B2 | 9/2005 | Contag et al. |
| 6,953,429 B2 | 10/2005 | Forsell |
| 6,961,553 B2 | 11/2005 | Zhao et al. |

(56) References Cited

U.S. PATENT DOCUMENTS

| | | | |
|---|---|---|---|
| 6,971,143 | B2 | 12/2005 | Domroese |
| 6,980,921 | B2 | 12/2005 | Anderson et al. |
| 6,997,952 | B2 | 2/2006 | Furukawa et al. |
| 7,001,327 | B2 | 2/2006 | Whalen et al. |
| 7,001,346 | B2 | 2/2006 | White |
| 7,008,425 | B2 | 3/2006 | Phillips |
| 7,011,621 | B2 | 3/2006 | Sayet et al. |
| 7,011,658 | B2 | 3/2006 | Young |
| 7,011,682 | B2 | 3/2006 | Lashinski et al. |
| 7,018,380 | B2 | 3/2006 | Cole |
| 7,029,475 | B2 | 4/2006 | Panjabi |
| 7,041,105 | B2 | 5/2006 | Michelson |
| 7,060,075 | B2 | 6/2006 | Govari et al. |
| 7,060,080 | B2 | 6/2006 | Bachmann |
| 7,063,706 | B2 | 6/2006 | Wittenstein |
| 7,077,802 | B2 | 7/2006 | Lau et al. |
| 7,081,086 | B2 | 7/2006 | Lau et al. |
| 7,083,629 | B2 | 8/2006 | Weller et al. |
| 7,096,148 | B2 | 8/2006 | Anderson et al. |
| 7,097,611 | B2 | 8/2006 | Lau et al. |
| 7,105,029 | B2 | 9/2006 | Doubler et al. |
| 7,105,968 | B2 | 9/2006 | Nissen |
| 7,114,501 | B2 | 10/2006 | Johnson et al. |
| 7,115,129 | B2 | 10/2006 | Heggeness |
| 7,115,130 | B2 | 10/2006 | Michelson |
| 7,124,493 | B2 | 10/2006 | Lau et al. |
| 7,128,707 | B2 | 10/2006 | Banik |
| 7,135,022 | B2 | 11/2006 | Kosashvili et al. |
| 7,160,312 | B2 | 1/2007 | Saadat |
| 7,163,538 | B2 | 1/2007 | Altarac et al. |
| 7,172,607 | B2 | 2/2007 | Hofle et al. |
| 7,175,589 | B2 | 2/2007 | Deem et al. |
| 7,175,660 | B2 | 2/2007 | Cartledge et al. |
| 7,186,262 | B2 | 3/2007 | Saadat |
| 7,188,627 | B2 | 3/2007 | Nelson et al. |
| 7,189,005 | B2 | 3/2007 | Ward |
| 7,189,202 | B2 | 3/2007 | Lau et al. |
| 7,189,251 | B2 | 3/2007 | Kay |
| 7,191,007 | B2 | 3/2007 | Desai et al. |
| 7,194,297 | B2 | 3/2007 | Talpade et al. |
| 7,195,608 | B2 | 3/2007 | Burnett |
| 7,198,774 | B2 | 4/2007 | Contag et al. |
| 7,211,094 | B2 | 5/2007 | Gannoe et al. |
| 7,216,648 | B2 | 5/2007 | Nelson et al. |
| 7,217,284 | B2 | 5/2007 | Houser et al. |
| 7,218,232 | B2 | 5/2007 | DiSilvestro et al. |
| 7,232,449 | B2 | 6/2007 | Sharkawy et al. |
| 7,234,468 | B2 | 6/2007 | Johnson et al. |
| 7,234,544 | B2 | 6/2007 | Kent |
| 7,238,152 | B2 | 7/2007 | Lau et al. |
| 7,238,191 | B2 | 7/2007 | Bachmann |
| 7,241,300 | B2 | 7/2007 | Sharkawy et al. |
| 7,243,719 | B2 | 7/2007 | Baron et al. |
| 7,255,682 | B1 | 8/2007 | Bartol, Jr. et al. |
| 7,255,714 | B2 | 8/2007 | Malek |
| 7,255,851 | B2 | 8/2007 | Contag et al. |
| 7,276,022 | B2 | 10/2007 | Lau et al. |
| 7,282,023 | B2 | 10/2007 | Frering |
| 7,285,087 | B2 | 10/2007 | Moaddeb et al. |
| 7,288,064 | B2 | 10/2007 | Boustani et al. |
| 7,288,099 | B2 | 10/2007 | Deem et al. |
| 7,288,101 | B2 | 10/2007 | Deem et al. |
| 7,296,577 | B2 | 11/2007 | Lashinski et al. |
| 7,297,150 | B2 | 11/2007 | Cartledge et al. |
| 7,299,091 | B2 | 11/2007 | Barrett et al. |
| 7,302,858 | B2 | 12/2007 | Walsh et al. |
| 7,306,614 | B2 | 12/2007 | Weller et al. |
| 7,311,690 | B2 | 12/2007 | Burnett |
| 7,314,372 | B2 | 1/2008 | Belfor et al. |
| 7,314,443 | B2 | 1/2008 | Jordan et al. |
| 7,320,706 | B2 | 1/2008 | Al-Najjar |
| 7,331,995 | B2 | 2/2008 | Eisermann et al. |
| 7,333,013 | B2 | 2/2008 | Berger |
| 7,338,433 | B2 | 3/2008 | Coe |
| 7,340,306 | B2 | 3/2008 | Barrett et al. |
| 7,351,198 | B2 | 4/2008 | Byrum et al. |
| 7,351,240 | B2 | 4/2008 | Hassler, Jr. et al. |
| 7,353,747 | B2 | 4/2008 | Swayze et al. |
| 7,357,037 | B2 | 4/2008 | Hnat et al. |
| 7,357,635 | B2 | 4/2008 | Belfor et al. |
| 7,360,542 | B2 | 4/2008 | Nelson et al. |
| 7,361,192 | B2 | 4/2008 | Doty |
| 7,364,542 | B2 | 4/2008 | Jambor et al. |
| 7,364,589 | B2 | 4/2008 | Eisermann |
| 7,367,340 | B2 | 5/2008 | Nelson et al. |
| 7,367,937 | B2 | 5/2008 | Jambor et al. |
| 7,367,938 | B2 | 5/2008 | Forsell |
| 7,371,244 | B2 | 5/2008 | Chatlynne et al. |
| 7,374,557 | B2 | 5/2008 | Conlon et al. |
| 7,390,007 | B2 | 6/2008 | Helms et al. |
| 7,390,294 | B2 | 6/2008 | Hassler, Jr. |
| 7,400,926 | B2 | 7/2008 | Forsell |
| 7,402,134 | B2 | 7/2008 | Moaddeb et al. |
| 7,402,176 | B2 | 7/2008 | Malek |
| 7,410,461 | B2 | 8/2008 | Lau et al. |
| 7,416,528 | B2 | 8/2008 | Crawford et al. |
| 7,422,566 | B2 | 9/2008 | Miethke |
| 7,429,259 | B2 | 9/2008 | Cadeddu et al. |
| 7,431,692 | B2 | 10/2008 | Zollinger et al. |
| 7,441,559 | B2 | 10/2008 | Nelson et al. |
| 7,442,196 | B2 | 10/2008 | Fisher et al. |
| 7,445,010 | B2 | 11/2008 | Kugler et al. |
| 7,455,690 | B2 | 11/2008 | Cartledge et al. |
| 7,458,981 | B2 | 12/2008 | Fielding et al. |
| 7,468,060 | B2 | 12/2008 | Utley et al. |
| 7,476,195 | B2 | 1/2009 | Sayet et al. |
| 7,476,238 | B2 | 1/2009 | Panjabi |
| 7,481,224 | B2 | 1/2009 | Nelson et al. |
| 7,481,763 | B2 | 1/2009 | Hassler, Jr. et al. |
| 7,481,841 | B2 | 1/2009 | Hazebrouck et al. |
| 7,485,143 | B2 | 2/2009 | Webler |
| 7,485,149 | B1 | 2/2009 | White |
| 7,489,495 | B2 | 2/2009 | Stevenson |
| 7,494,459 | B2 | 2/2009 | Anstadt et al. |
| 7,500,484 | B2 | 3/2009 | Nelson et al. |
| 7,503,922 | B2 | 3/2009 | Deem et al. |
| 7,503,934 | B2 | 3/2009 | Eisermann et al. |
| 7,507,252 | B2 | 3/2009 | Lashinski et al. |
| 7,510,559 | B2 | 3/2009 | Deem et al. |
| 7,530,981 | B2 | 5/2009 | Kutsenko |
| 7,531,002 | B2 | 5/2009 | Sutton et al. |
| 7,547,291 | B2 | 6/2009 | Lennox et al. |
| 7,553,298 | B2 | 6/2009 | Hunt et al. |
| 7,559,951 | B2 | 7/2009 | DiSilvestro et al. |
| 7,561,916 | B2 | 7/2009 | Hunt et al. |
| 7,562,660 | B2 | 7/2009 | Saadat |
| 7,566,297 | B2 | 7/2009 | Banik |
| 7,569,057 | B2 | 8/2009 | Liu et al. |
| 7,578,821 | B2 | 8/2009 | Fisher et al. |
| 7,584,788 | B2 | 9/2009 | Baron et al. |
| 7,594,887 | B2 | 9/2009 | Moaddeb et al. |
| 7,601,156 | B2 | 10/2009 | Robinson |
| 7,601,162 | B2 | 10/2009 | Hassler, Jr. et al. |
| 7,601,171 | B2 | 10/2009 | Ainsworth et al. |
| 7,611,526 | B2 | 11/2009 | Carl et al. |
| 7,615,001 | B2 | 11/2009 | Jambor et al. |
| 7,615,068 | B2 | 11/2009 | Timm et al. |
| 7,618,435 | B2 | 11/2009 | Opolski |
| 7,621,886 | B2 | 11/2009 | Burnett |
| 7,635,379 | B2 | 12/2009 | Callahan et al. |
| 7,651,483 | B2 | 1/2010 | Byrum et al. |
| 7,658,753 | B2 | 2/2010 | Carl et al. |
| 7,666,132 | B2 | 2/2010 | Forsell |
| 7,666,184 | B2 | 2/2010 | Stauch |
| 7,666,210 | B2 | 2/2010 | Franck et al. |
| 7,678,136 | B2 | 3/2010 | Doubler et al. |
| 7,678,139 | B2 | 3/2010 | Garamszegi et al. |
| 7,691,144 | B2 | 4/2010 | Chang et al. |
| 7,695,512 | B2 | 4/2010 | Lashinski et al. |
| 7,704,279 | B2 | 4/2010 | Moskowitz et al. |
| 7,704,282 | B2 | 4/2010 | Disilvestro et al. |
| 7,708,737 | B2 | 5/2010 | Kraft et al. |
| 7,708,762 | B2 | 5/2010 | McCarthy et al. |
| 7,708,765 | B2 | 5/2010 | Carl et al. |

(56) References Cited

U.S. PATENT DOCUMENTS

| | | |
|---|---|---|
| 7,708,779 B2 | 5/2010 | Edie et al. |
| 7,713,287 B2 | 5/2010 | Timm et al. |
| 7,717,959 B2 | 5/2010 | William et al. |
| 7,727,141 B2 | 6/2010 | Hassler, Jr. et al. |
| 7,727,143 B2 | 6/2010 | Birk et al. |
| 7,749,224 B2 | 7/2010 | Cresina et al. |
| 7,753,913 B2 | 7/2010 | Szakelyhidi, Jr. et al. |
| 7,753,915 B1 | 7/2010 | Eksler et al. |
| 7,757,552 B2 | 7/2010 | Bogath et al. |
| 7,762,998 B2 | 7/2010 | Birk et al. |
| 7,763,053 B2 | 7/2010 | Gordon |
| 7,763,080 B2 | 7/2010 | Worth |
| 7,766,815 B2 | 8/2010 | Ortiz |
| 7,775,099 B2 | 8/2010 | Bogath et al. |
| 7,775,215 B2 | 8/2010 | Hassler, Jr. et al. |
| 7,776,061 B2 | 8/2010 | Garner et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,780,590 B2 | 8/2010 | Birk et al. |
| 7,787,958 B2 | 8/2010 | Stevenson |
| 7,789,912 B2 | 9/2010 | Manzi et al. |
| 7,793,583 B2 | 9/2010 | Radinger et al. |
| 7,794,447 B2 | 9/2010 | Dann et al. |
| 7,794,476 B2 | 9/2010 | Wisnewski |
| 7,798,954 B2 | 9/2010 | Birk et al. |
| 7,799,080 B2 | 9/2010 | Doty |
| 7,803,106 B2 | 9/2010 | Whalen et al. |
| 7,803,157 B2 | 9/2010 | Michelson |
| 7,811,275 B2 | 10/2010 | Birk et al. |
| 7,811,298 B2 | 10/2010 | Birk |
| 7,811,328 B2 | 10/2010 | Molz, IV et al. |
| 7,815,643 B2 | 10/2010 | Johnson et al. |
| 7,828,714 B2 | 11/2010 | Feng et al. |
| 7,828,813 B2 | 11/2010 | Mouton |
| 7,833,228 B1 | 11/2010 | Hershberger |
| 7,835,779 B2 | 11/2010 | Anderson et al. |
| 7,837,669 B2 | 11/2010 | Dann et al. |
| 7,837,691 B2 | 11/2010 | Cordes et al. |
| 7,842,036 B2 | 11/2010 | Phillips |
| 7,845,356 B2 | 12/2010 | Paraschac et al. |
| 7,846,188 B2 | 12/2010 | Moskowitz et al. |
| 7,850,660 B2 | 12/2010 | Uth et al. |
| 7,850,735 B2 | 12/2010 | Eisermann et al. |
| 7,854,769 B2 | 12/2010 | Hershberger |
| 7,862,546 B2 | 1/2011 | Conlon et al. |
| 7,862,574 B2 | 1/2011 | Deem et al. |
| 7,862,586 B2 | 1/2011 | Malek |
| 7,867,235 B2 | 1/2011 | Fell et al. |
| 7,871,368 B2 | 1/2011 | Zollinger et al. |
| 7,875,033 B2 | 1/2011 | Richter et al. |
| 7,887,566 B2 | 2/2011 | Hynes |
| 7,901,381 B2 | 3/2011 | Birk et al. |
| 7,901,419 B2 | 3/2011 | Bachmann et al. |
| 7,909,790 B2 | 3/2011 | Burnett |
| 7,909,838 B2 | 3/2011 | Deem et al. |
| 7,909,839 B2 | 3/2011 | Fields |
| 7,909,852 B2 | 3/2011 | Boomer et al. |
| 7,918,844 B2 | 4/2011 | Byrum et al. |
| 7,921,850 B2 | 4/2011 | Nelson et al. |
| 7,922,765 B2 | 4/2011 | Reiley |
| 7,927,354 B2 | 4/2011 | Edidin et al. |
| 7,927,357 B2 | 4/2011 | Sacher et al. |
| 7,931,679 B2 | 4/2011 | Heggeness |
| 7,932,825 B2 | 4/2011 | Berger |
| 7,938,836 B2 | 5/2011 | Ainsworth et al. |
| 7,938,841 B2 | 5/2011 | Sharkawy et al. |
| 7,942,903 B2 | 5/2011 | Moskowitz et al. |
| 7,942,908 B2 | 5/2011 | Sacher et al. |
| 7,947,011 B2 | 5/2011 | Birk et al. |
| 7,951,067 B2 | 5/2011 | Byrum et al. |
| 7,951,180 B2 | 5/2011 | Moskowitz et al. |
| 7,958,895 B2 | 6/2011 | Nelson et al. |
| 7,958,896 B2 | 6/2011 | Nelson et al. |
| 7,959,552 B2 | 6/2011 | Jordan et al. |
| 7,972,315 B2 | 7/2011 | Birk et al. |
| 7,972,346 B2 | 7/2011 | Bachmann et al. |
| 7,972,363 B2 | 7/2011 | Moskowitz et al. |
| 7,976,545 B2 | 7/2011 | Hershberger et al. |
| 7,983,763 B2 | 7/2011 | Stevenson et al. |
| 7,985,256 B2 | 7/2011 | Grotz et al. |
| 7,987,241 B2 | 7/2011 | St Jacques, Jr. et al. |
| 7,988,707 B2 | 8/2011 | Panjabi |
| 7,988,709 B2 | 8/2011 | Clark et al. |
| 7,993,342 B2 | 8/2011 | Malandain et al. |
| 7,993,397 B2 | 8/2011 | Lashinski et al. |
| 7,998,174 B2 | 8/2011 | Malandain et al. |
| 7,998,208 B2 | 8/2011 | Kohm et al. |
| 8,002,801 B2 | 8/2011 | Carl et al. |
| 8,002,809 B2 | 8/2011 | Baynham |
| 8,007,458 B2 | 8/2011 | Lennox et al. |
| 8,007,474 B2 | 8/2011 | Uth et al. |
| 8,007,479 B2 | 8/2011 | Birk et al. |
| 8,011,308 B2 | 9/2011 | Picchio |
| 8,012,162 B2 | 9/2011 | Bachmann |
| 8,016,745 B2 | 9/2011 | Hassler, Jr. et al. |
| 8,016,837 B2 | 9/2011 | Giger et al. |
| 8,016,860 B2 | 9/2011 | Carl et al. |
| 8,026,729 B2 | 9/2011 | Kroh et al. |
| 8,029,477 B2 | 10/2011 | Byrum et al. |
| 8,029,507 B2 | 10/2011 | Green et al. |
| 8,029,567 B2 | 10/2011 | Edidin et al. |
| 8,034,080 B2 | 10/2011 | Malandain et al. |
| 8,037,871 B2 | 10/2011 | McClendon |
| 8,038,680 B2 | 10/2011 | Ainsworth et al. |
| 8,038,698 B2 | 10/2011 | Edidin et al. |
| 8,043,206 B2 | 10/2011 | Birk |
| 8,043,290 B2 | 10/2011 | Harrison et al. |
| 8,043,299 B2 | 10/2011 | Conway |
| 8,043,338 B2 | 10/2011 | Dant |
| 8,043,345 B2 | 10/2011 | Carl et al. |
| 8,048,169 B2 | 11/2011 | Burnett et al. |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,670 B2 | 12/2011 | Deem et al. |
| 8,070,671 B2 | 12/2011 | Deem et al. |
| 8,070,695 B2 | 12/2011 | Gupta et al. |
| 8,070,813 B2 | 12/2011 | Grotz et al. |
| 8,074,654 B2 | 12/2011 | Paraschac et al. |
| 8,075,577 B2 | 12/2011 | Deem et al. |
| 8,079,974 B2 | 12/2011 | Stergiopulos |
| 8,079,989 B2 | 12/2011 | Birk et al. |
| 8,080,022 B2 | 12/2011 | Deem et al. |
| 8,080,025 B2 | 12/2011 | Deem et al. |
| 8,088,166 B2 | 1/2012 | Makower et al. |
| 8,092,459 B2 | 1/2012 | Malandain |
| 8,092,499 B1 | 1/2012 | Roth |
| 8,095,317 B2 | 1/2012 | Ekseth et al. |
| 8,096,302 B2 | 1/2012 | Nelson et al. |
| 8,096,938 B2 | 1/2012 | Forsell |
| 8,096,995 B2 | 1/2012 | Kohm et al. |
| 8,097,018 B2 | 1/2012 | Malandain et al. |
| 8,097,038 B2 | 1/2012 | Malek |
| 8,100,819 B2 | 1/2012 | Banik |
| 8,100,943 B2 | 1/2012 | Malandain et al. |
| 8,100,967 B2 | 1/2012 | Makower et al. |
| 8,105,360 B1 | 1/2012 | Connor |
| 8,105,363 B2 | 1/2012 | Fielding et al. |
| 8,105,364 B2 | 1/2012 | McCarthy et al. |
| 8,109,974 B2 | 2/2012 | Boomer et al. |
| 8,114,158 B2 | 2/2012 | Carl et al. |
| 8,123,765 B2 | 2/2012 | Deem et al. |
| 8,123,805 B2 | 2/2012 | Makower et al. |
| 8,128,628 B2 | 3/2012 | Freid et al. |
| 8,133,280 B2 | 3/2012 | Voellmicke et al. |
| 8,137,349 B2 | 3/2012 | Soubeiran |
| 8,137,366 B2 | 3/2012 | Deem et al. |
| 8,137,367 B2 | 3/2012 | Deem et al. |
| 8,142,454 B2 | 3/2012 | Harrison et al. |
| 8,142,494 B2 | 3/2012 | Rahdert et al. |
| 8,147,517 B2 | 4/2012 | Trieu et al. |
| 8,147,549 B2 | 4/2012 | Metcalf, Jr. et al. |
| 8,157,841 B2 | 4/2012 | Malandain et al. |

(56) References Cited

U.S. PATENT DOCUMENTS

| | | |
|---|---|---|
| 8,162,897 B2 | 4/2012 | Byrum |
| 8,162,979 B2 | 4/2012 | Sachs et al. |
| 8,163,013 B2 | 4/2012 | Machold et al. |
| 8,177,789 B2 | 5/2012 | Magill et al. |
| 8,182,411 B2 | 5/2012 | Dlugos |
| 8,187,324 B2 | 5/2012 | Webler et al. |
| 8,197,544 B1 | 6/2012 | Manzi et al. |
| 8,202,305 B2 | 6/2012 | Reiley |
| 8,211,127 B2 | 7/2012 | Uth et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,292 B2 | 8/2012 | Collazo |
| 8,241,293 B2 | 8/2012 | Stone et al. |
| 8,241,331 B2 | 8/2012 | Arnin |
| 8,246,630 B2 | 8/2012 | Manzi et al. |
| 8,251,888 B2 | 8/2012 | Roslin et al. |
| 8,252,063 B2 | 8/2012 | Stauch |
| 8,257,370 B2 | 9/2012 | Moskowitz et al. |
| 8,257,442 B2 | 9/2012 | Edie et al. |
| 8,263,024 B2 | 9/2012 | Wan et al. |
| 8,267,969 B2 | 9/2012 | Altarac et al. |
| 8,273,112 B2 | 9/2012 | Garamszegi et al. |
| 8,278,941 B2 | 10/2012 | Kroh et al. |
| 8,282,671 B2 | 10/2012 | Connor |
| 8,287,540 B2 | 10/2012 | LeCronier et al. |
| 8,298,133 B2 | 10/2012 | Wiley et al. |
| 8,298,240 B2 | 10/2012 | Giger et al. |
| 8,308,779 B2 | 11/2012 | Reiley |
| 8,313,423 B2 | 11/2012 | Forsell |
| 8,316,856 B2 | 11/2012 | Nelson et al. |
| 8,317,761 B2 | 11/2012 | Birk et al. |
| 8,317,802 B1 | 11/2012 | Manzi et al. |
| 8,323,290 B2 | 12/2012 | Metzger et al. |
| 8,326,435 B2 | 12/2012 | Stevenson |
| 8,328,807 B2 | 12/2012 | Brigido |
| 8,328,854 B2 | 12/2012 | Baynham et al. |
| 8,333,204 B2 | 12/2012 | Saadat |
| 8,333,790 B2 | 12/2012 | Timm et al. |
| 8,353,913 B2 | 1/2013 | Moskowitz et al. |
| 8,357,169 B2 | 1/2013 | Henniges et al. |
| 8,357,182 B2 | 1/2013 | Seme |
| 8,357,183 B2 | 1/2013 | Seme et al. |
| 8,360,955 B2 | 1/2013 | Sayet et al. |
| 8,366,628 B2 | 2/2013 | Denker et al. |
| 8,372,078 B2 | 2/2013 | Collazo |
| 8,382,652 B2 | 2/2013 | Sayet et al. |
| 8,386,018 B2 | 2/2013 | Stanch et al. |
| 8,388,667 B2 | 3/2013 | Reiley et al. |
| 8,394,124 B2 | 3/2013 | Biyani |
| 8,394,143 B2 | 3/2013 | Grotz et al. |
| 8,403,958 B2 | 3/2013 | Schwab |
| 8,409,203 B2 | 4/2013 | Birk et al. |
| 8,409,281 B2 | 4/2013 | Makower et al. |
| 8,414,584 B2 | 4/2013 | Brigido |
| 8,414,648 B2 | 4/2013 | Reiley |
| 8,419,755 B2 | 4/2013 | Deem et al. |
| 8,419,801 B2 | 4/2013 | DiSilvestro et al. |
| 8,425,570 B2 | 4/2013 | Reiley |
| 8,425,608 B2 | 4/2013 | Dewey et al. |
| 8,433,519 B2 | 4/2013 | Ekseth et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,449,553 B2 | 5/2013 | Kam et al. |
| 8,449,580 B2 | 5/2013 | Voellmicke et al. |
| 8,454,695 B2 | 6/2013 | Grotz et al. |
| 8,469,908 B2 | 6/2013 | Asfora |
| 8,469,978 B2 | 6/2013 | Fobi et al. |
| 8,470,003 B2 | 6/2013 | Voellmicke et al. |
| 8,470,004 B2 | 6/2013 | Reiley |
| 8,475,354 B2 | 7/2013 | Phillips et al. |
| 8,475,356 B2 | 7/2013 | Feng et al. |
| 8,475,499 B2 | 7/2013 | Cournoyer et al. |
| 8,480,554 B2 | 7/2013 | Phillips et al. |
| 8,480,668 B2 | 7/2013 | Fernandez et al. |
| 8,480,741 B2 | 7/2013 | Grotz et al. |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,113 B2 | 7/2013 | Malek |
| 8,486,147 B2 | 7/2013 | de Villiers et al. |
| 8,491,589 B2 | 7/2013 | Fisher et al. |
| 8,494,805 B2 | 7/2013 | Roche et al. |
| 8,496,662 B2 | 7/2013 | Novak et al. |
| 8,500,810 B2 | 8/2013 | Mastrorio et al. |
| 8,506,517 B2 | 8/2013 | Stergiopulos |
| 8,506,569 B2 | 8/2013 | Keefer et al. |
| 8,517,973 B2 | 8/2013 | Burnett |
| 8,518,062 B2 | 8/2013 | Cole et al. |
| 8,518,086 B2 | 8/2013 | Seme et al. |
| 8,522,790 B2 | 9/2013 | Nelson et al. |
| 8,523,865 B2 | 9/2013 | Reglos et al. |
| 8,523,866 B2 | 9/2013 | Sidebotham et al. |
| 8,523,883 B2 | 9/2013 | Saadat |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,529,630 B2 | 9/2013 | Bojarski et al. |
| 8,545,384 B2 | 10/2013 | Forsell |
| 8,545,508 B2 | 10/2013 | Collazo |
| 8,545,814 B2 | 10/2013 | Contag et al. |
| 8,551,092 B2 | 10/2013 | Morgan et al. |
| 8,551,142 B2 | 10/2013 | Altarac et al. |
| 8,551,422 B2 | 10/2013 | Wan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,416 B2 | 10/2013 | Schmitz et al. |
| 8,568,457 B2 | 10/2013 | Hunziker |
| 8,574,267 B2 | 11/2013 | Linares |
| 8,579,919 B2 | 11/2013 | Bolduc et al. |
| 8,579,979 B2 | 11/2013 | Edie et al. |
| 8,585,595 B2 | 11/2013 | Heilman |
| 8,585,702 B2 | 11/2013 | Orsak et al. |
| 8,585,738 B2 | 11/2013 | Linares |
| 8,585,740 B1 | 11/2013 | Ross et al. |
| 8,591,549 B2 | 11/2013 | Lange |
| 8,597,362 B2 | 12/2013 | Shenoy et al. |
| 8,613,749 B2 | 12/2013 | Deem et al. |
| 8,613,758 B2 | 12/2013 | Linares |
| 8,617,212 B2 | 12/2013 | Linares |
| 8,617,220 B2 | 12/2013 | Skaggs |
| 8,617,243 B2 | 12/2013 | Eisermann et al. |
| 8,622,936 B2 | 1/2014 | Schenberger et al. |
| 8,623,036 B2 | 1/2014 | Harrison et al. |
| 8,623,042 B2 | 1/2014 | Roslin et al. |
| 8,623,056 B2 | 1/2014 | Linares |
| 8,632,544 B2 | 1/2014 | Haaja et al. |
| 8,632,547 B2 | 1/2014 | Maxson et al. |
| 8,632,548 B2 | 1/2014 | Soubeiran |
| 8,632,563 B2 | 1/2014 | Nagase et al. |
| 8,632,594 B2 | 1/2014 | Williams et al. |
| 8,636,770 B2 | 1/2014 | Hestad et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,652,175 B2 | 2/2014 | Timm et al. |
| 8,657,765 B2 | 2/2014 | Asfora |
| 8,657,856 B2 | 2/2014 | Gephart et al. |
| 8,657,885 B2 | 2/2014 | Burnett et al. |
| 8,663,139 B2 | 3/2014 | Asfora |
| 8,663,140 B2 | 3/2014 | Asfora |
| 8,663,285 B2 | 3/2014 | Dall et al. |
| 8,663,287 B2 | 3/2014 | Butler et al. |
| 8,663,338 B2 | 3/2014 | Burnett et al. |
| 8,668,719 B2 | 3/2014 | Alamin et al. |

(56) References Cited

U.S. PATENT DOCUMENTS

| | | |
|---|---|---|
| 8,673,001 B2 | 3/2014 | Cartledge et al. |
| 8,679,161 B2 | 3/2014 | Malandain et al. |
| 8,690,858 B2 | 4/2014 | Machold et al. |
| 8,707,959 B2 | 4/2014 | Paraschac et al. |
| 8,709,090 B2 | 4/2014 | Makower et al. |
| 8,715,243 B2 | 5/2014 | Uth et al. |
| 8,715,290 B2 | 5/2014 | Fisher et al. |
| 8,721,570 B2 | 5/2014 | Gupta et al. |
| 8,721,643 B2 | 5/2014 | Morgan et al. |
| 8,728,125 B2 | 5/2014 | Bruneau et al. |
| 8,734,318 B2 | 5/2014 | Forsell |
| 8,734,516 B2 | 5/2014 | Moskowitz et al. |
| 8,734,519 B2 | 5/2014 | de Villiers et al. |
| 8,747,444 B2 | 6/2014 | Moskowitz et al. |
| 8,752,552 B2 | 6/2014 | Nelson et al. |
| 8,758,303 B2 | 6/2014 | Uth et al. |
| 8,758,347 B2 | 6/2014 | Weiner et al. |
| 8,758,355 B2 | 6/2014 | Fisher et al. |
| 8,758,372 B2 | 6/2014 | Cartledge et al. |
| 8,762,308 B2 | 6/2014 | Najarian et al. |
| 8,764,713 B2 | 7/2014 | Uth et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,781,744 B2 | 7/2014 | Ekseth et al. |
| 8,784,482 B2 | 7/2014 | Rahdert et al. |
| 8,790,343 B2 | 7/2014 | McClellan et al. |
| 8,790,380 B2 | 7/2014 | Buttermann |
| 8,790,409 B2 | 7/2014 | Van den Heuvel et al. |
| 8,794,243 B2 | 8/2014 | Deem et al. |
| 8,795,339 B2 | 8/2014 | Boomer et al. |
| 8,801,795 B2 | 8/2014 | Makower et al. |
| 8,808,206 B2 | 8/2014 | Asfora |
| 8,813,727 B2 | 8/2014 | McClendon |
| 8,814,869 B2 | 8/2014 | Freid et al. |
| 8,828,058 B2 | 9/2014 | Elsebaie et al. |
| 8,828,087 B2 | 9/2014 | Stone et al. |
| 8,840,623 B2 | 9/2014 | Reiley |
| 8,840,651 B2 | 9/2014 | Reiley |
| 8,845,692 B2 | 9/2014 | Wisnewski |
| 8,845,724 B2 | 9/2014 | Shenoy et al. |
| 8,864,717 B2 | 10/2014 | Conlon et al. |
| 8,864,823 B2 | 10/2014 | Cartledge et al. |
| 8,870,881 B2 | 10/2014 | Rezach et al. |
| 8,870,918 B2 | 10/2014 | Boomer et al. |
| 8,870,959 B2 | 10/2014 | Arnin |
| 8,882,699 B2 | 11/2014 | Burnett |
| 8,882,830 B2 | 11/2014 | Cartledge et al. |
| 8,888,672 B2 | 11/2014 | Phillips et al. |
| 8,888,673 B2 | 11/2014 | Phillips et al. |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,932,247 B2 | 1/2015 | Stergiopulos |
| 8,945,188 B2 | 2/2015 | Rezach et al. |
| 8,945,210 B2 | 2/2015 | Cartledge et al. |
| 8,956,407 B2 | 2/2015 | Macoviak et al. |
| 8,961,386 B2 | 2/2015 | Phillips et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,986,348 B2 | 3/2015 | Reiley |
| 8,992,527 B2 | 3/2015 | Guichet |
| 9,005,251 B2 | 4/2015 | Heggeness |
| 9,005,293 B2 | 4/2015 | Moskowitz et al. |
| 9,005,298 B2 | 4/2015 | Makower et al. |
| 9,011,491 B2 | 4/2015 | Carl et al. |
| 9,015,057 B2 | 4/2015 | Phillips et al. |
| 9,022,917 B2 | 5/2015 | Kasic et al. |
| 9,028,550 B2 | 5/2015 | Shulock et al. |
| 9,033,957 B2 | 5/2015 | Cadeddu et al. |
| 9,033,988 B2 | 5/2015 | Gephart et al. |
| 9,034,016 B2 | 5/2015 | Panjabi |
| 9,044,218 B2 | 6/2015 | Young |
| 9,060,810 B2 | 6/2015 | Kercher et al. |
| 9,060,844 B2 | 6/2015 | Kagan et al. |
| 9,072,530 B2 | 7/2015 | Mehta et al. |
| 9,072,606 B2 | 7/2015 | Lucas et al. |
| 9,078,703 B2 | 7/2015 | Arnin |
| 9,084,632 B2 | 7/2015 | Orsak et al. |
| 9,089,348 B2 | 7/2015 | Chavarria et al. |
| 9,095,436 B2 | 8/2015 | Boyden et al. |
| 9,095,437 B2 | 8/2015 | Boyden et al. |
| 9,101,422 B2 | 8/2015 | Freid et al. |
| 9,101,427 B2 | 8/2015 | Globerman et al. |
| 9,107,706 B2 | 8/2015 | Alamin et al. |
| 9,113,967 B2 | 8/2015 | Soubeiran |
| 9,114,016 B2 | 8/2015 | Shenoy et al. |
| 9,125,746 B2 | 9/2015 | Clifford et al. |
| 9,138,266 B2 | 9/2015 | Stauch |
| 9,144,482 B2 | 9/2015 | Sayet |
| 9,155,565 B2 | 10/2015 | Boomer et al. |
| 9,161,856 B2 | 10/2015 | Nelson et al. |
| 9,168,071 B2 | 10/2015 | Seme et al. |
| 9,168,076 B2 | 10/2015 | Patty et al. |
| 9,173,681 B2 | 11/2015 | Seme |
| 9,173,715 B2 | 11/2015 | Baumgartner |
| 9,186,158 B2 | 11/2015 | Anthony et al. |
| 9,186,185 B2 | 11/2015 | Hestad et al. |
| 9,198,771 B2 | 12/2015 | Ciupik |
| 9,204,899 B2 | 12/2015 | Buttermann |
| 9,204,908 B2 | 12/2015 | Buttermann |
| 9,220,536 B2 | 12/2015 | Skaggs |
| 9,226,783 B2 | 1/2016 | Brigido |
| 9,242,070 B2 | 1/2016 | Tieu |
| 9,259,243 B2 | 2/2016 | Giger et al. |
| 9,272,159 B2 | 3/2016 | Phillips et al. |
| 9,278,004 B2 | 3/2016 | Shenoy et al. |
| 9,278,046 B2 | 3/2016 | Asfora |
| 9,282,997 B2 | 3/2016 | Hunziker |
| 9,301,792 B2 | 4/2016 | Henniges et al. |
| 9,301,854 B2 | 4/2016 | Moskowitz et al. |
| 9,308,089 B2 | 4/2016 | Vicatos et al. |
| 9,308,387 B2 | 4/2016 | Phillips et al. |
| 9,320,618 B2 | 4/2016 | Schmitz et al. |
| 9,326,728 B2 | 5/2016 | Demir et al. |
| 9,333,009 B2 | 5/2016 | Kroll et al. |
| 9,339,197 B2 | 5/2016 | Griswold et al. |
| 9,339,300 B2 | 5/2016 | Kantelhardt |
| 9,339,307 B2 | 5/2016 | McClintock et al. |
| 9,339,312 B2 | 5/2016 | Doherty et al. |
| 9,358,044 B2 | 6/2016 | Seme et al. |
| 9,364,267 B2 | 6/2016 | Northcutt et al. |
| 9,370,388 B2 | 6/2016 | Globerman et al. |
| 9,393,123 B2 | 7/2016 | Lucas et al. |
| 9,408,644 B2 | 8/2016 | Zahrly et al. |
| 9,421,347 B2 | 8/2016 | Burnett |
| 9,427,267 B2 | 8/2016 | Homeier et al. |
| 9,439,744 B2 | 9/2016 | Forsell |
| 9,439,797 B2 | 9/2016 | Baym et al. |
| 9,445,848 B2 | 9/2016 | Anderson et al. |
| 9,451,997 B2 | 9/2016 | Carl et al. |
| 9,456,953 B2 | 10/2016 | Asfora |
| 9,474,612 B2 | 10/2016 | Haaja et al. |
| 9,492,199 B2 | 11/2016 | Orsak et al. |
| 9,492,276 B2 | 11/2016 | Lee et al. |
| 9,498,258 B2 | 11/2016 | Boomer et al. |
| 9,498,366 B2 | 11/2016 | Burnett et al. |
| 9,510,834 B2 | 12/2016 | Burnett et al. |
| 9,532,804 B2 | 1/2017 | Clifford et al. |
| 9,561,062 B2 | 2/2017 | Hayes et al. |
| 9,561,063 B2 | 2/2017 | Reiley |
| 9,572,588 B2 | 2/2017 | Fisher et al. |
| 9,572,746 B2 | 2/2017 | Asfora |
| 9,572,910 B2 | 2/2017 | Messersmith et al. |
| 9,579,110 B2 | 2/2017 | Bojarski et al. |
| 9,579,203 B2 | 2/2017 | Soubeiran |
| 9,603,605 B2 | 3/2017 | Collazo |
| 9,603,713 B2 | 3/2017 | Moskowitz et al. |
| 9,610,161 B2 | 4/2017 | Macoviak et al. |
| 9,622,875 B2 | 4/2017 | Moskowitz et al. |
| 9,642,735 B2 | 5/2017 | Burnett |

(56) References Cited

U.S. PATENT DOCUMENTS

| | | | |
|---|---|---|---|
| 9,655,651 B2 | 5/2017 | Panjabi |
| 9,668,868 B2 | 6/2017 | Shenoy et al. |
| 9,687,243 B2 | 6/2017 | Burnett et al. |
| 9,687,414 B2 | 6/2017 | Asfora |
| 9,693,867 B2 | 7/2017 | Lucas et al. |
| 9,700,419 B2 | 7/2017 | Clifford et al. |
| 9,700,450 B2 | 7/2017 | Burnett |
| 9,717,537 B2 | 8/2017 | Gordon |
| 9,724,135 B2 | 8/2017 | Koch et al. |
| 9,724,265 B2 | 8/2017 | Asfora |
| 9,730,738 B2 | 8/2017 | Gephart et al. |
| 9,743,969 B2 | 8/2017 | Reiley |
| 9,782,206 B2 | 10/2017 | Mueckter et al. |
| 9,795,410 B2 | 10/2017 | Shenoy et al. |
| 9,814,600 B2 | 11/2017 | Shulock et al. |
| 9,820,789 B2 | 11/2017 | Reiley |
| 9,826,987 B2 | 11/2017 | Keefer et al. |
| 9,833,291 B2 | 12/2017 | Baumgartner |
| 9,848,894 B2 | 12/2017 | Burley et al. |
| 9,848,993 B2 | 12/2017 | Moskowitz et al. |
| 9,861,376 B2 | 1/2018 | Chavarria et al. |
| 9,861,390 B2 | 1/2018 | Hunziker |
| 9,861,404 B2 | 1/2018 | Reiley |
| 9,867,719 B2 | 1/2018 | Moskowitz et al. |
| 2001/0011543 A1 | 8/2001 | Forsell |
| 2002/0019580 A1 | 2/2002 | Lau et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0019498 A1 | 1/2003 | Forsell |
| 2003/0040671 A1 | 2/2003 | Somogyi et al. |
| 2003/0066536 A1 | 4/2003 | Forsell |
| 2003/0093117 A1* | 5/2003 | Saadat | A61B 18/00 606/221 |
| 2003/0114731 A1 | 6/2003 | Cadeddu et al. |
| 2003/0187447 A1 | 10/2003 | Ferrante et al. |
| 2003/0208212 A1 | 11/2003 | Cigaina |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0064030 A1 | 4/2004 | Forsell |
| 2004/0068205 A1 | 4/2004 | Zogbi et al. |
| 2004/0092939 A1 | 5/2004 | Freid et al. |
| 2004/0098121 A1 | 5/2004 | Opolski |
| 2004/0116773 A1 | 6/2004 | Furness et al. |
| 2004/0133219 A1 | 7/2004 | Forsell |
| 2004/0138725 A1 | 7/2004 | Forsell |
| 2004/0153106 A1 | 8/2004 | Dudai |
| 2004/0158254 A1 | 8/2004 | Eisermann |
| 2004/0172040 A1 | 9/2004 | Heggeness |
| 2004/0173222 A1 | 9/2004 | Kim |
| 2004/0193266 A1 | 9/2004 | Meyer |
| 2004/0220567 A1 | 11/2004 | Eisermann et al. |
| 2004/0220668 A1 | 11/2004 | Eisermann et al. |
| 2004/0230307 A1 | 11/2004 | Eisermann |
| 2004/0250820 A1 | 12/2004 | Forsell |
| 2004/0260287 A1 | 12/2004 | Ferree |
| 2004/0260319 A1 | 12/2004 | Egle |
| 2005/0002984 A1 | 1/2005 | Byrum et al. |
| 2005/0043802 A1 | 2/2005 | Eisermann et al. |
| 2005/0055025 A1 | 3/2005 | Zacouto et al. |
| 2005/0060030 A1* | 3/2005 | Lashinski | A61F 2/2466 623/2.37 |
| 2005/0070937 A1 | 3/2005 | Jambor et al. |
| 2005/0080427 A1 | 4/2005 | Govari et al. |
| 2005/0080439 A1 | 4/2005 | Carson et al. |
| 2005/0090823 A1 | 4/2005 | Bartimus |
| 2005/0096750 A1 | 5/2005 | Kagan et al. |
| 2005/0131352 A1 | 6/2005 | Conlon et al. |
| 2005/0143765 A1 | 6/2005 | Bachmann |
| 2005/0159754 A1 | 7/2005 | Odrich |
| 2005/0159755 A1 | 7/2005 | Odrich |
| 2005/0165440 A1 | 7/2005 | Cancel et al. |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182412 A1 | 8/2005 | Johnson et al. |
| 2005/0192629 A1 | 9/2005 | Saadat et al. |
| 2005/0222489 A1 | 10/2005 | Rahdert et al. |
| 2005/0234289 A1 | 10/2005 | Anstadt et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2005/0288672 A1 | 12/2005 | Ferree |
| 2006/0020278 A1 | 1/2006 | Burnett et al. |
| 2006/0036251 A1 | 2/2006 | Reiley |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0079897 A1 | 4/2006 | Harrison et al. |
| 2006/0116757 A1 | 6/2006 | Lashinski et al. |
| 2006/0124140 A1 | 6/2006 | Forsell |
| 2006/0136062 A1 | 6/2006 | DiNello et al. |
| 2006/0142634 A1 | 6/2006 | Anstadt et al. |
| 2006/0142767 A1 | 6/2006 | Green et al. |
| 2006/0155279 A1 | 7/2006 | Ogilvie |
| 2006/0155347 A1 | 7/2006 | Forsell |
| 2006/0184240 A1 | 8/2006 | Jimenez et al. |
| 2006/0184248 A1 | 8/2006 | Edidin et al. |
| 2006/0195102 A1 | 8/2006 | Malandain |
| 2006/0204156 A1 | 9/2006 | Takehara et al. |
| 2006/0211909 A1 | 9/2006 | Anstadt et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241748 A1 | 10/2006 | Lee |
| 2006/0249914 A1 | 11/2006 | Dulin |
| 2006/0252982 A1 | 11/2006 | Hassler, Jr. |
| 2006/0252983 A1 | 11/2006 | Lembo et al. |
| 2006/0271107 A1 | 11/2006 | Harrison et al. |
| 2006/0276812 A1 | 12/2006 | Hill et al. |
| 2006/0282073 A1 | 12/2006 | Simanovsky |
| 2006/0289014 A1 | 12/2006 | Purdy et al. |
| 2006/0293671 A1 | 12/2006 | Heggeness |
| 2006/0293683 A1 | 12/2006 | Stauch |
| 2007/0004999 A1 | 1/2007 | Miethke |
| 2007/0010814 A1 | 1/2007 | Stauch |
| 2007/0015955 A1 | 1/2007 | Tsonton |
| 2007/0021644 A1 | 1/2007 | Woolson et al. |
| 2007/0027356 A1 | 2/2007 | Ortiz |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0055237 A1 | 3/2007 | Edidin et al. |
| 2007/0055368 A1 | 3/2007 | Rhee et al. |
| 2007/0118215 A1 | 5/2007 | Moaddeb |
| 2007/0135913 A1 | 6/2007 | Moaddeb et al. |
| 2007/0162032 A1 | 7/2007 | Johnson et al. |
| 2007/0173837 A1 | 7/2007 | Chan et al. |
| 2007/0173869 A1 | 7/2007 | Gannoe et al. |
| 2007/0179493 A1 | 8/2007 | Kim |
| 2007/0213751 A1* | 9/2007 | Scirica | A61F 5/0053 606/157 |
| 2007/0233239 A1* | 10/2007 | Navia | A61F 2/2466 623/2.37 |
| 2007/0239159 A1 | 10/2007 | Altarac et al. |
| 2007/0250084 A1 | 10/2007 | Sharkawy et al. |
| 2007/0255088 A1 | 11/2007 | Jacobson et al. |
| 2007/0256693 A1 | 11/2007 | Paraschac et al. |
| 2007/0260270 A1 | 11/2007 | Assell et al. |
| 2007/0264605 A1 | 11/2007 | Belfor et al. |
| 2007/0270631 A1 | 11/2007 | Nelson et al. |
| 2007/0276369 A1 | 11/2007 | Allard et al. |
| 2007/0276372 A1 | 11/2007 | Malandain et al. |
| 2007/0276373 A1 | 11/2007 | Malandain |

(56) References Cited

U.S. PATENT DOCUMENTS

| | | |
|---|---|---|
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0033431 A1 | 2/2008 | Jung et al. |
| 2008/0051784 A1 | 2/2008 | Gollogly |
| 2008/0051895 A1 | 2/2008 | Malandain et al. |
| 2008/0058936 A1 | 3/2008 | Malandain et al. |
| 2008/0058937 A1 | 3/2008 | Malandain et al. |
| 2008/0065077 A1 | 3/2008 | Ferree |
| 2008/0065215 A1 | 3/2008 | Reiley |
| 2008/0066764 A1 | 3/2008 | Paraschac et al. |
| 2008/0071275 A1 | 3/2008 | Ferree |
| 2008/0071276 A1 | 3/2008 | Ferree |
| 2008/0082118 A1 | 4/2008 | Edidin et al. |
| 2008/0082167 A1 | 4/2008 | Edidin et al. |
| 2008/0083413 A1 | 4/2008 | Forsell |
| 2008/0086128 A1 | 4/2008 | Lewis |
| 2008/0091059 A1 | 4/2008 | Machold et al. |
| 2008/0091264 A1 | 4/2008 | Machold |
| 2008/0097487 A1 | 4/2008 | Pool |
| 2008/0097523 A1 | 4/2008 | Bolduc et al. |
| 2008/0108995 A1 | 5/2008 | Conway et al. |
| 2008/0140188 A1 | 6/2008 | Rahdert et al. |
| 2008/0147139 A1 | 6/2008 | Barrett et al. |
| 2008/0147192 A1 | 6/2008 | Edidin et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0183285 A1* | 7/2008 | Shaoulian ............ A61F 2/2448 623/2.37 |
| 2008/0195156 A1 | 8/2008 | Ainsworth et al. |
| 2008/0226563 A1 | 9/2008 | Contag et al. |
| 2008/0228186 A1 | 9/2008 | Gall et al. |
| 2008/0243150 A1* | 10/2008 | Starksen ............ A61B 17/0644 606/151 |
| 2008/0255615 A1 | 10/2008 | Vittur et al. |
| 2008/0272928 A1 | 11/2008 | Shuster |
| 2008/0275552 A1 | 11/2008 | Makower et al. |
| 2008/0275555 A1 | 11/2008 | Makower et al. |
| 2008/0275557 A1 | 11/2008 | Makower et al. |
| 2008/0275567 A1 | 11/2008 | Makower et al. |
| 2008/0293995 A1 | 11/2008 | Moaddeb et al. |
| 2009/0076597 A1* | 3/2009 | Dahlgren ............ A61B 17/7016 623/2.1 |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0118699 A1 | 5/2009 | Utley et al. |
| 2009/0171356 A1 | 7/2009 | Klett |
| 2009/0177203 A1 | 7/2009 | Reiley |
| 2009/0182356 A1 | 7/2009 | Coe |
| 2009/0192514 A1 | 7/2009 | Feinberg et al. |
| 2009/0198144 A1 | 8/2009 | Phillips et al. |
| 2009/0204055 A1 | 8/2009 | Lennox et al. |
| 2009/0216113 A1 | 8/2009 | Meier et al. |
| 2009/0216262 A1 | 8/2009 | Burnett et al. |
| 2009/0240173 A1 | 9/2009 | Hsia et al. |
| 2009/0259236 A2 | 10/2009 | Burnett et al. |
| 2009/0270871 A1 | 10/2009 | Liu et al. |
| 2009/0275984 A1 | 11/2009 | Kim et al. |
| 2009/0318919 A1 | 12/2009 | Robinson |
| 2010/0004654 A1 | 1/2010 | Schmitz et al. |
| 2010/0030281 A1 | 2/2010 | Gollogly |
| 2010/0057127 A1 | 3/2010 | McGuire et al. |
| 2010/0081868 A1 | 4/2010 | Moaddeb et al. |
| 2010/0100185 A1 | 4/2010 | Trieu et al. |
| 2010/0106192 A1 | 4/2010 | Barry |
| 2010/0106193 A1 | 4/2010 | Barry |
| 2010/0114103 A1 | 5/2010 | Harrison et al. |
| 2010/0121457 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0179601 A1 | 7/2010 | Jung et al. |
| 2010/0198261 A1 | 8/2010 | Trieu et al. |
| 2010/0228167 A1 | 9/2010 | Ilovich et al. |
| 2010/0241168 A1 | 9/2010 | Franck et al. |
| 2010/0249782 A1 | 9/2010 | Durham |
| 2010/0249839 A1 | 9/2010 | Alamin et al. |
| 2010/0249847 A1 | 9/2010 | Jung et al. |
| 2010/0256626 A1 | 10/2010 | Muller et al. |
| 2010/0274290 A1 | 10/2010 | Jung et al. |
| 2010/0286730 A1 | 11/2010 | Gordon |
| 2010/0286791 A1 | 11/2010 | Goldsmith |
| 2010/0318129 A1 | 12/2010 | Seme et al. |
| 2010/0324684 A1 | 12/2010 | Eisermann et al. |
| 2010/0331883 A1 | 12/2010 | Schmitz et al. |
| 2011/0004076 A1 | 1/2011 | Janna et al. |
| 2011/0009956 A1* | 1/2011 | Cartledge ........ A61B 17/00234 623/2.11 |
| 2011/0022169 A1 | 1/2011 | Ryan |
| 2011/0057756 A1 | 3/2011 | Marinescu et al. |
| 2011/0060422 A1 | 3/2011 | Makower et al. |
| 2011/0098748 A1 | 4/2011 | Jangra |
| 2011/0130702 A1 | 6/2011 | Stergiopulos |
| 2011/0184505 A1 | 7/2011 | Sharkawy et al. |
| 2011/0190879 A1 | 8/2011 | Bobo |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0230961 A1 | 9/2011 | Langer |
| 2011/0257655 A1 | 10/2011 | Copf, Jr. |
| 2011/0275879 A1 | 11/2011 | Nelson et al. |
| 2011/0284014 A1 | 11/2011 | Cadeddu et al. |
| 2011/0313516 A1 | 12/2011 | Dang |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0089186 A1 | 4/2012 | Carl et al. |
| 2012/0089191 A1 | 4/2012 | Altarac et al. |
| 2012/0109207 A1 | 5/2012 | Trieu |
| 2012/0116522 A1 | 5/2012 | Makower et al. |
| 2012/0116535 A1 | 5/2012 | Ratron et al. |
| 2012/0130426 A1 | 5/2012 | Thompson |
| 2012/0136436 A1 | 5/2012 | Cabiri |
| 2012/0136449 A1 | 5/2012 | Makower et al. |
| 2012/0172883 A1 | 7/2012 | Sayago |
| 2012/0179273 A1 | 7/2012 | Clifford et al. |
| 2012/0185040 A1 | 7/2012 | Rahdert et al. |
| 2012/0197392 A1 | 8/2012 | Dumontelle |
| 2012/0221101 A1 | 8/2012 | Moaddeb et al. |
| 2012/0271353 A1 | 10/2012 | Barry |
| 2012/0277747 A1 | 11/2012 | Keller |
| 2012/0296234 A1 | 11/2012 | Wilhelm et al. |
| 2012/0312307 A1 | 12/2012 | Paraschac et al. |
| 2013/0013059 A1 | 1/2013 | Tozzi |
| 2013/0013066 A1 | 1/2013 | Landry et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0079830 A1 | 3/2013 | Garamszegi et al. |
| 2013/0138017 A1 | 5/2013 | Jundt et al. |
| 2013/0138154 A1 | 5/2013 | Reiley |
| 2013/0150889 A1 | 6/2013 | Fening et al. |
| 2013/0178903 A1 | 7/2013 | Abdou |
| 2013/0197639 A1 | 8/2013 | Clifford et al. |
| 2013/0204266 A1 | 8/2013 | Heilman |
| 2013/0204376 A1 | 8/2013 | DiSilvestro et al. |
| 2013/0238094 A1 | 9/2013 | Voellmicke et al. |
| 2013/0253587 A1 | 9/2013 | Carls et al. |
| 2013/0261623 A1 | 10/2013 | Voellmicke et al. |
| 2013/0261672 A1 | 10/2013 | Horvath |
| 2013/0296863 A1 | 11/2013 | Globerman et al. |
| 2013/0325006 A1 | 12/2013 | Michelinie et al. |

(56) References Cited

U.S. PATENT DOCUMENTS

| | | |
|---|---|---|
| 2013/0325071 A1 | 12/2013 | Niemiec et al. |
| 2013/0331889 A1 | 12/2013 | Alamin et al. |
| 2013/0345802 A1 | 12/2013 | Cartledge et al. |
| 2014/0018913 A1 | 1/2014 | Cartledge et al. |
| 2014/0031826 A1 | 1/2014 | Bojarski et al. |
| 2014/0031929 A1 | 1/2014 | Cartledge et al. |
| 2014/0039558 A1 | 2/2014 | Alamin et al. |
| 2014/0051914 A1 | 2/2014 | Fobi et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0067075 A1 | 3/2014 | Makower et al. |
| 2014/0080203 A1 | 3/2014 | Wan et al. |
| 2014/0107704 A1 | 4/2014 | Serhan et al. |
| 2014/0135838 A1 | 5/2014 | Alamin et al. |
| 2014/0142698 A1 | 5/2014 | Landry et al. |
| 2014/0163664 A1 | 6/2014 | Goldsmith |
| 2014/0172097 A1 | 6/2014 | Clifford et al. |
| 2014/0194932 A1 | 7/2014 | Bruneau et al. |
| 2014/0222138 A1 | 8/2014 | Machold et al. |
| 2014/0296918 A1 | 10/2014 | Fening et al. |
| 2014/0303539 A1 | 10/2014 | Baym et al. |
| 2014/0303540 A1 | 10/2014 | Baym et al. |
| 2014/0336756 A1 | 11/2014 | Lee et al. |
| 2014/0358150 A1 | 12/2014 | Kaufman et al. |
| 2015/0013687 A1 | 1/2015 | Paraschac et al. |
| 2015/0057490 A1 | 2/2015 | Forsell |
| 2015/0073565 A1 | 3/2015 | Nelson et al. |
| 2015/0105782 A1 | 4/2015 | D'Lima et al. |
| 2015/0105824 A1 | 4/2015 | Moskowitz et al. |
| 2015/0112432 A1 | 4/2015 | Reich |
| 2015/0132174 A1 | 5/2015 | Marinescu et al. |
| 2015/0134007 A1 | 5/2015 | Alamin et al. |
| 2015/0142110 A1 | 5/2015 | Myers et al. |
| 2015/0150561 A1 | 6/2015 | Burnett et al. |
| 2015/0223820 A1 | 8/2015 | Olson |
| 2015/0272600 A1 | 10/2015 | Mehta et al. |
| 2015/0313649 A1 | 11/2015 | Alamin et al. |
| 2016/0135953 A1* | 5/2016 | Alon .................... A61F 2/2466 623/2.11 |
| 2017/0367825 A1 | 12/2017 | Cabiri |

FOREIGN PATENT DOCUMENTS

| | | |
|---|---|---|
| WO | WO9850309 | 11/1998 |
| WO | 1999023744 A1 | 5/1999 |
| WO | 2007118179 A2 | 10/2007 |

OTHER PUBLICATIONS

Abe, Jun, Kensei Nagata, Mamoru Ariyoshi, and Akio Inoue. "Experimental external fixation combined with percutaneous discectomy in the management of scoliosis." Spine 24, No. 7 (1999): 646-653.

Amer, A. R. A. L., and Ashraf A. Khanfour. "Evaluation of treatment of late-onset tibia vara using gradual angulationtranslation high tibial osteotomy." Acta orthopaedica Belgica 76, No. 3 (2010): 360.

Baumgart, Rainer, Stefan Hinterwimmer, Michael Krammer, Oliver Muensterer, and Wolf Mutschler. "The bioexpandable prosthesis: a new perspective after resection of malignant bone tumors in children." Journal of pediatric hematology/oncology 27, No. 8 (2005): 452-455.

Baumgart, R., P. Thaller, S. Hinterwimmer, M. Krammer, T. Hierl, and W. Mutschler. "A fully implantable, programmable distraction nail (Fitbone)—new perspectives for corrective and reconstructive limb surgery." In Practice of Intramedullary Locked Nails, pp. 189-198. Springer Berlin Heidelberg, 2006.

Bodó, László, László Hangody, Balázs Borsitzky, György Béres, Gabriella Arató, Péter Nagy, and Gábor K. Ráthonyi. "Development of a tension-adjustable implant for anterior cruciate ligament reconstruction." Eklem Hast Cerrahisi 19, No. 1 (2008): 27-32.

Brochure-VEPTR II Technique Guide Apr. 2008.

Buchowski, Jacob M., Rishi Bhatnagar, David L. Skaggs, and Paul D. Sponseller. "Temporary internal distraction as an aid to correction of severe scoliosis." The Journal of Bone & Joint Surgery 88, No. 9 (2006): 2035-2041.

Burghardt, R. D., J. E. Herzenberg, S. C. Specht, and D. Paley. "Mechanical failure of the Intramedullary Skeletal Kinetic Distractor in limb lengthening." Journal of Bone & Joint Surgery, British vol. 93, No. 5 (2011): 639-643.

Burke, John Gerard. "Design of a minimally invasive non fusion device for the surgical management of scoliosis in the skeletally immature." Studies in health technology and informatics 123 (2005): 378-384.

Carter, D. R., and W. E. Caler. "A cumulative damage model for bone fracture." Journal of Orthopaedic Research 3, No. 1 (1985): 84-90.

Cole, J., D. Paley, and M. Dahl. "Operative Technique. ISKD. Intramedullary Skeletal Kinetic Distractor. Tibial Surgical Technique." IS-0508 (A)-OPT-US© Orthofix Inc 28 (2005).

Daniels, A. U., Patrick Gemperline, Allen R. Grahn, and Harold K. Dunn. "A new method for continuous intraoperative measurement of Harrington rod loading patterns." Annals of biomedical engineering 12, No. 3 (1984): 233-246.

Dorsey, W. O., Bruce S. Miller, Jared P. Tadje, and Cari R. Bryant. "The stability of three commercially available implants used in medial opening wedge high tibial osteotomy." The journal of knee surgery 19, No. 2 (2006): 95-98.

Edeland, H. G., G. Eriksson, and E. Dahlberg. "Instrumentation for distraction by limited surgery in scoliosis treatment." Journal of biomedical engineering 3, No. 2 (1981): 143-146.

Ember, T., and H. Noordeen. "Distraction forces required during growth rod lengthening." Journal of Bone & Joint Surgery, British vol. 88, No. Supp II (2006): 229-229.

Gao, Xiaochong, Derek Gordon, Dongping Zhang, Richard Browne, Cynthia Helms, Joseph Gillum, Samuel Weber et al. "CHD7 gene polymorphisms are associated with susceptibility to idiopathic scoliosis." The American Journal of Human Genetics 80, No. 5 (2007): 957-965.

Gebhart, M., M. Neel, A. Soubeiran, and J. Dubousset. "Early clinical experience with a custom made growing endoprosthesis in children with malignant bone tumors of the lower extremity actioned by an external permanent magnet: the Phenix M system." In International Society of Limb Salvage 14th International Symposium on Limb Salvage.2007.

Gillespie, R., and J. Obrien. "Harrington instrumentation without fusion." In Journal of Bone and Joint Surgerybritish Volume. vol. 63, No. 3, pp. 461-461. 22 Buckingham Street, London, England WC2N 6ET: British Editorial Soc Bone Joint Surgery, 1981.

Grass, P. Jose, A. Valentin Soto, and H. Paula Araya. "Intermittent distracting rod for correction of high neurologic risk congenital scoliosis." Spine 22, No. 16 (1997): 1922-1927.

Gray's Anatomy, http://education.yahoo.com/reference/gray/subjects/subject/128, published Jul. 1, 2007.

Grimer, R., S. Carter, R. Tillman, A. Abudu, and L. Jeys. "Non-Invasive Extendable Endoprostheses for Children-Expensive but Worth It!." Journal of Bone & Joint Surgery, British vol. 93, No. Supp I (2011): 5-5.

Guichet, Jean-Marc, Barbara Deromedis, Leo T. Donnan, Giovanni Peretti, Pierre Lascombes, and Flavio Bado. "Gradual femoral lengthening with the Albizzia intramedullary nail." The Journal of Bone & Joint Surgery 85, No. 5 (2003): 838-848.

Gupta, A., J. Meswania, R. Pollock, S. R. Cannon, T. W. R. Briggs, S. Taylor, and G. Blunn. "Non-invasive distal femoral expandable endoprosthesis for limb-salvage surgery in paediatric tumours." Journal of Bone & Joint Surgery, British vol. 88, No. 5 (2006): 649-654.

Hankemeier S, Gösling T, Pape HC, et al. Limb lengthening with the Intramedullary Skeletal Kinetic Distractor (ISKD) Oper Orthop Traumatol. 2005;17:79-101.

Harrington PR (1962) Treatment of scoliosis. Correction and internal fixation by spine instrumentation. J Bone Joint Surg Am 44-A:591-610.

(56) References Cited

OTHER PUBLICATIONS

Hazem Elsebaie, M. D. "Single Growing Rods." Changing the Foundations: Does it affect the Results., J Child Orthop. (2007) 1:258.
Hennig, Alex C.; Incavo, Stephen J.; Beynnon, Bruce D.; Abate, Joseph A.; Urse, John S.; Kelly, Stephen / The safety and efficacy of a new adjustable plate used for proximal tibial opening wedge osteotomy in the treatment of unicompartmental knee osteoarthrosis. In: The journal of knee surgery, vol. 20, No. 1, Jan. 1, 2007, p. 6-14.
Hofmeister, M., C. Hierholzer, and V. Bühren. "Callus Distraction with the Albizzia Nail." In Practice of Intramedullary Locked Nails, pp. 211-215. Springer Berlin Heidelberg, 2006.
Hyodo, Akira, Helmuth Kotschi, Helen Kambic, and George Muscheler. "Bone transport using intramedullary fixation and a single flexible traction cable." Clinical orthopaedics and related research 325 (1996): 256-268.
Ahlbom, A., U. Bergqvist, J. H. Bernhardt, J. P. Cesarini, M. Grandolfo, M. Hietanen, A. F. Mckinlay et al. "Guidelines for limiting exposure to time-varying electric, magnetic, and electromagnetic fields (up to 300 GHz). International Commission on Non-Ionizing Radiation Protection." Health Phys 74, No. 4 (1998): 494-522.
International Commission on Non-Ionizing Radiation Protection. "Guidelines on limits of exposure to static magnetic fields." Health Physics 96, No. 4 (2009): 504-514.
Kenawey, Mohamed, Christian Krettek, Emmanouil Liodakis, Ulrich Wiebking, and Stefan Hankemeier. "Leg lengthening using intramedullay skeletal kinetic distractor: results of 57 consecutive applications." Injury 42, No. 2 (2011): 150-155.
Klemme, William R., Francis Denis, Robert B. Winter, John W. Lonstein, and Steven E. Koop. "Spinal instrumentation without fusion for progressive scoliosis in young children." Journal of Pediatric Orthopaedics 17, No. 6 (1997): 734-742.
Krieg, Andreas H., Bernhard M. Speth, and Bruce K. Foster. "Leg lengthening with a motorized nail in adolescents." Clinical orthopaedics and related research 466, No. 1 (2008): 189-197.
Lonner, Baron S. "Emerging minimally invasive technologies for the management of scoliosis." Orthopedic Clinics of North America 38, No. 3 (2007): 431-440.
Teli, Marco MD. "Measurement of Forces Generated During Distraction of Growing Rods, J." Marco Teli. Journal of Child Orthop 1 (2007): 257-258.
Mineiro, Jorge, and Stuart L. Weinstein. "Subcutaneous rodding for progressive spinal curvatures: early results." Journal of Pediatric Orthopaedics 22, No. 3 (2002): 290-295.
Moe, John H., Khalil Kharrat, Robert B. Winter, and John L. Cummine. "Harrington instrumentation without fusion plus external orthotic support for the treatment of difficult curvature problems in young children." Clinical orthopaedics and related research 185 (1984): 35-45.
Montague, R. G., C. M. Bingham, and K. Atallah. "Magnetic gear dynamics for servo control." In MELECON 2010-2010 15th IEEE Mediterranean Electrotechnical Conference, pp. 1192-1197. IEEE, 2010.
Nachemson, Alf, and Gösta Elfström. "Intravital wireless telemetry of axial forces in Harrington distraction rods in patients with idiopathic scoliosis." The Journal of Bone & Joint Surgery 53, No. 3 (1971): 445-465.
Nachlas, I. William, and Jesse N. Borden. "The cure of experimental scoliosis by directed growth control." The Journal of Bone & Joint Surgery 33, No. 1 (1951): 24-34.
Newton, P. "Fusionless Scoliosis Correction by Anterolateral Tethering . . . Can it Work?." In 39th Annual Scoliosis Research Society Meeting. 2004.
Prontes, Isabel, http://wwwehow.com/about_4795793_longest-bone-body.html, published Jun. 12, 2012.
Rathjen, Karl, Megan Wood, Anna McClung, and Zachary Vest. "Clinical and radiographic results after implant removal in idiopathic scoliosis." Spine 32, No. 20 (2007): 2184-2188.
Reyes-Sánchez, Alejandro, Luis Miguel Rosales, and Victor Miramontes. "External fixation for dynamic correction of severe scoliosis." The Spine Journal 5, No. 4 (2005): 418-426.
Rinsky, Lawrence A., James G. Gamble, and Eugene E. Bieck. "Segmentai Instrumentation Without Fusion in Children With Progressive Scoliosis." Journal of Pediatric Orthopaedics 5, No. 6 (1985): 687-690.
Schmerling, M. A., M. A. Wilkov, A. E. Sanders, and J. E. Woosley. "Using the shape recovery of nitinol in the Harrington rod treatment of scoliosis." Journal of biomedical materials research 10, No. 6 (1976): 879-892.
Sharke, Paul. "The machinery of life." Mechanical Engineering 126, No. 2 (2004): 30.
Shiha, Anis, Mohamed Alam El-Deen, Abdel Rahman Khalifa, and Mohamed Kenawey. "Ilizarov gradual correction of genu varum deformity in adults." Acta Orthop Belg 75 (2009): 784-91.
Simpson, A. H. W. R., H. Shalaby, and G. Keenan. "Femoral lengthening with the intramedullary skeletal kinetic distractor." Journal of Bone & Joint Surgery, British vol. 91, No. 7 (2009): 955-961.
Smith, John T. "The use of growth-sparing instrumentation in pediatric spinal deformity." Orthopedic Clinics of North America 38, No. 4 (2007): 547-552.
Soubeiran, A., M. Gebhart, L. Miladi, J. Griffet, M. Neel, and J. Dubousset. "The Phenix M System. A Mechanical Fully Implanted Lengthening Device Externally Controllable Through the Skin with a Palm Size Permanent Magnet; Applications to Pediatric Orthopaedics." In 6th European Research Conference in Pediatric Orthopaedics. 2006.
Stokes, Oliver M., Elizabeth J. O'Donovan, Dino Samartzis, Cora H. Bow, Keith DK Luk, and Kenneth MC Cheung. Reducing radiation exposure in early-onset scoliosis surgery patients: novel use of ultrasonography to measure lengthening in magnet.
Takaso, Masashi, Hideshige Moriya, Hiroshi Kitahara, Shohei Minami, Kazuhisa Takahashi, Keijiro Isobe, Masatsune Yamagata, Yoshinori Otsuka, Yoshinori Nakata, and Masatoshi Inoue. "New remote-controlled growing-rod spinal instrumentation possibly applicable for scoliosis in young children." Journal of orthopaedic science 3, No. 6 (1998): 336-340.
Tello, Carlos A. "Harrington instrumentation without arthrodesis and consecutive distraction program for young children with severe spinal deformities. Experience and technical details." The Orthopedic clinics of North America 25, No. 2 (1994): 333-351.
Thaller, Peter Helmut, Julian Fürmetz, Florian Wolf, Thorsten Eilers, and Wolf Mutschler. "Limb lengthening with fully implantable magnetically actuated mechanical nails (PHENIX®)—Preliminary results." Injury 45 (2014): S60-S65.
Thompson, George H., Lawrence G. Lenke, Behrooz A. Akbarnia, Richard E. McCarthy, and Robert M. Campbell. "Early onset scoliosis: future directions." The Journal of Bone & Joint Surgery 89, No. suppl 1 (2007): 163-166.
Thonse, Raghuram, John E. Herzenberg, Shawn C. Standard, and Dror Paley. "Limb lengthening with a fully implantable, telescopic, intramedullary nail." Operative Techniques in Orthopaedics 15, No. 4 (2005): 355-362.
Trias, A., P. Bourassa, and M. Massoud. "Dynamic loads experienced in correction of idiopathic scoliosis using two types of Harrington rods." Spine 4, No. 3 (1978): 228-235.
Verkerke, G. J., Koops H. Schraffordt, R. P. Veth, H. J. Grootenboer, L. J. De Boer, J. Oldhoff, and A. Postma. "Development and test of an extendable endoprosthesis for bone reconstruction in the leg." The International journal of artificial organs 17, No. 3 (1994): 155-162.
Verkerke, G. J., H. Schraffordt Koops, R. P. H. Veth, J. Oldhoff, H. K. L. Nielsen, H. H. Van den Kroonenberg, H. J. Grootenboer, and F. M. Van Krieken. "Design of a lengthening element for a modular femur endoprosthetic system." Proceedings of the Institution of Mechanical Engineers, Part H: Journal of Engineering in Medicine 203, No. 2 (1989): 97-102.
Verkerke, G. J., H. Schraffordt Koops, R. P. H. Veth, H. H. van den Kroonenberg, H. J. Grootenboer, H. K. L. Nielsen, J. Oldhoff, and

(56) References Cited

OTHER PUBLICATIONS

A. Postma. "An extendable modular endoprosthetic system for bone tumour management in the leg." Journal of biomedical engineering 12, No. 2 (1990): 91-96.

Wenger, H. L. "Spine Jack Operation in the Correction of Scoliotic Deformity: A Direct Intrathoracic Attack to Straighten the Laterally Bent Spine: Preliminary Report." Archives of Surgery 83, No. 6 (1961): 901-910.

White III, Augustus A., and Manohar M. Panjabi. "The clinical biomechanics of scoliosis." Clinical orthopaedics and related research 118 (1976): 100-112.

Yonnet, Jean-Paul. "A new type of permanent magnet coupling." Magnetics, IEEE Transactions on 17, No. 6 (1981): 2991-2993.

Zheng, Pan, Yousef Haik, Mohammad Kilani, and Ching-Jen Chen. "Force and torque characteristics for magnetically driven blood pump." Journal of Magnetism and Magnetic Materials 241, No. 2 (2002): 292-302.

Brown et al., "Single port surgery and the Dundee Endocone.", SAGES Annual Scientific Sessions: Emerging Technology Poster Abstracts, 2007, ETP007, pp. 323-324.

Weiner, R. et al., "Early Results with a New Telemetrically Adjustable Gastric Banding," Obesity Surgery, 2007, vol. 17, No. 6, pp. 717-721, McGraw-Hill Medical Publishing, New York, U.S.A.

\* cited by examiner

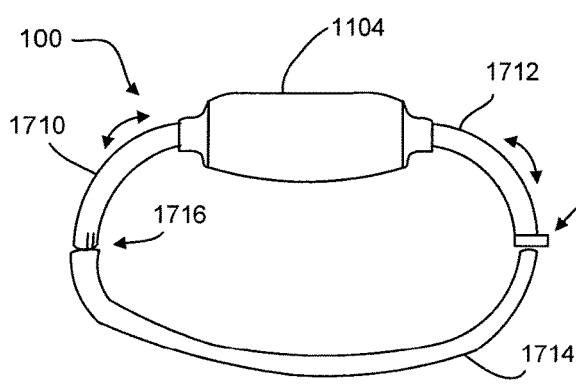
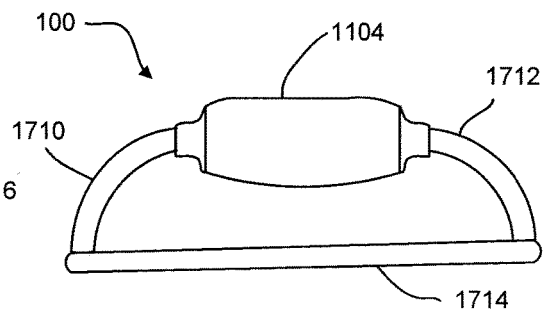
FIG. 17A
FIG. 17B
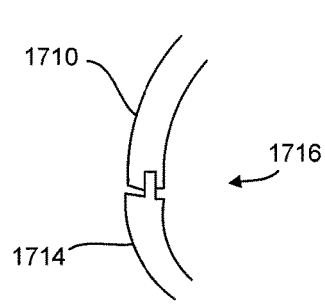
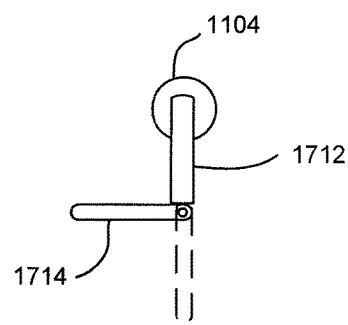
FIG. 17C
FIG. 17D
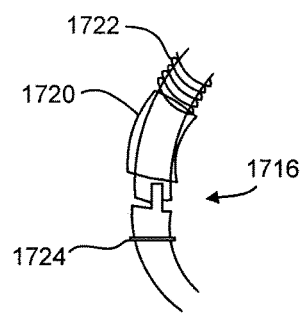
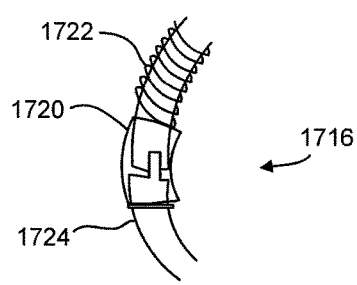
FIG. 17E  FIG. 17F

ADJUSTABLE IMPLANT SYSTEM

RELATED APPLICATIONS

Any and all applications for which a foreign or domestic priority claim is identified in the Application Data Sheet as filed with the present application are hereby incorporated by reference under 37 CFR 1.57.

TECHNICAL FIELD

This application is related to annuloplasty rings. More specifically, this application is related to reversibly adjustable annuloplasty rings.

BACKGROUND

Heart disease and its associated health issues are a large concern today. Mitral valve defects such as regurgitation are often caused by a dilation of the tissue surrounding the valve. This causes the mitral opening to enlarge, which prevents the valve leaflets from sealing properly. This heart condition is commonly treated by sewing a ridged ring around the valve. Cinching the tissue around the ring restores the valve opening to its approximate original size and operating efficiency.

The proper degree of cinching, however, is difficult to determine during open heart surgery. This is because the patient is under general anesthesia, in a prone position, with the chest wide open, and a large incision in the heart. These factors and others affect the ability to test the modified annulus for its therapeutic affect upon mitral valve leaflet coaptation. Even if the cinching is done well, the tissue may continue to change over the patient's lifetime such that the heart condition returns.

SUMMARY

In one embodiment, a system for treating a heart valve includes an adjustable annuloplasty ring configured to be attached to or near a cardiac valve annulus. The adjustable annuloplasty ring includes a tubular body member and one or more adjustable members. The tubular body member and the one or more adjustable members form a ring shape. The adjustable annuloplasty ring also includes an internal magnet within the tubular body member. The internal magnet is configured to rotate in response to a rotating external magnetic field. The internal magnet is coupled to the one or more adjustable members to change a dimension of the ring shape as the internal magnet rotates.

In certain embodiment the internal magnet includes a cylindrical magnet having magnetic poles divided along a plane running the length of the cylinder. Similar external magnets may be used in an external adjustment device that generates the external magnetic field. The internal and external magnets may be permanent magnets. In addition, or in other embodiments, one or more electromagnets may be used. Numerous example embodiments are provided for the adjustable annuloplasty ring and the external adjustment device.

In certain embodiments, a magnetic brake is implanted near a patient's heart. In the absence of the external magnetic field, the magnetic brake prevents the internal magnet from rotating. In the presence the external magnetic field, the magnetic brake allows the internal magnet to rotate.

Additional aspects and advantages will be apparent from the following detailed description of preferred embodiments, which proceeds with reference to the accompanying drawings.

BRIEF DESCRIPTION OF THE DRAWINGS

FIGS. 17A, 17B, 17C, 17D, 17E, and 17F are schematic diagrams of an adjustable annuloplasty ring according to another embodiment.

DETAILED DESCRIPTION OF ILLUSTRATED EMBODIMENTS

An adjustable annuloplasty ring allows for the proper degree of cinching both during open heart surgery and over the patient's lifetime. In one embodiment, an annuloplasty ring may be adjusted less-invasively or non-invasively with the patient alert and postoperatively healed. In addition, the annuloplasty ring incorporates the ability to both open and close with fine position control.

The embodiments disclosed herein are generally directed to adjustable annuloplasty rings for mitral valve repair. However, this disclosure is not limited to the mitral valve and an artisan will recognize from the disclosure herein that the adjustable rings may be adapted for other heart valves (e.g., tricuspid valve, aortic value, and/or pulmonary valve) and other vascular structures.

Overview

Figure 1A:
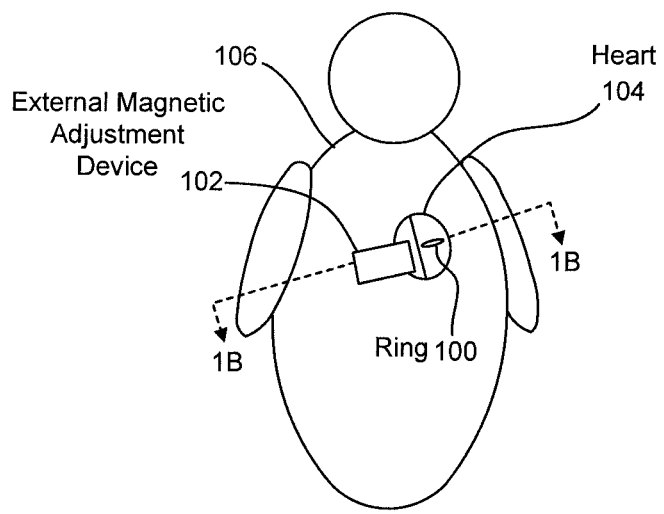
FIG. 1A is a block diagram of a system for adjusting the size of a heart valve according to one embodiment that includes an annuloplasty ring and an external magnetic driver or adjustment device.
Figure 1B:
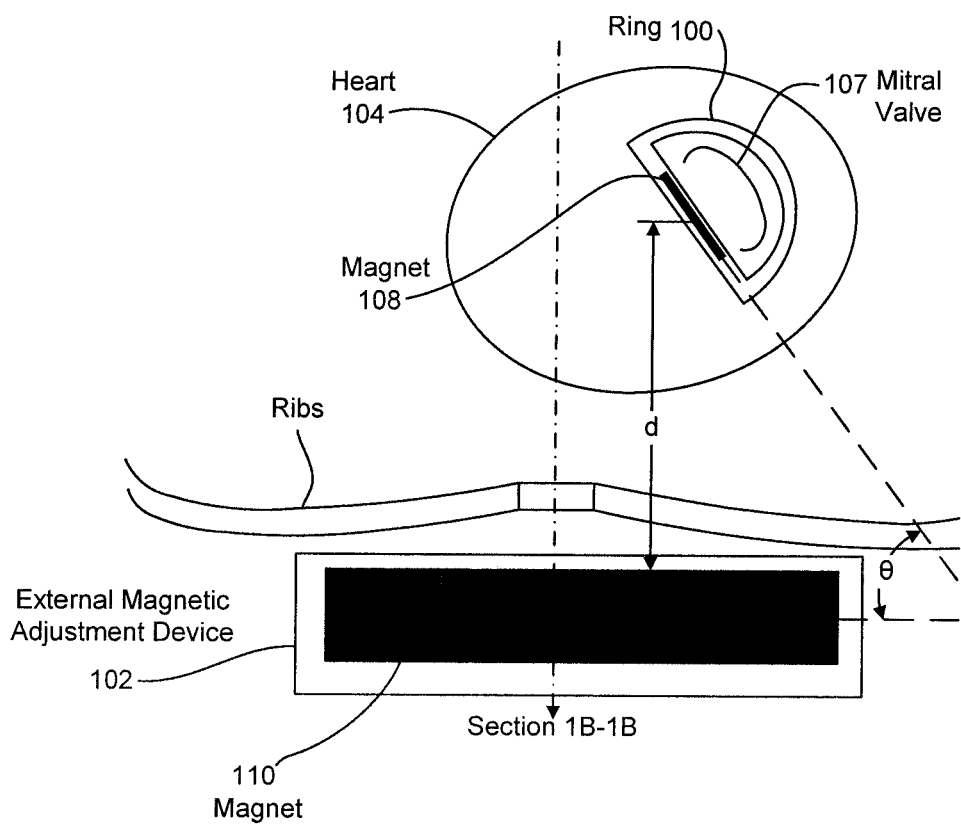
FIG. 1B is an enlarged, cross-sectional view of the annuloplasty ring and the external magnetic adjustment device shown in FIG. 1A according to one embodiment.

FIG. 1A is a block diagram of a system for adjusting the size of a heart valve according to one embodiment that includes an annuloplasty ring 100 and an external magnetic driver or adjustment device 102. For illustrative purposes, FIG. 1B is an enlarged, cross-sectional view of the annuloplasty ring 100 and the external magnetic adjustment device 102 shown in FIG. 1A. The adjustable annuloplasty ring 100 may be implanted in a heart 104 of a patient 106 in the same manner as current rigid annuloplasty rings. Although the heart 104 discussed herein is described in terms of a human heart, an artisan will understand from the disclosure herein that the patient 106 may include any type of mammal or other animal. The annuloplasty ring 100 in this example is "D" shaped and may be attached, for example, to the mitral valve 107. However, an artisan will recognize from the disclosure herein that other shapes (e.g., circular or "C" shaped rings) may also be used for other openings (e.g., for the tricuspid valve).

The annuloplasty ring 100 includes a permanent magnet 108 that may be rotated remotely by one or more magnets 110 in the external magnetic adjustment device 102. Rotating the one or more magnets 110 in the external magnetic adjustment device 102 in one direction causes the annuloplasty ring 100 to close while turning the one or more magnets 110 in the opposite direction causes the annuloplasty ring 100 to open. The external magnetic adjustment device 102 shown in FIGS. 1A and 1B may include an external handpiece that controls the annuloplasty ring 100 from outside of the patient's body at a distance d from the annuloplasty ring 100. However, other adjustment devices (including percutaneous adjustment devices) will also be described in detail below.

In one embodiment, the annuloplasty ring 100 and adjustment device includes one or more of the magnetic adjustment elements disclosed in U.S. Patent Application Publication No. 2008/0097487, titled "Method and Apparatus for Adjusting a Gastrointestinal Restriction Device," filed Jun. 8, 2007, which is assigned to the Assignee of the present application, and which is hereby incorporated by reference herein for all purposes. U.S. Patent Application Publication No. 2008/0097487 discloses a gastrointestinal implant system that includes a magnetically adjustable restriction device having a contact surface configured for at least partially engaging a surface of a gastrointestinal tract of a mammal. The gastrointestinal implant system includes an implantable interface including a driving element, the driving element being moveable and operatively coupled to the adjustable restriction device by an actuator configured to change the dimension or configuration of the contact surface in response to movement of the driving element. Movement of the driving element is effected by application of a moving magnetic field originating external to the patient.

Figure 2A:
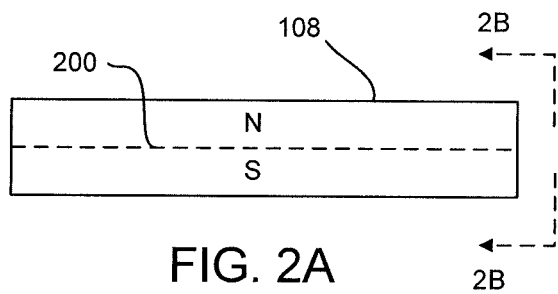
FIGS. 2A and 2B schematically illustrate a magnet that is usable in the annuloplasty ring shown in FIG. 1A according to one embodiment.
Figure 2B:
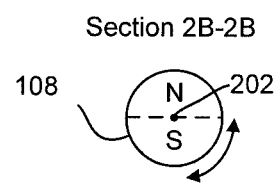

FIGS. 2A and 2B schematically illustrate a magnet 108 that is usable in the annuloplasty ring 100 shown in FIG. 1A according to one embodiment. A similarly configured magnet may also be used for the magnet 110 in the external magnetic adjustment device 102. The magnet 108 in this example embodiment is cylindrical and has magnetic poles (e.g., north "N" and south "S") divided along a plane 200 that runs the length of the cylinder. A rotating magnetic field causes the magnet 108 to rotate around an axis 202 of the cylinder that passes through the respective centers of the cylinder's bases (the "cylindrical axis").

Figure 3A:
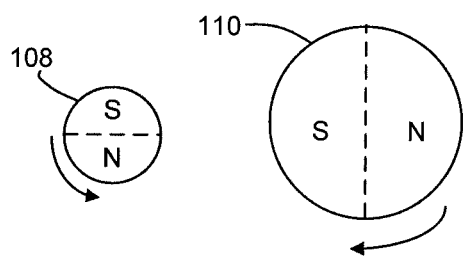
FIGS. 3A and 3B schematically illustrate an end view of the magnet of the external magnetic adjustment device placed in parallel with the magnet of the annuloplasty ring according to certain embodiments.
Figure 3B:
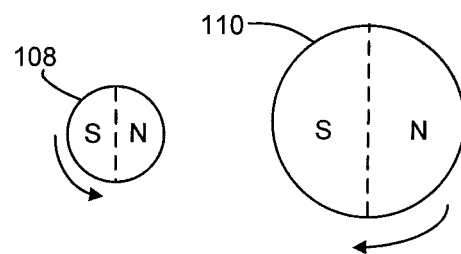

For example, FIGS. 3A and 3B schematically illustrate an end view of the magnet 110 of the external magnetic adjustment device 102 placed in parallel with the magnet 108 of the annuloplasty ring 100 according to certain embodiments. For illustrative purposes, FIG. 3A illustrates the magnets 108, 110 aligned for maximum (peak) torque transmission and FIG. 3B illustrates the south pole of the magnet 110 of the external magnetic adjustment device 102 aligned with the north pole of the magnet 108 of the annuloplasty ring 100. Regardless of a current or initial alignment of the magnets 108, 110, the magnetic fields of the respective magnets 108, 110 interact with each other such that mechanically rotating the magnet 110 (e.g., using a stepper motor) in the external magnetic adjustment device 102 causes the magnet 108 in the annuloplasty ring 100 to rotate. For example, rotating the magnet 110 in a clockwise direction around its cylindrical axis causes the magnet 108 to rotate in a counterclockwise direction around its cylindrical axis. Similarly, rotating the magnet 110 in a counterclockwise direction around its cylindrical axis causes the manet 108 to rotate in a clockwise direction around its cylindrical axis.

The magnet 110 in the external magnetic adjustment device 102 provides accurate one-to-one control of the magnet 108 in the annuloplasty ring 100, assuming sufficient magnetic interaction between the magnets 108, 110. In other words, one complete rotation of the magnet 110 in the external magnetic adjustment device 102 will cause one complete rotation of the magnet 108 in the annuloplasty ring 100. If the relationship between the number of rotations of the magnet 108 and the size of the ring is linear, the size of the annuloplasty ring 108 may be determined directly from the number of revolutions since the ring was at its last known size. If, however, the relationship between the number of revolutions and ring size is not linear, a look-up table based on tested values for a particular ring or type of ring may be used to relate the number of revolutions to the size of the annuloplasty ring 100. Imaging techniques may also be used to determine the ring size after it is implanted in the patient. In addition, or in other embodiments, the annuloplasty ring 100 may include circuitry for counting the number of revolutions or determining its own size, and for communicating this data to a user. For example, the annuloplasty ring 100 may include a radio frequency identification (RF ID) tag technology to power and receive data from the annuloplasty ring 100.

While placing the magnets 108, 110 in parallel increases rotational torque on the magnet 108 in the annuloplasty ring 100, the disclosure herein is not so limited. For example, FIG. 1B illustrates that the cylindrical axis of the magnet 110 in the external magnetic adjustment device 102 may be located at an angle θ with respect to the cylindrical axis of the magnet 108 in the annuloplasty ring 100. The rotational torque on the magnet 108 provided by rotating the magnet 110 increases as the angle θ approaches zero degrees, and decreases as the angle θ approaches 90 degrees (assuming both magnets 108, 110 are in the same geometric plane or in parallel planes).

Figure 4:
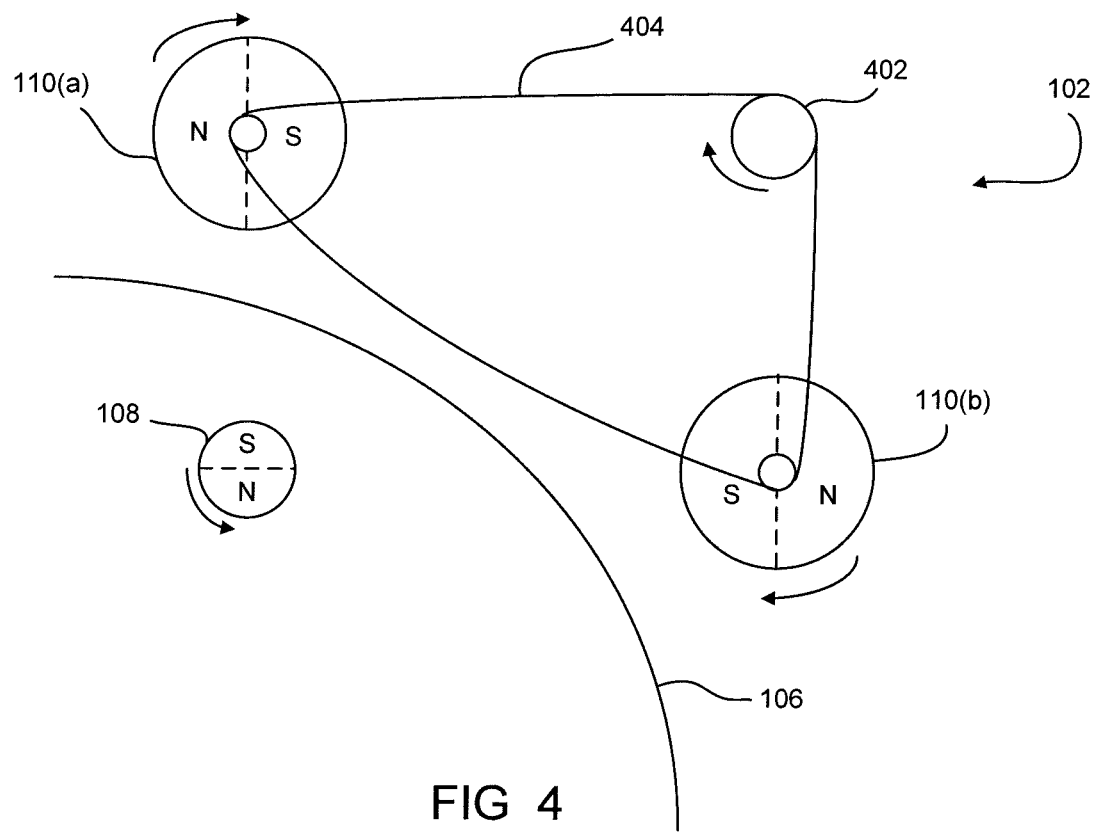
FIG. 4 is a schematic diagram of an external magnet adjustment device including two magnets arranged outside of a patient's body according to one embodiment.

The rotational torque on the magnet 108 in the annuloplasty ring 100 also increases by using magnets 108, 110 with stronger magnetic fields and/or by increasing the number of magnets used in the external magnetic adjustment device 102. For example, FIG. 4 is a schematic diagram of an external magnetic adjustment device including two magnets 110(a), 110(b) arranged outside of a patient's body 106 according to one embodiment. An artisan will recognize from the disclosure herein that the external magnetic adjustment device 102 is not limited to one or two magnets, but may include any number of magnets. For example, an example embodiment that includes four magnets is described below with respect to FIG. 28. The magnets 110(a), 110(b) are oriented and rotated relative to each other such that their magnetic fields add together at the ring magnet 108 to increase rotational torque. A computer controlled motor 402 synchronously rotates the external magnets 110(a), 110(b) through a mechanical linkage 404 to magnetically rotate the internal magnet 108 and adjust the size of the annuloplasty ring 100. One revolution of the motor 402 causes one revolution of the external magnets 110(a), 110(b), which in turn causes one revolution of the ring magnet 108. As discussed above, by counting motor revolutions, the size of the annuloplasty ring 100 may be calculated. In one embodiment, the motor 402 includes a gearbox with a known gear ratio such that multiple motor revolutions may be counted for one magnet revolution.

In another embodiment, a strong electro-magnetic field like that used in Magnetic Resonance Imaging (MRI) is used to adjust the annuloplasty ring 100. The magnetic field may be rotated either mechanically or electronically to cause the magnet 108 in the annuloplasty ring 100 to rotate. The patient's body may also be rotated about the axis 202 of the magnet 108 in the presence of a strong magnetic field, like that of an MRI. In such an embodiment, the strong magnetic field will hold the magnet 108 stationary while the ring 100 and patient 106 are rotated around the fixed magnet 108 to cause adjustment. The ring size may be determined by counting the number of revolutions of the magnetic field, or the patient's body, similar to counting revolutions of the permanent magnets 110 discussed above.

In another embodiment, the annuloplasty ring 100 may be adjusted during open heart surgery. For example, after implanting the annuloplasty ring 100 in the heart 104, the heart 104 and pericardium may be closed, and the regurgitation monitored (e.g., using ultrasound color Doppler). Then, a user (e.g., surgeon) may use a handheld adjustment device 102 to resize the annuloplasty ring based on the detected regurgitation. Additional regurgitation monitoring and ring adjustment may be performed before completing the surgery.

Figure 5A:
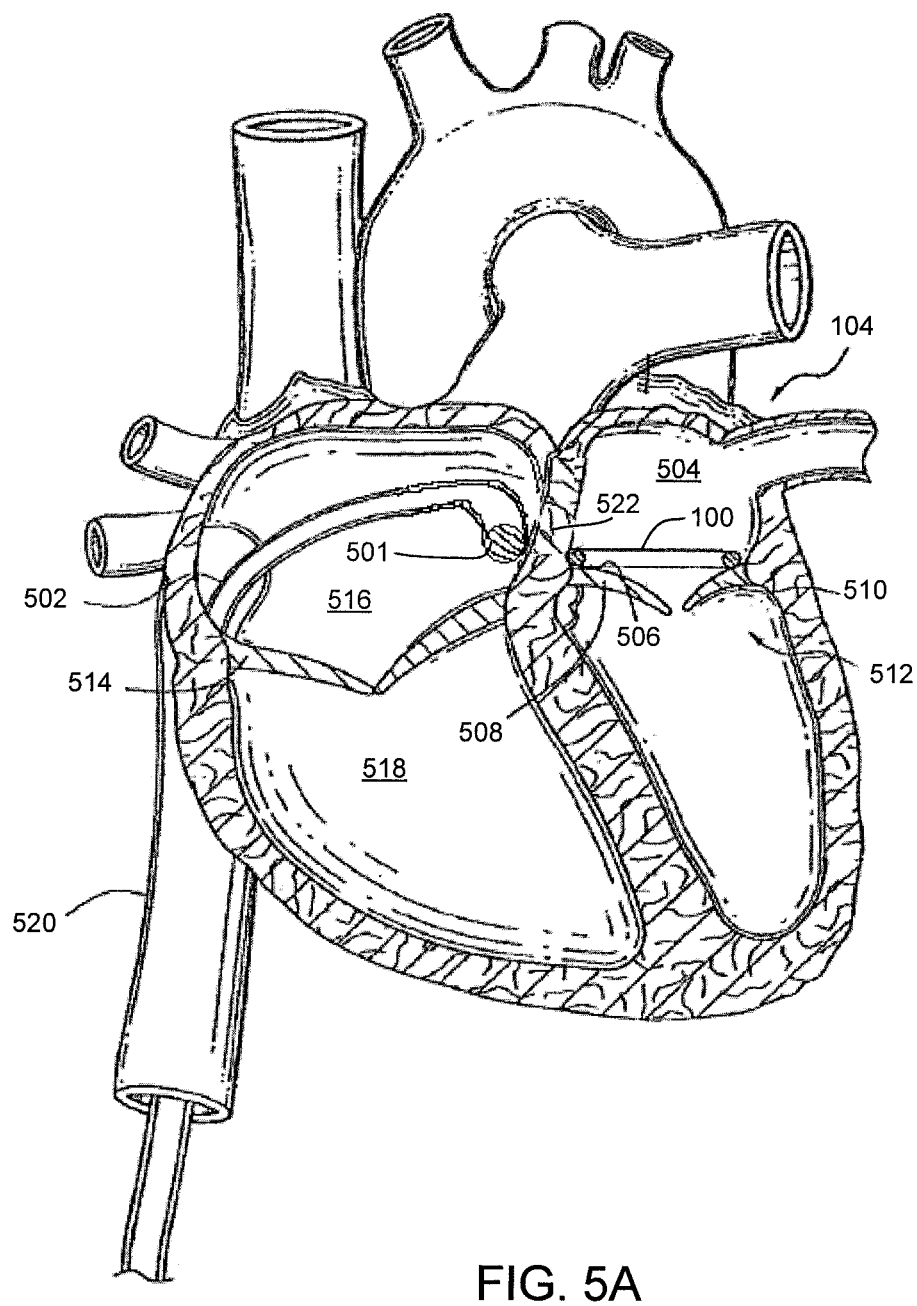
FIGS. 5A and 5B schematically illustrate a catheter system used to insert an adjustment device into a patient's heart according to certain embodiments.
Figure 5B:
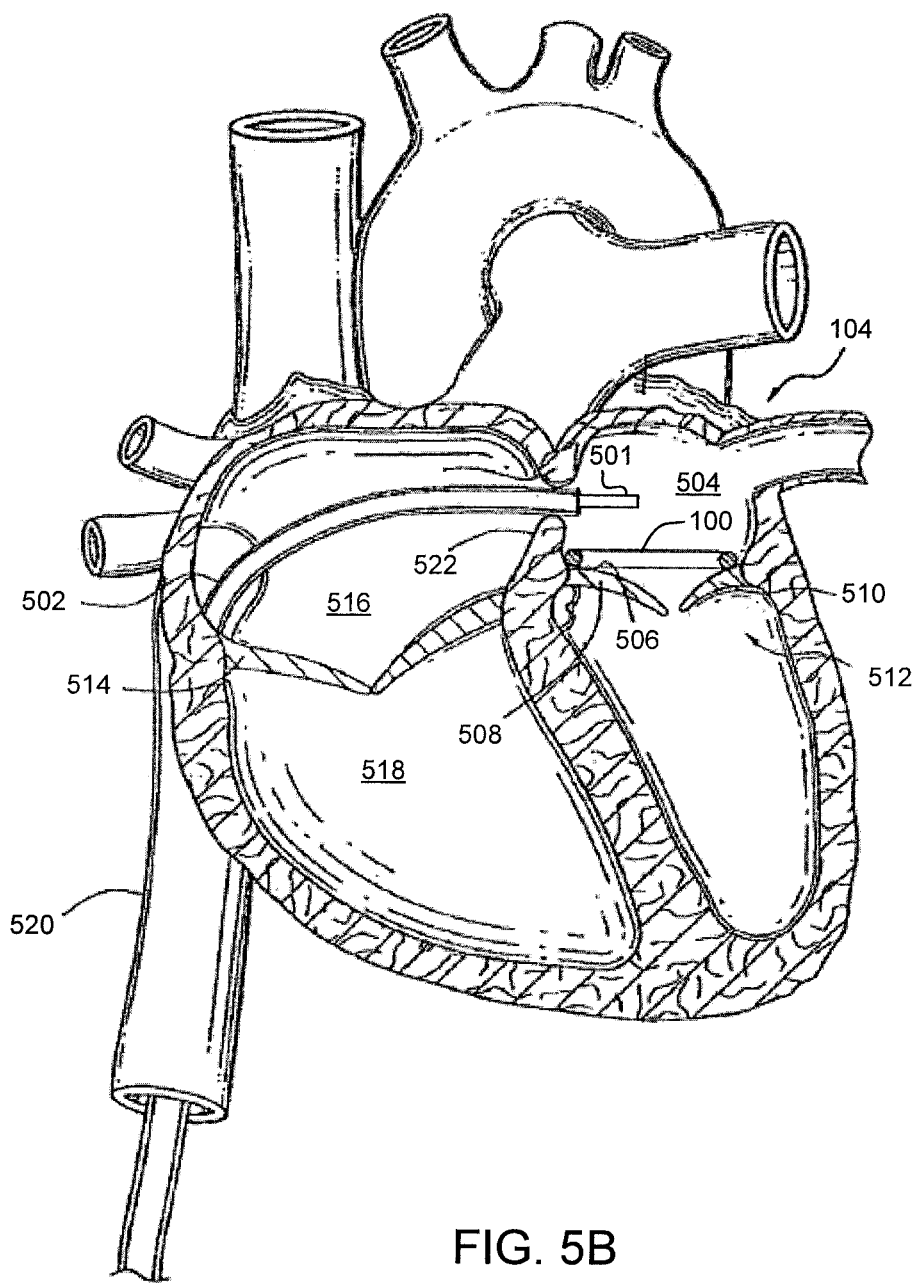

In another embodiment, a percutaneously delivered adjustment device is used to resize the annuloplasty ring 100. For example, FIGS. 5A and 5B schematically illustrate a catheter system 502 used to insert an adjustment device 501 into a patient's heart 104 according to certain embodiments. As shown, the annuloplasty ring 100 may be implanted in the left atrium 504 of the heart 104 on the upper side 506 of the leaflets 508 of the mitral valve 510. However, it is contemplated that the annuloplasty ring 100 may be positioned on the lower side of the leaflets 508. For example, the annuloplasty ring 100 may be positioned in the left ventricle 512. In some non-limiting embodiments, the annuloplasty ring 100 is snaked through the chordae tendineae and then placed against the lower surfaces of the leaflets 508. Alternatively, the chordae tendineae may be cut to provide a delivery path for implantation of the annuloplasty ring 100. In certain embodiments, the annuloplasty ring 100 may be implanted at other locations in the vasculature system, or at any other position within a patient's body 106. For example, the annuloplasty ring 100 may be implanted at a location proximate to the tricuspid valve 514. The annuloplasty ring 100 may be positioned on the upper side (e.g., in the right atrium 516) or lower side (e.g., in the right ventricle 518) of the tricuspid valve 514 to improve the efficacy of the tricuspid valve 514.

As shown in FIG. 5A, the catheter system 502 enters the heart 104 through the inferior vena cava 520 into the right atrium 516 so as to position the adjustment device 501 proximate the interatrial septum 522. The catheter system 502 may alternatively enter from the superior vena cava. As discussed above, the adjustment device 501 includes one or more magnets configured to interact with a magnetic field of a magnet in the annuloplasty ring 100. The catheter system 502 is configured to adjust the size of the annuloplasty ring 100 through the interatrial septum 522 by rotating the one or more magnets in the adjustment device 501 using a flexible drive shaft connected to an external hand crank operated by a user (e.g., physician) or a processor-controlled motor.

As shown in FIG. 5B, the catheter system 502 in another embodiment may enter the heart 104 through the inferior vena cava 520 into the right atrium 516, and through a hole (e.g., through the fossa ovalis) in the interatrial septum 522 into the left atrium 504. The catheter system 502 may alternatively enter from the superior vena cava. Although not shown in FIG. 5B, the catheter system 502 may locate the adjustment device 501 proximate the magnet in the annuloplasty ring 100. As discussed above, the adjustment device 501 includes one or more magnets configured to interact with a magnetic field of the magnet in the annuloplasty ring 100. The catheter system 502 is configured to adjust the size of the annuloplasty ring 100 by rotating the one or more magnets in the adjustment device 501 using a flexible drive shaft connected to an external hand crank operated by a user (e.g., physician) or a processor controlled motor.

Figure 6:
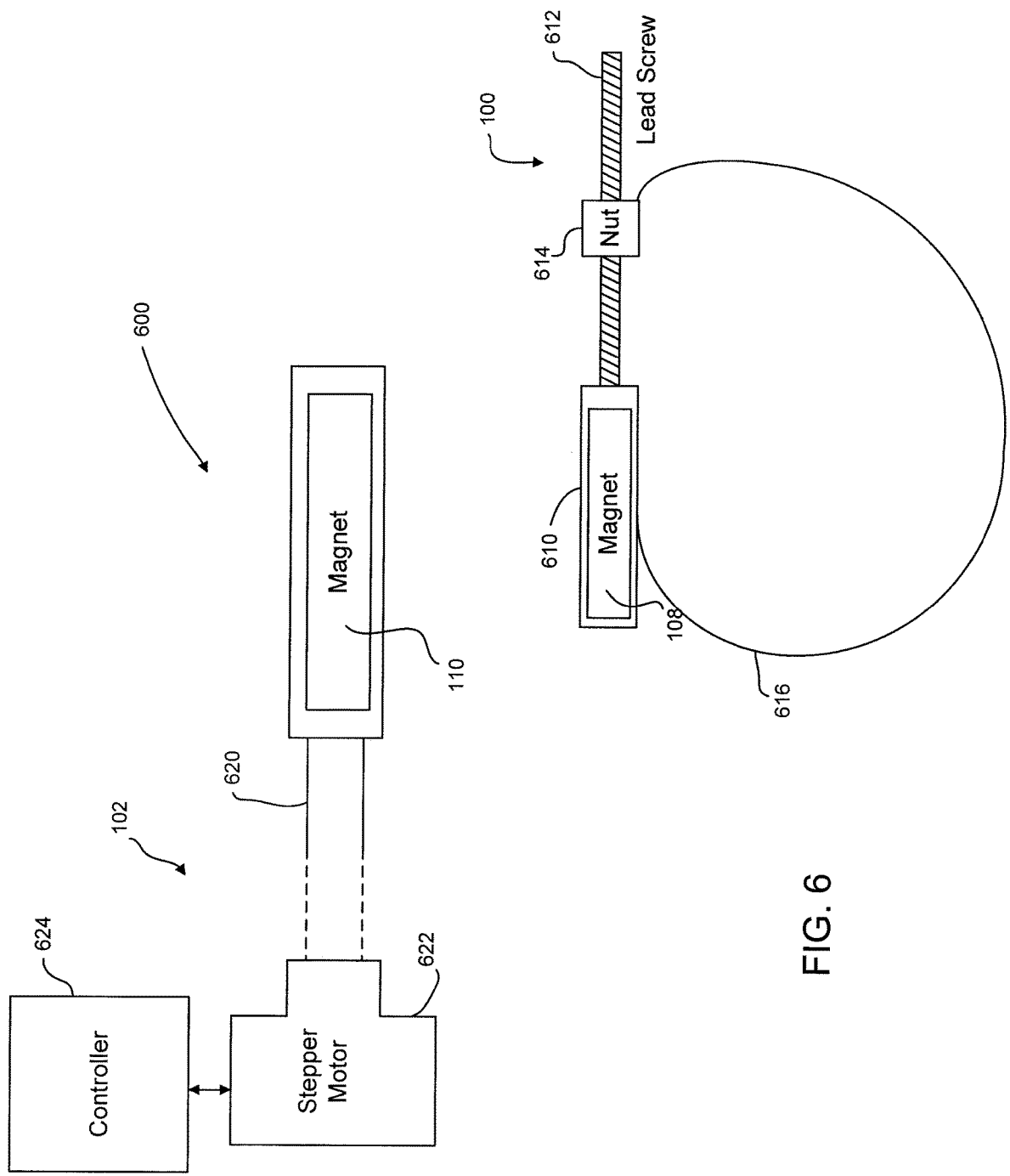
FIG. 6 is a simplified block diagram of a system for adjusting the size of a heart valve according to one embodiment.

FIG. 6 is a simplified block diagram of a system 600 for adjusting the size of a heart valve according to one embodiment. The simplified embodiment shown in FIG. 6 is provided to illustrate the basic operation of the annuloplasty ring 100. However, more detailed embodiments are provided below.

The system 600 includes an adjustable annuloplasty ring 100 and an external magnetic adjustment device 102. The annuloplasty ring 100 includes a magnet 108 in a magnet housing 610. The magnet 108 is cylindrical and is configured to rotate around its cylindrical axis when exposed to a rotating magnetic field. The magnet 108 is coupled to a proximal end of a lead screw 612. A spindle nut 614 is threaded onto the lead screw 612. A wire 616 is coupled to the magnet housing 610 and the spindle nut 614 to form a loop. The wire 616 may include, for example, stainless steel or superelastic nitinol.

The external magnetic adjustment device 102 includes a magnet 110 in a magnet housing 618 coupled to a drive shaft 620. The drive shaft 620 may be connected to a stepper motor 622 coupled to a motor controller/drive 624. The controller/drive 624 may include, for example, a microprocessor or personal computer. The controller/drive 624 is configured to control the position, rotation direction, rotation speed, speed ramp up/down, and other parameters of the stepper motor 622. The stepper motor 622 rotates the shaft 620, which in turn rotates the magnet 110. As discussed above, in certain embodiments the shaft 620 and the magnet 110 may be covered with a protective material (e.g., plating) and inserted into the heart 104 through a catheter.

In operation, the rotating magnet 110 in the external magnetic adjustment device 102 causes the magnet 108 in the annuloplasty ring 100 to rotate. The notating magnet 108 causes the lead screw 612 to rotate, which in turn causes the spindle nut 614 to move along the threads of the lead screw 612 to either increase or decrease the size of the loop formed by the wire 616.

Figure 7:
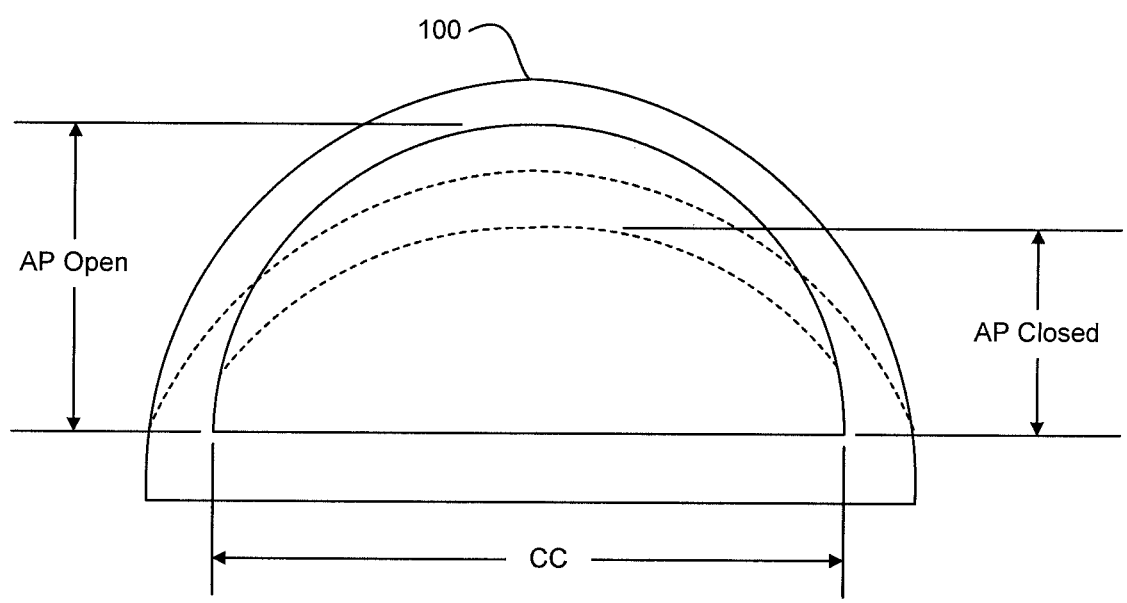
FIG. 7 is a schematic diagram of an adjustable annuloplasty ring according to one embodiment.

In certain embodiments, it is desirable to symmetrically adjust the size of the annuloplasty ring 100 in an anterior/posterior (AP) direction. For example, FIG. 7 is a schematic diagram of an adjustable annuloplasty ring according to one embodiment. The annuloplasty ring 100 is "D" shaped having an AP dimension along the curved portion of the "D" and a commissure to commissure or "CC" dimension along the straight portion of the "D." Adjusting the annuloplasty ring 100 from an open to a closed position, or vice versa, changes the AP dimension without substantially changing the CC dimension. Further, the AP dimension changes symmetrically in that both the left and right sides of the annuloplasty ring 100 change by substantially the same amount. Certain of the following embodiments include these features.

Example Annuloplasty Ring Embodiments

In certain embodiments discussed herein, including those discussed above as well as those discussed below, the materials of the annuloplasty ring 100 are selected for compatibility with long-term contact with human tissue. For example, these materials may include nitinol, stainless steel, titanium alloys, cobalt alloys, bio-compatible plastics, and other bio-compatible materials. In certain embodiments, the annuloplasty ring 100 may be covered with a polyester or Dacron® fabric or other suturable material. In addition or in other embodiments, the annuloplasty ring 100 may also include eyelets used for suturing. The magnet 108 discussed in certain embodiments herein may include a rare-earth magnet and may be plated (e.g., with nickel or gold) or encapsulated in a suitable bio-compatible material, such as the materials discussed above, to reduce or prevent harm to the patient and damage to the magnet. Bearings are included in certain embodiments. These bearings may be of any suitable type including, for example, ball bearings or jewel bearings.

Figure 8A:
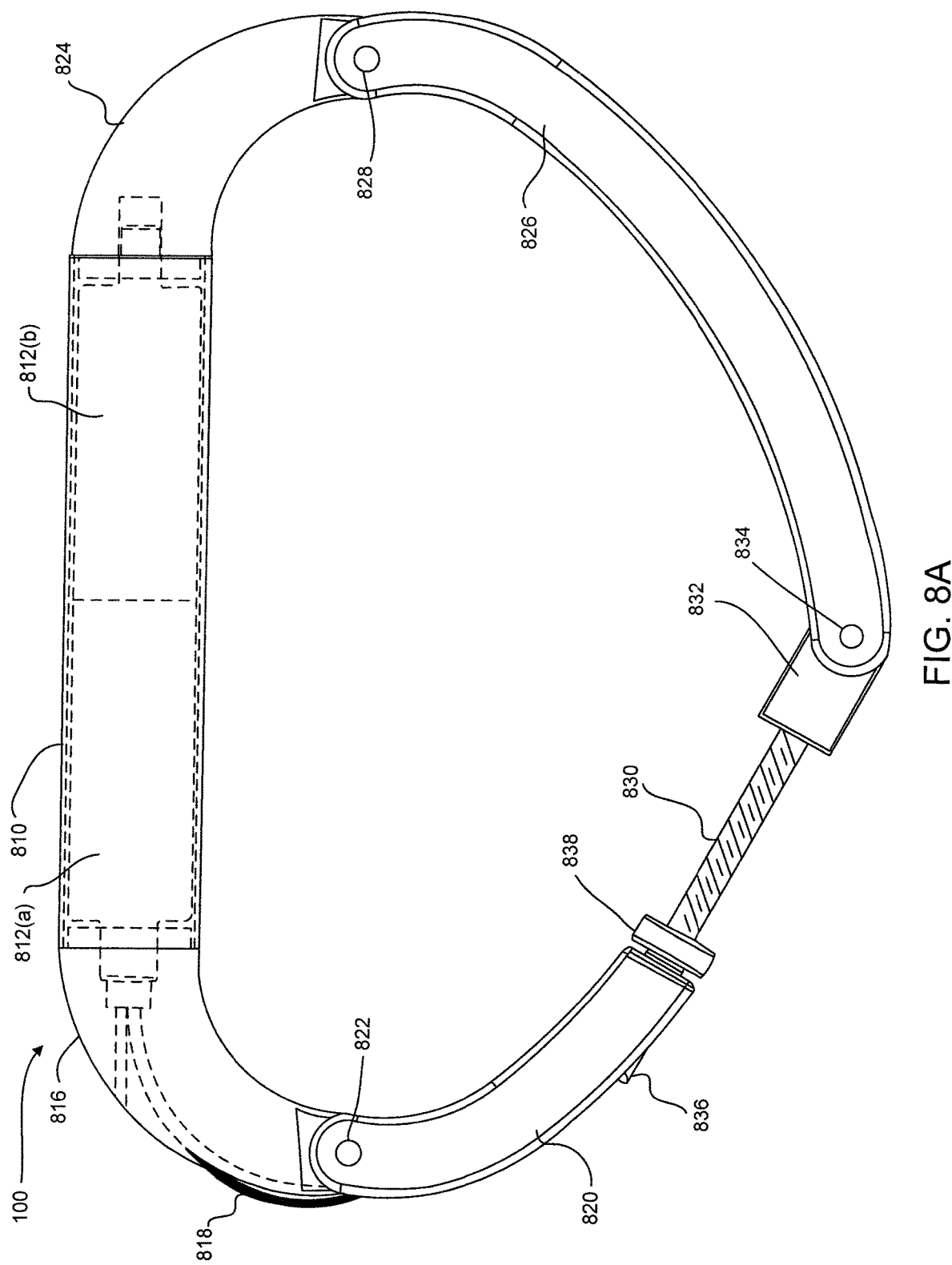
FIGS. 8A 8B, 8C 8D, and 8E schematically illustrate an annuloplasty ring according to one embodiment.
Figure 8B:
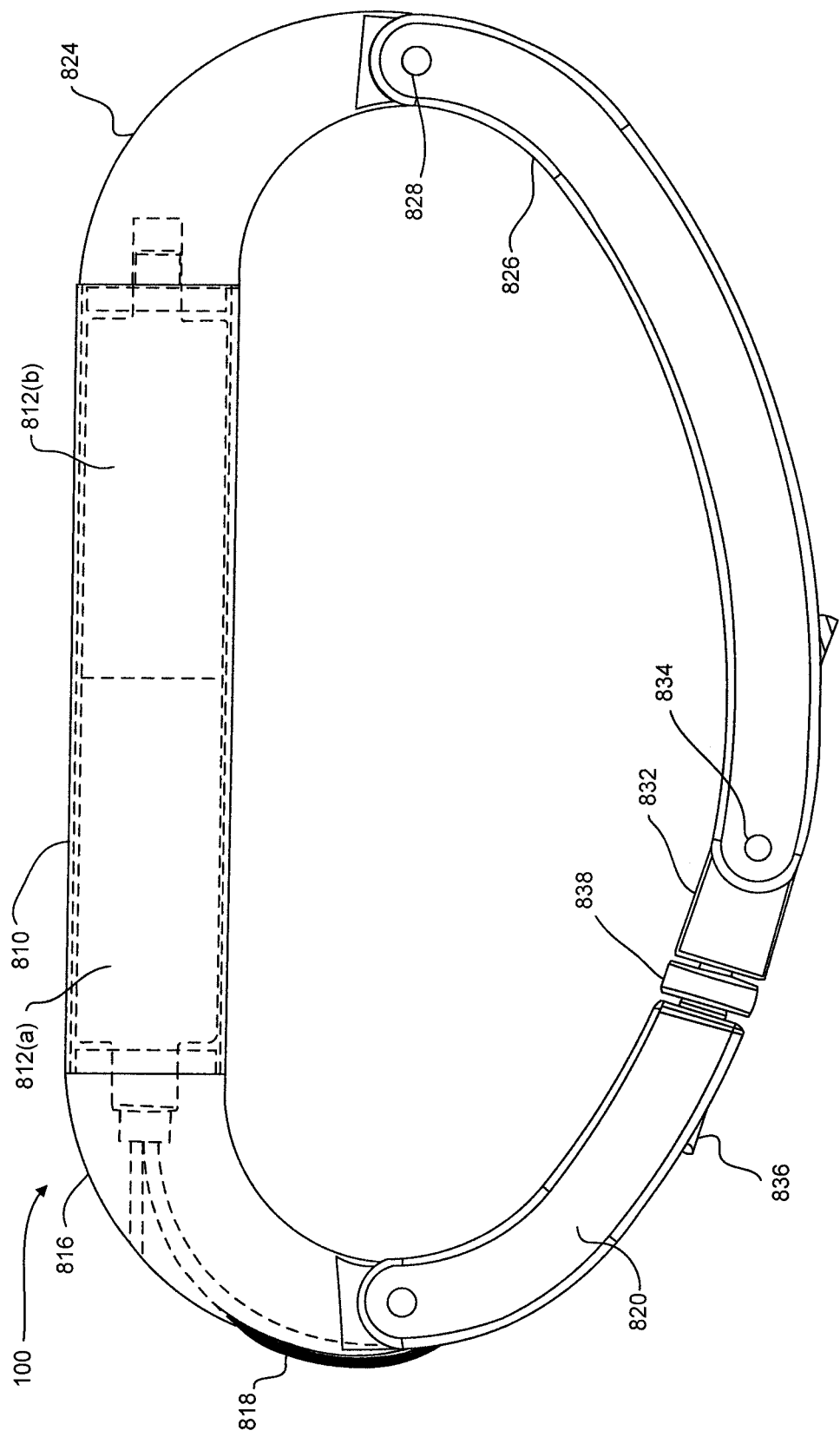
Figure 8C:
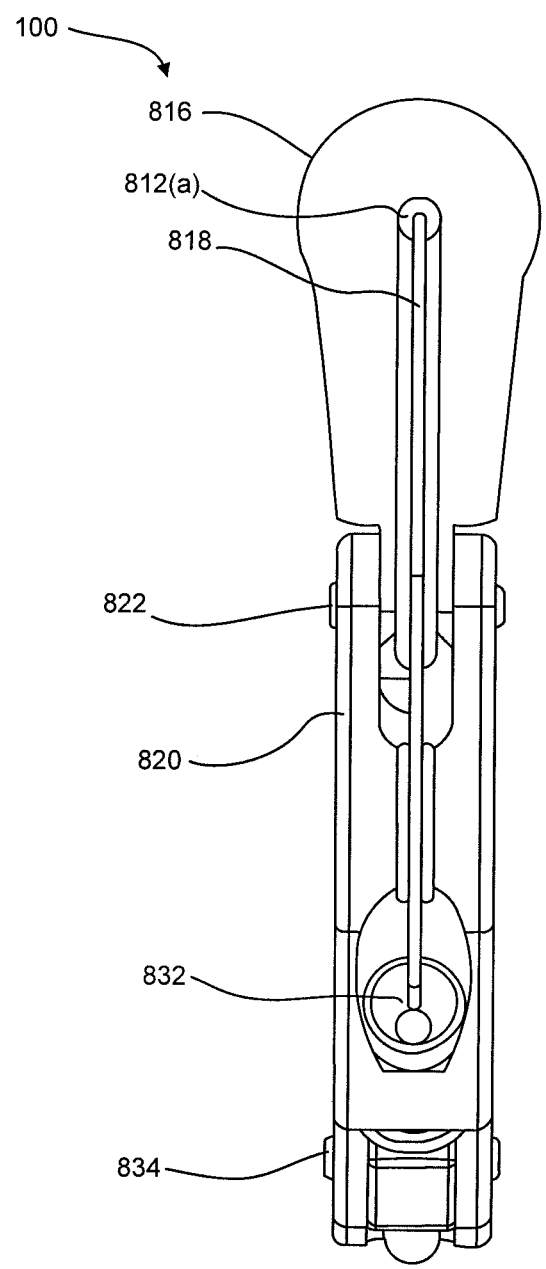
Figure 8D:
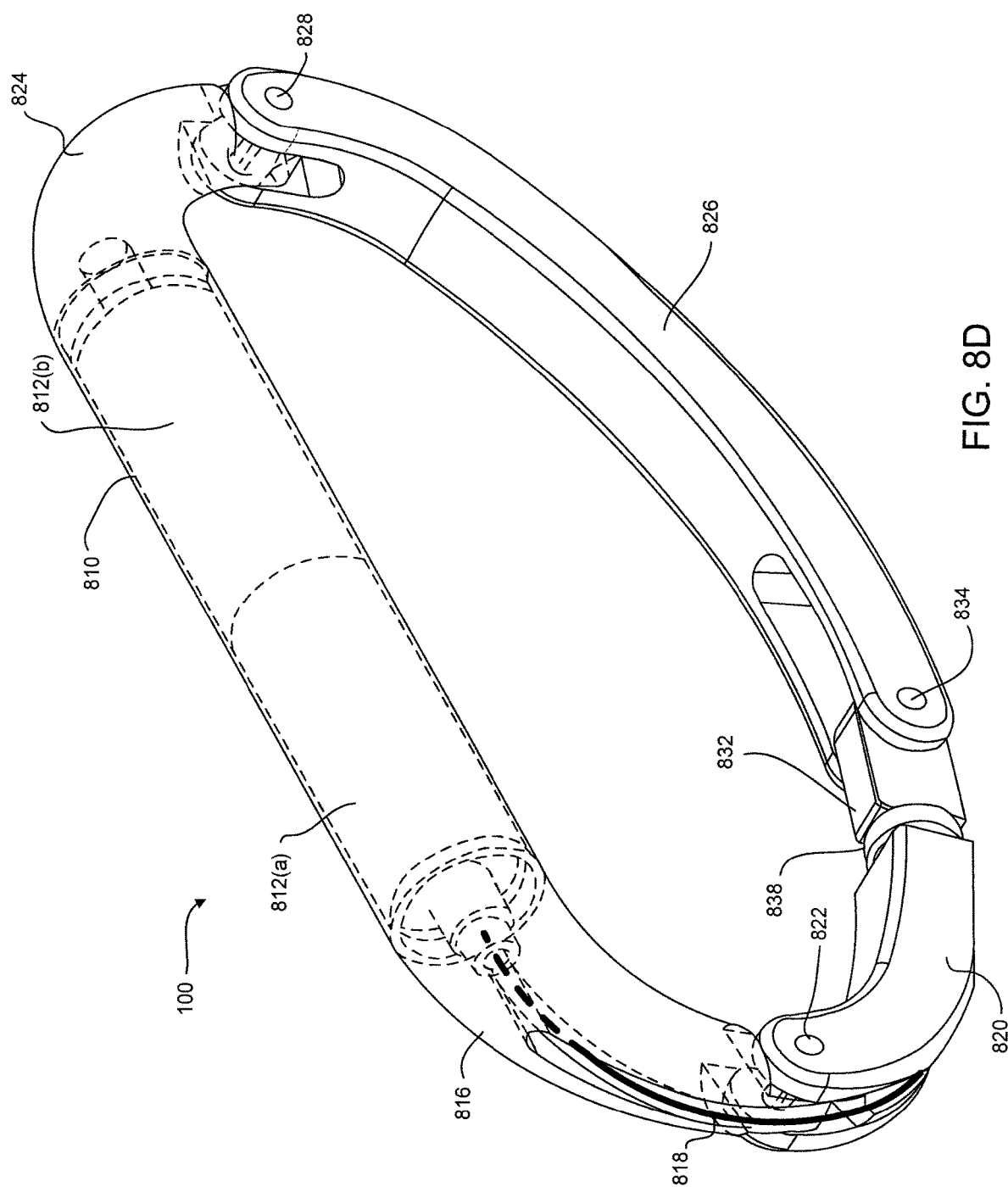
Figure 8E:
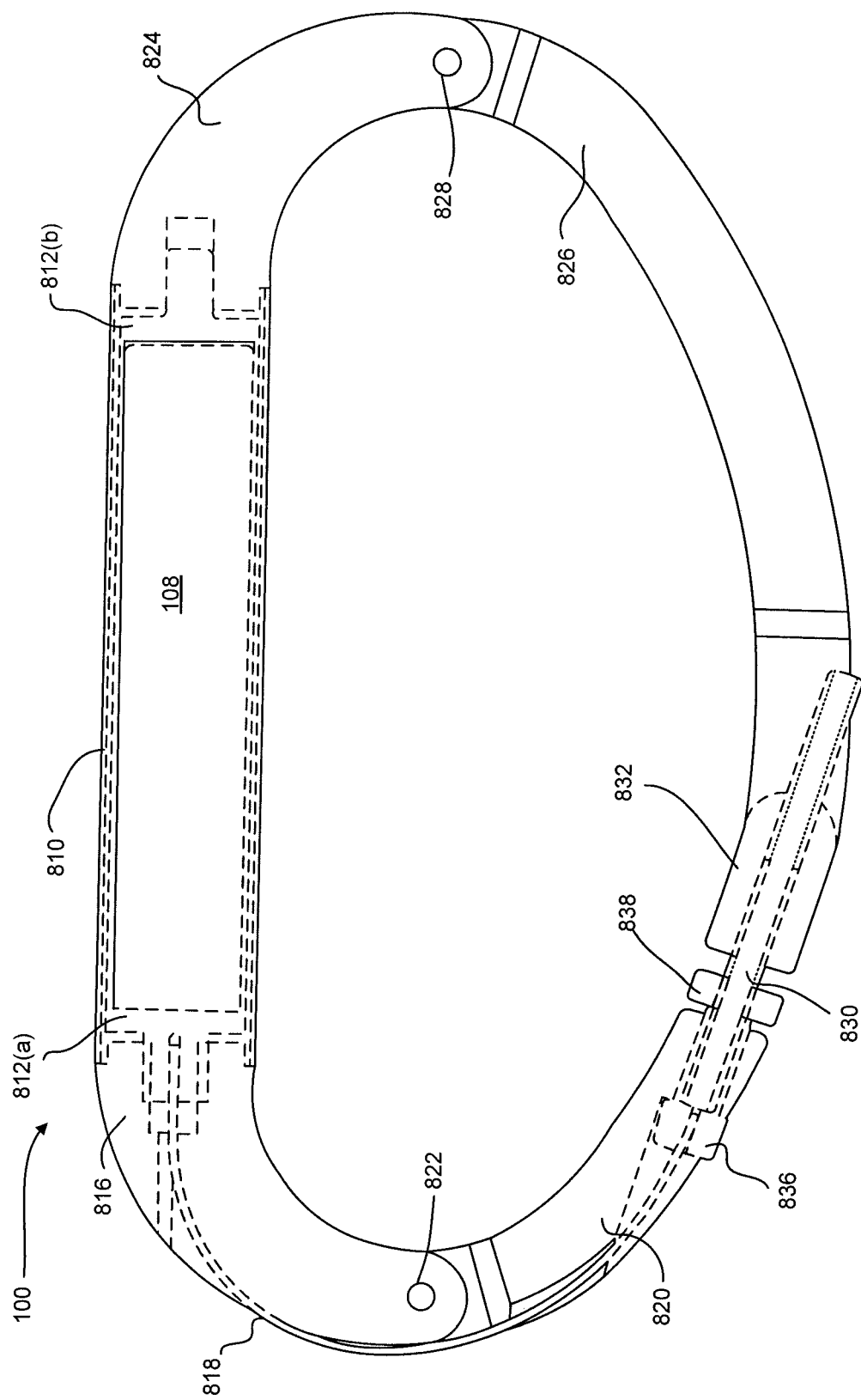

FIGS. 8A, 8B, 8C, 8D, and 8E schematically illustrate an annuloplasty ring 100 according to one embodiment. FIG. 8A is a partially transparent top view of the annuloplasty ring 100 in an AP extended or plus position. FIG. 8B is a partially transparent top view of the annuloplasty ring 100 in an AP retracted or minus position. FIG. 8C schematically illustrates a side view of the annuloplasty ring 100. FIG. 8D is a partially transparent perspective view of the annuloplasty ring 100. FIG. 8E is another partially transparent top view of the annuloplasty ring 100.

The annuloplasty ring 100 includes a body tube 810 for enclosing a magnet housing 812 (including a first end 812(a) and a second end 812(b)) that encases a magnet 108 (FIG. 8E). A first end of the body tube 810 is connected to a first fixed arm 816 and a first end of the magnet housing 812(a) crimps to a first end of a drive cable 818. The first fixed arm 816 is connected to a first swivel arm 820 at a first pin joint 822 (e.g., pivot point). A second end of the body tube 810 is connected to a second fixed arm 824 that is connected to a second swivel arm 826 at a second pin joint 828. The annuloplasty ring 100 also includes a lead screw 830 having a first end threaded into a drive nut 832 that is connected to the second swivel arm 826 at a third pin joint 834. A second end of the lead screw is connected to a drive spindle 836 that is connected to a second end of the drive cable 818. A spindle nut 838 is threaded onto the lead screw 830. The spindle nut 838 retains the drive spindle 836 into the first swivel arm 820.

The magnet housing 812 is engaged with the first fixed arm 816 and the second fixed arm 824 such that rotating the magnet 108 (e.g., using the external magnetic adjustment device 102) causes the magnet housing 812 to rotate. The rotating magnet housing 812 turns the drive cable 818, which turns the drive spindle 836. The drive spindle 836 rotates the lead screw 830 such that it screws into or out of the drive nut 832. As the lead screw 830 screws into or out of the drive nut 832, the swivel arms 820, 826 pivot at their respective pin joints 822, 828, 834 to reduce or enlarge the size of the ring opening in the AP dimension.

Figure 9:
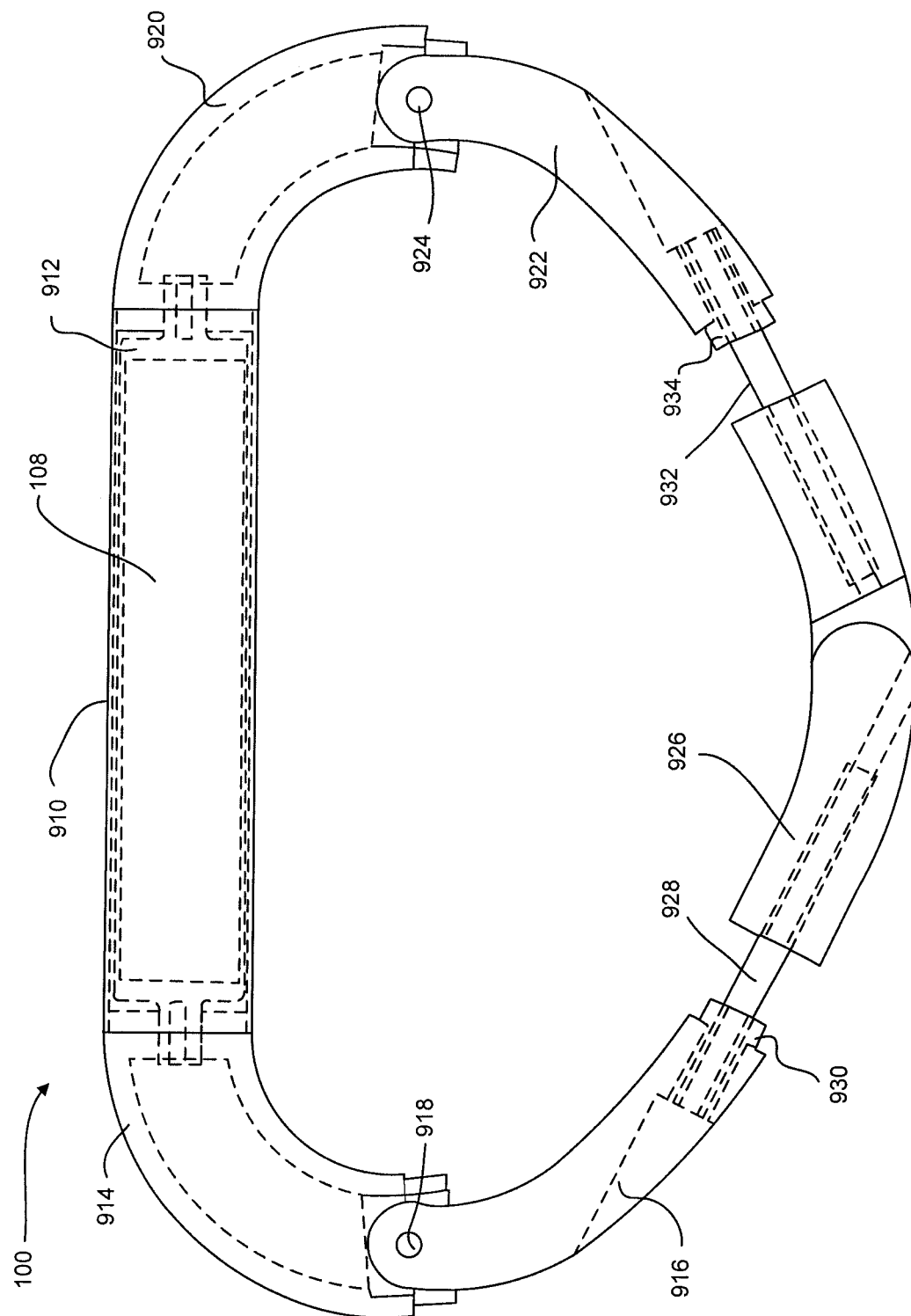
FIG. 9 is a schematic diagram illustrating a partially transparent top view of an annuloplasty ring according to another embodiment.

FIG. 9 is a schematic diagram illustrating a partially transparent top view of an annuloplasty ring 100 according to another embodiment. The annuloplasty ring 100 shown in FIG. 9 includes a body tube 910 for enclosing a magnet housing 912 that encases a magnet 108. A first end of the body tube 910 is connected to a first fixed arm 914 and a first end of the magnet housing 912 crimps to a first end of a first drive cable (not shown). The first fixed arm 914 is connected to a first swivel arm 916 at a first pin joint 918. A second end of the body tube 910 is connected to a second fixed arm 920 and a second end of the magnet housing 912 crimps to a first end of a second drive cable (not shown). The second fixed arm 920 is connected to a second swivel arm 922 at a second pin joint 924.

The annuloplasty ring 100 also includes an extension 926 that symmetrically moves in and out in the AP dimension as the magnet 108 turns. A first end of a first lead screw 928 is connected to the first swivel arm 916 through a first drive spindle 930 that is connected to the second end of the first drive cable. A second end of the first lead screw 928 is threaded into a first end of the extension 926. A first end of a second lead screw 932 is connected to the second swivel arm 922 through a second drive spindle 934 that is connected to the second end of the second drive cable. A second end of the second lead screw 932 is threaded into a second end of the extension 926. The extension 926 acts as a drive nut for a first lead screw 928 and the second lead screw 932. The first lead screw 928 and the second lead screw 932 both screw into or out of the extension 926 at the same time, causing the swivel arms 916, 922 to pivot about their respective pin joints 918, 924. In such an embodiment, one of the lead screws 928, 932 has "right handed" threads and the other has "left-handed" threads such that both lead screws 928, 932 tighten or loosen together.

Figure 10:
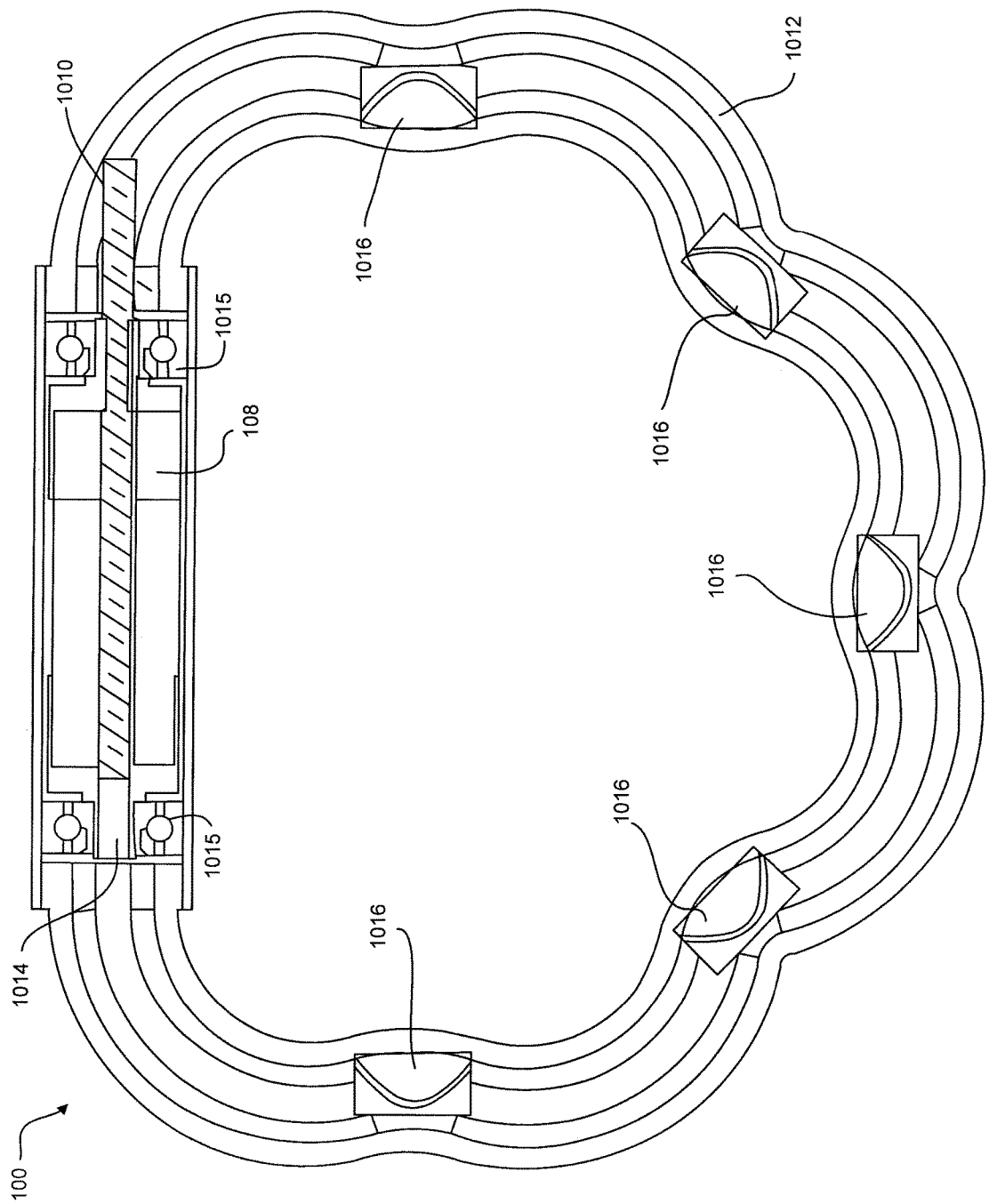
FIG. 10 is a schematic diagram illustrating a cross-sectional top view illustrating an annuloplasty ring according to another embodiment.

FIG. 10 is a schematic diagram illustrating a cross-sectional top view illustrating an annuloplasty ring 100 according to another embodiment. The annuloplasty ring 100 shown in FIG. 10 includes a magnet 108, a flexible lead screw 1010, an elastic covering 1012, and a wire (not shown) extending from a first end of the flexible lead screw 1010 to a fixed point. The elastic covering 1012 may include, for example, a biocompatible polymer such as, for instance, polyurethane silicone or a silicone-urethane copolymer. The magnet 108 includes a hollow passage 1014 and a threaded nut section 1015 or bearings through which the flexible lead screw 1010 passes (e.g., either to the right or to the left) as the magnet 108 turns. Turning the magnet 108 in one direction exerts force on the flexible lead screw 1010, which is transmitted to the wire, which in turn causes the elastic covering 1012 to contract inwardly at predetermined locations 1016. The contraction symmetrically reduces the ring opening. Rotating the magnet 108 in the opposite direction reverses the contraction.

Figure 11A:
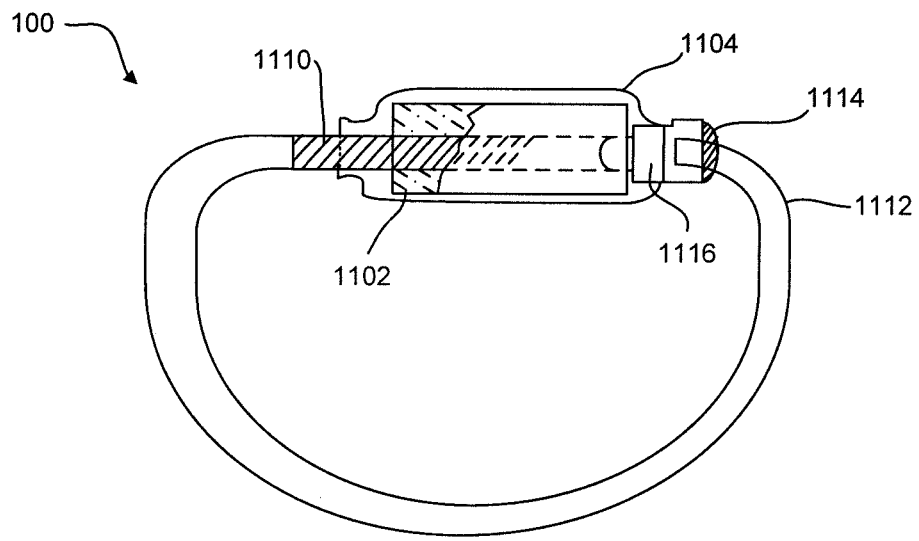
FIGS. 11A, 11B, and 11C are schematic diagrams of an adjustable annuloplasty ring according to another embodiment.
Figure 11B:
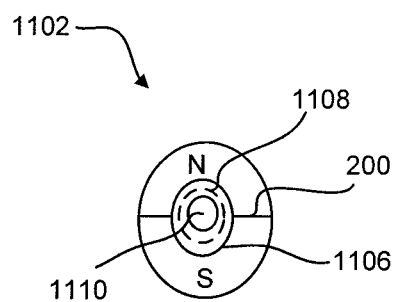
Figure 11C:
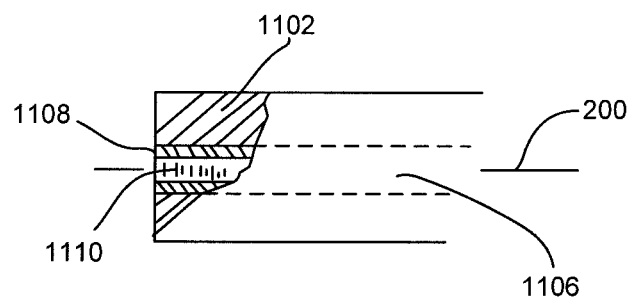

FIG. 11A is a schematic diagram of an adjustable annuloplasty ring 100 according to another embodiment. The annuloplasty ring 100 includes a permanent magnet 1102 configured to rotate within a magnet housing 1104. The magnet 1102 is cylindrical and is configured to rotate around its cylindrical axis when exposed to a rotating magnetic field. FIG. 11B is a schematic diagram of a front view of the magnet 1102 shown in FIG. 11A according to one embodiment. FIG. 11C is a schematic diagram of a side view of the magnet 1102 shown in FIG. 11A according to one embodiment. Like the magnet 108 shown in FIGS. 2A, 2B, 4, and 6, the magnet 1102 has magnetic poles (e.g., north "N" and south "S") divided along the plane 200 that runs the length of the cylinder. The magnet 1102 may include a rare earth magnet and may be plated (e.g., with nickel or gold) and/or suitably encapsulated to prevent harm to the patient and damage to the magnet 1102. Unlike the magnet 108 shown in FIGS. 2A, 2B, 4, and 6, however, the magnet 1102 includes a hollow region 1106 running along the length of the cylinder between the N and S pores. The hollow region 1106 may be threaded or may contain a threaded insert 1108 through which a lead screw 1110 is pulled into and out of the magnet 1102.

A wire 1112 is coupled between the magnet housing 1104 (e.g., by a weld 1114) and an end of the lead, screw 1110. In another embodiment, a separate lead screw 1110 is not used. Rather, threads are formed or cut into the end of the wire 1112 such that the wire 1112 interfaces directly with the threads in the magnet 1102 (e.g., the threaded insert 1108). The wire 1112 may include, for example, superelastic In one embodiment, the annuloplasty ring 100 includes bearings 1116 to anchor the spinning magnet 1102. When the magnet 1102 is exposed to a rotating magnetic field in one direction, the magnet 1102 pulls the lead screw 1110 and/or threaded wire 1112 into the magnet 1102, which in turn reduces the size of the loop formed by the wire 1112. When the magnet 1102 is exposed to the magnetic field rotating in the opposite direction, the magnet 1102 pushes the lead screw 1110 and/or the threaded wire 1112 out of the magnet 1102, which in turn increases the size of the loop formed by the wire 1112.

Figure 12B:
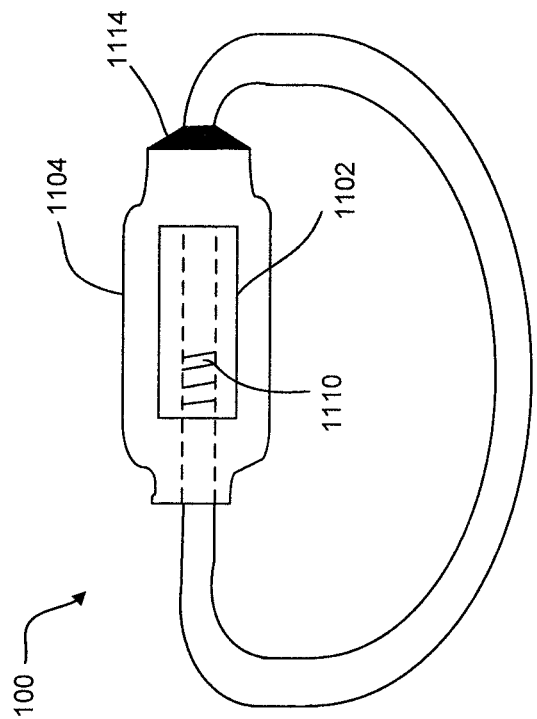
FIGS. 12A and 12B partially illustrate the annuloplasty ring shown in FIG. 11A in a retracted position (FIG. 12A) and in an expanded position (FIG. 12B) according to certain embodiments.
Figure 12A:
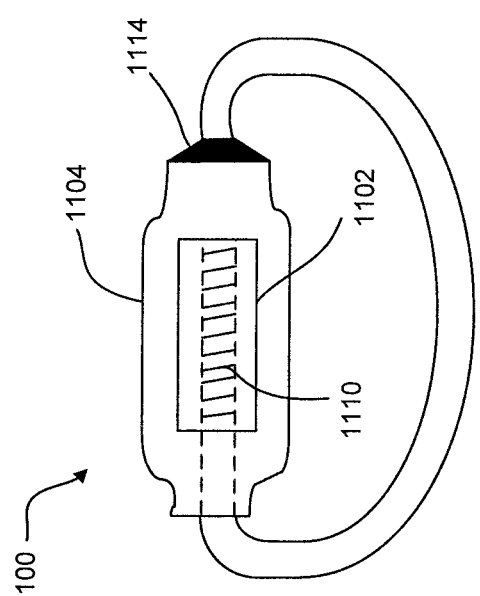

FIGS. 12A and 12B partially illustrate the annuloplasty ring 100 shown in FIG. 11A in a retracted position (FIG. 12A) and in an expanded position (FIG. 12B) according to certain embodiments. In FIG. 12A, the rotation of the magnet 1102 (e.g., clockwise) pulls the lead screw 1110 and/or threaded wire 1112 further into the magnet 1102 and the magnet housing 1104. In FIG. 12B, the rotation of the magnet 1102 (e.g., counter-clockwise) pushes the lead screw 1110 and/or threaded wire 1112 further out of the magnet 1102 and the magnet housing 1104. In one embodiment, a portion of the lead screw 1110 and/or the threads in the wire 1112 may extend beyond the magnet housing 1104 when the annuloplasty ring 100 is in the extended position. In another embodiment, the lead screw 1110 and/or the threads in the wire 1112 remain within the magnet housing 1104 in both the extended and retracted positions. Moving the lead screw 1110 and or the threaded portion of the threads in the wire 1112 into and out of the magnet 1110 allows improved control for symmetrically adjusting the annuloplasty ring 100 in the AP direction, as discussed above in relation to FIG. 7.

Figure 13A:
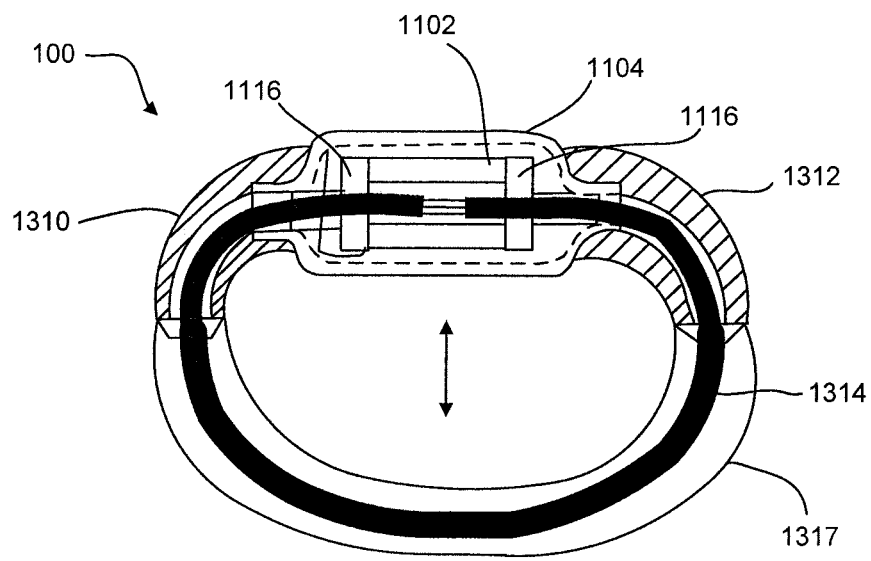
FIGS. 13A, 13B, and 13C are schematic diagrams of an adjustable annuloplasty ring according to another embodiment.
Figure 13B:
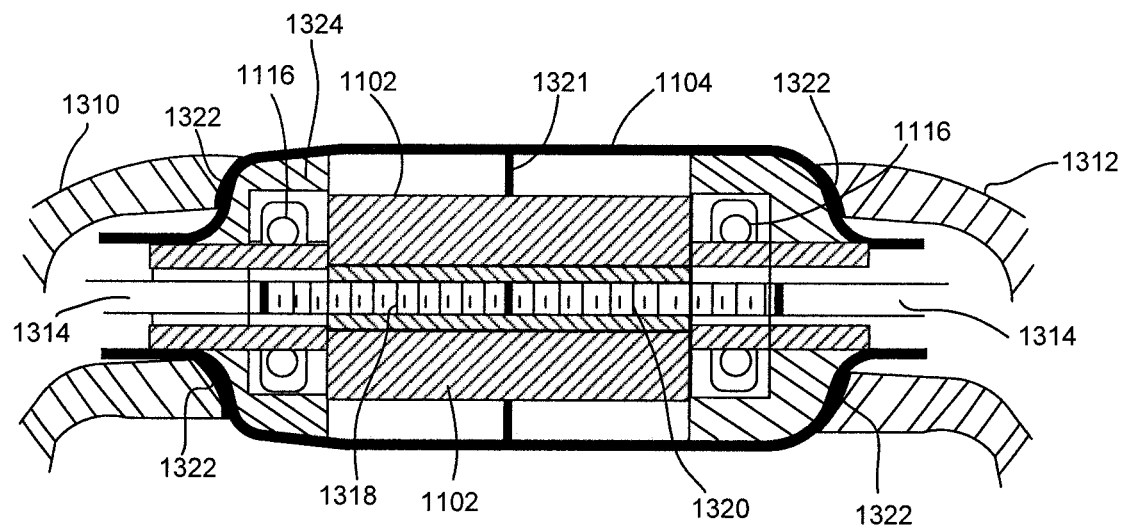
Figure 13C:
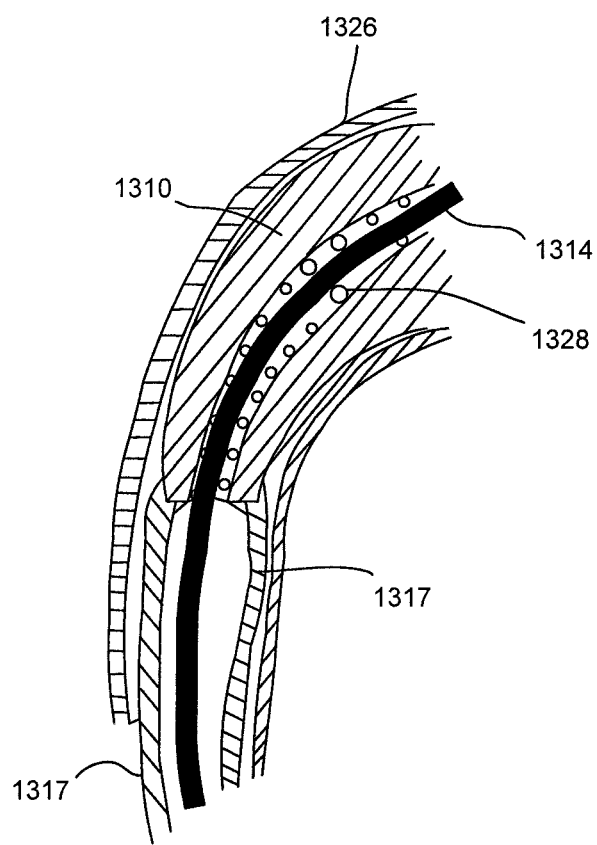

FIGS. 13A, 13B, and 13C are schematic diagrams of an adjustable annuloplasty ring 100 according to another embodiment. In this embodiment, the annuloplasty ring 100 includes arm extensions or "horns" 1310, 1312 attached to each end of the magnet housing 1104. The horns 1310, 1312 may include a suitable rigid or semi-rigid material such as metal or plastic. The horns 1310, 1312 redirect or angle a wire 1314 forming the loop of the annuloplasty ring 100. For example, the horns 1310, 1312 may redirect the wire 1314 approximately 90° from the cylindrical axis of the magnet 1102 within the housing 1104. Thus, the horns 1310, 1312 further maintain the "D" shape of the annuloplasty ring 100 such that it is substantially only adjusted in the AP direction (e.g., expansion/contraction of the loop is perpendicular to the rotation of the magnet 1102). In one embodiment, the annuloplasty ring 100 includes silicone tubing 1317 sealed to each horn 1310, 1312. The wire 1314 extends through the silicone tubing 1317. The silicone tubing 1317 stretches and contracts to accommodate circumferential changes to the loop in the annuloplasty ring 100.

FIG. 13B is a cross-sectional view of the housing 1104 shown in FIG. 13A according to one embodiment. In this embodiment, the magnet 1102 includes a first threaded insert 1318 and a second threaded insert 1320. The two inserts 1318, 1320 have opposite threaded orientations. For example, the first threaded insert 1318 may have a right-hand thread orientation and the second threaded insert 1320 may have a left-hand thread orientation. Both ends of the magnet 1102 may be coupled to bearings 1116 to support the spinning magnet 1102. Each end of the wire 1314 is threaded to interface with its respective threaded insert 1318, 1320 such that rotating the magnet 1102 in one direction pulls the ends of the wire 1314 toward each other and the center of the magnet, and rotating the magnet in the opposite direction pushes the ends of the wire 1314 away from each other and the center of the magnet 1102.

As also shown in FIG. 13B, the housing 1104 and horns 1310, 1312 are sealed from the outside environment. The housing 1104 may include two portions that are welded together along a weld line 1321. Further, the horns 1310, 1312 are bonded to the housing 1104 to create a hermetic seal 1322. Lubricant 1324 may also be sealed within portions of the housing 1104 to provide for proper operation of the bearings 1116.

FIG. 13C is a cross-sectional view of the interface between the horn 1310 and the silicone tubing 1317 according to one embodiment. As shown, in certain embodiments, the annuloplasty ring 100 may include a Dacron® covering 1326 (or other polyester covering) or a covering of other suitable material. The inner pathway of the horn 1310 may include a lubricant such as polytetrafluoroethylene (as known as PTFE Teflon®), silicone oil, grease, etc. to reduce friction between the wire 1314 and the horn 1310 during adjustment of the annuloplasty ring 100. The silicone tubing 1317 attaches to the horn 1310 and may provide an area into which sutures may be placed to secure the annuloplasty ring 100 to heart tissue. As discussed above, the silicone tubing 1317 also provides elasticity to accommodate expansion and contraction of the annuloplasty ring 100.

Figure 14A:
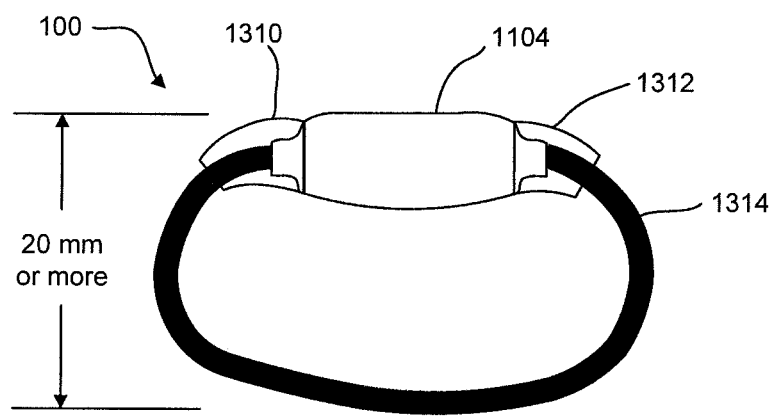
FIGS. 14A and 14B schematically illustrate one embodiment in which the superelasticity of a wire may be compressed so as to allow an annuloplasty ring to be inserted through a trocar.
Figure 14B:
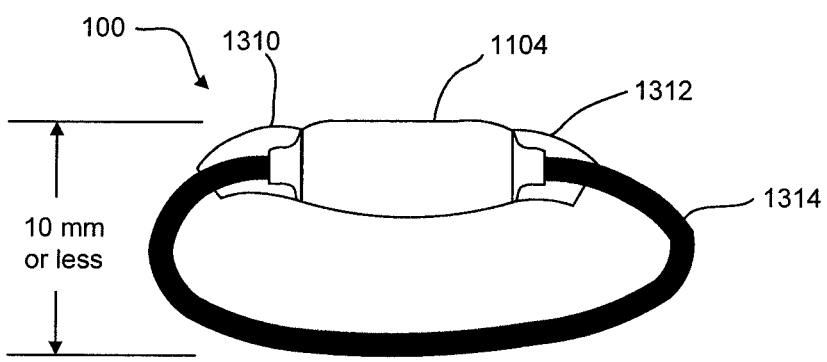

In certain embodiments, the annuloplasty ring 100 is configured for implantation into a heart through a narrow trocar or similar device. For example, FIGS. 14A and 14B schematically illustrate one embodiment in which the superelasticity of the wire 1314 (e.g., including a material such as nitinol), may be compressed so as to allow the annuloplasty ring 100 to be inserted through a trocar. In FIG. 14A, the size of the annuloplasty ring 100 in the AP dimension is approximately 20 mm or more according to some embodiments. This size may correspond to the dimensions of the annuloplasty ring 100 both before and after being inserted through the trocar. In FIG. 14B, the annuloplasty ring 100 is compressed so as to pass through the trocar. In this configuration, the size of the annuloplasty ring 100 in the AP dimension is approximately 10 mm or less according to some embodiments. The superelasticity of the wire 1314 allows for extreme flexibility, yet still provides the necessary strength after implantation for annuloplasty.

Figure 15A:
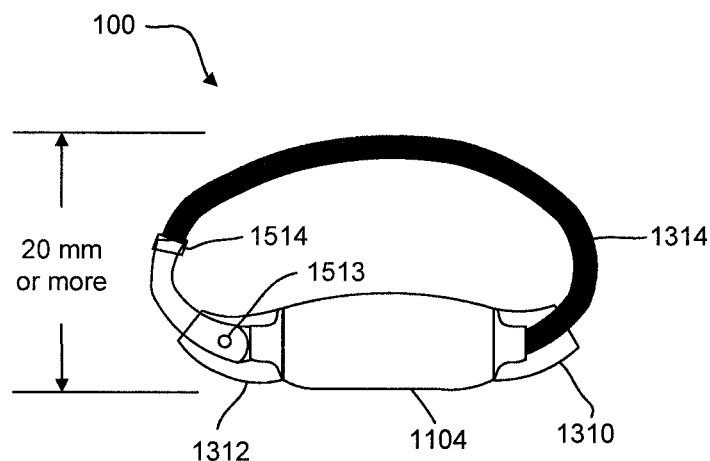
FIGS. 15A and 15B schematically illustrate an annuloplasty ring having a hinged arm according to one embodiment.
Figure 15B:
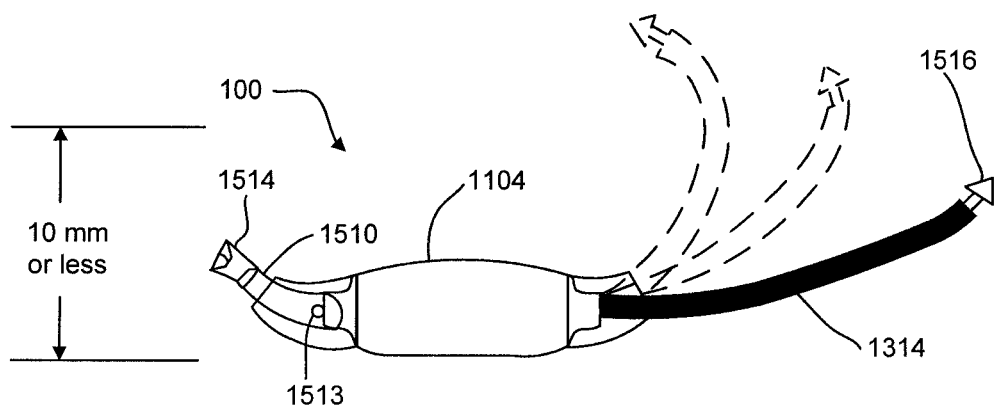

Other embodiments also allow for the annuloplasty ring 100 to be inserted through a trocar. For example, FIGS. 15A and 15B schematically illustrate an annuloplasty ring 100 having a hinged arm 1510 according to one embodiment. The hinged arm 1510 is connected to the housing 1104 through a pin joint 1513. The other end of the hinged arm 1510 includes a latch 1514 for engaging the superelastic wire 1314 after implantation through the trocar. For example, the latch 1514 may include a socket configured to receive a "snap-in" lock pin 1516 attached to the free end of the wire 314 curing implantation. Thus, the annuloplasty ring 100 may be inserted into a very small orifice without worry of damaging the wire 1314.

Figure 16A:
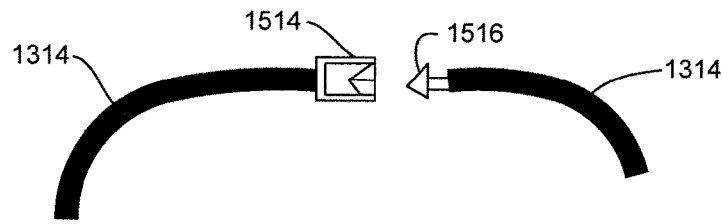
FIGS. 16A, 16B, 16C, 16D, and 16E schematically illustrate alternative latch embodiments that may be used with the annuloplasty ring shown in FIGS. 15A and 15B according to certain embodiments.
Figure 16B:
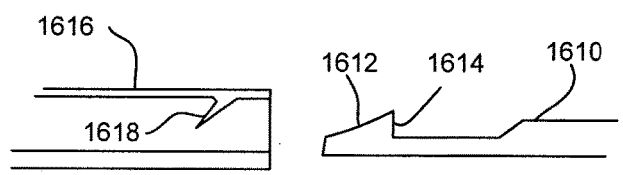
Figure 16C:
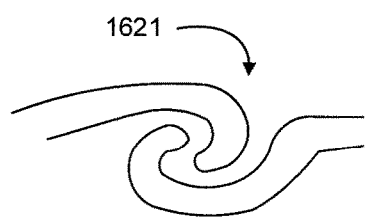
Figure 16D:
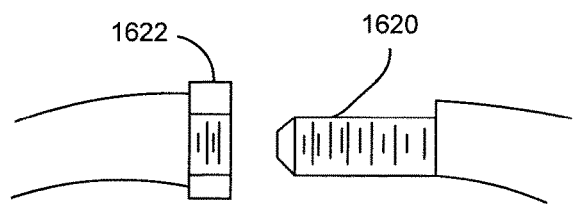
Figure 16E:
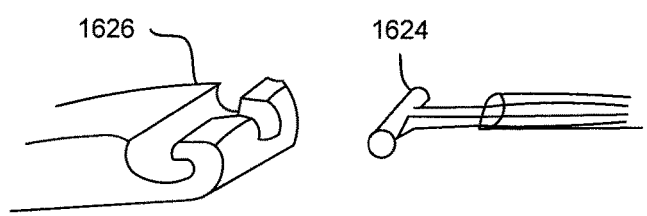

Alternative latch embodiments that may be used with the annuloplasty ring 100 shown in FIGS. 15A and 15B are schematically illustrated in FIGS. 16A, 16B, 16C, 16D, and 16E. FIG. 16A, for example, illustrates an embodiment wherein the socket latch 1514 and the lock pin 1516 are located anywhere along the wire 1314. In other words, the socket latch 1514 is not directly connected to the hinged arm 1510, as shown in FIGS. 15A and 15B. In FIG. 16B, the latching mechanism includes a "ramp and pawl" device in which a pin 1610 having a ramped surface 1612 and a vertical surface 1614 is inserted into a receptacle 1616 having a slanting protrusion 1618. The slanting protrusion 1618 is angled and sufficiently flexible so as to allow the slanted surface 1612 to proceed into the receptacle 1616. However, once inserted, the slanting protrusion 1618 interfaces with the vertical surface 1614 of the pin 1610 so as to prevent the pin 1610 from exiting the receptacle 1616, at least under normal operating conditions. In FIG. 16C, a "knuckle" style latch 1621 provides coupling simile to that used in trains. In FIG. 16D, the latch includes a threaded end 1620 configured to be screwed into a threaded nut 1622. In FIG. 16E, the latch includes a "T-bar" 1624 configured to be received by an appropriately shaped receptacle 1626. An artisan will recognize, of course, that the embodiments shown in FIGS. 16A, 16B, 16C, 16D, and 16E are provided by way of example only, and that many other different types of latches may also be used.

FIGS. 17A, 17B, 17C, 17D, 17E, and 17F are schematic diagrams of adjustable annuloplasty ring 100 according to another embodiment. In this embodiment, the annuloplasty ring 100 includes a first arm 1710 attached to the housing 1104, a second arm 1712 attached to the housing 1104, and a third arm 1714 extending between the first arm 1710 and the second arm 1712. As shown by the curved arrows in FIG. 17A, at least one of the first arm 1710 and the second arm 1712 may be pushed into or out of the housing 1104 in response to the rotation of the internal magnet 108 discussed above. The third arm 1714 is connected to at least one of the first arm 1710 and the second arm 1712 with a folding hinge 1716 that allows the loop portion of the annuloplasty ring 100 to be folded for insertion through a trocar. FIG. 17A illustrates a front view of the "open" or unfolded annuloplasty ring 100. FIG. 17B illustrates a front view of the "folded" annuloplasty ring 100 for insertion through the trocar. FIGS. 17C and 17D provide respective close-up views of the hinge 1716. After inserting the annuloplasty ring 100 through the trocar, the hinges are opened and may be locked in the open position for implantation around a heart valve (e.g., the mitral valve). For example, FIGS. 17E and 17F illustrate a locking mechanism that includes a locking sleeve 1720, a bias element 1722 (e.g., spring), and a mechanical stop 1724. In FIG. 17E, the locking sleeve 1720 is located above the hinge 1716. As the hinge 1716 is opened, the bias element 1722 pushes the locking sleeve 1720 over the hinge 1716 until it makes contact with the stop 1724, as shown in FIG. 17F. Thus, once the hinge 1716 is open, the bias element 1722 and the stop 1724 hold the locking sleeve 1720 in place such that the hinge 1716 cannot be opened, at least not without user intervention.

Figure 18:
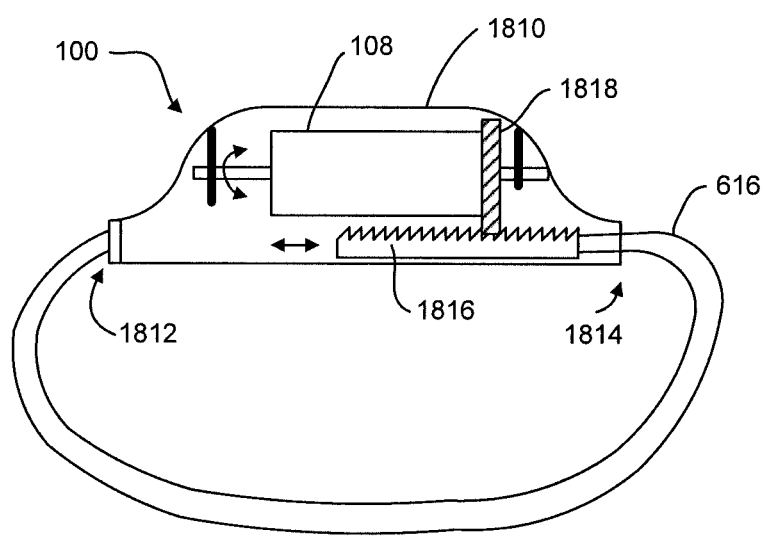
FIG. 18 is a schematic diagram of an adjustable annuloplasty ring according to another embodiment.
Figure 19:
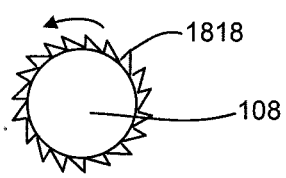
FIG. 19 is a simplified schematic illustrating an end view of a gear attached to a magnetic motor shown in FIG. 18 according to one embodiment.

FIG. 18 is a schematic diagram of an adjustable annuloplasty ring 100 according to another embodiment. In this embodiment, the annuloplasty ring 100 includes a housing 1810, a magnetic motor 108, and a wire 616, such as the magnetic motor 108 and wire 616 discussed above in relation to FIGS. 1B, 2A, 2B, 3, 4, and 6. The wire 616 includes a fixed end 1812 attached to the housing 1810 and a moving end 1814 attached to a rack 1816 located within the housing 1810. In one embodiment, the rack 1816 is cut or formed within the wire 616 itself. The magnetic motor 108 rotates in the presence of a rotating magnetic field so as to turn a gear 1818. The gear 1818 is in mechanical communication with the rack 1816 such that turning the gear 1818 slides the rack 1816 back and forth to change the size of the loop of the annuloplasty ring 100. For illustrative purposes, FIG. 19 is a simplified schematic illustrating an end view of the gear 1818 attached to the magnetic motor 108 according to one embodiment.

Figure 20A:
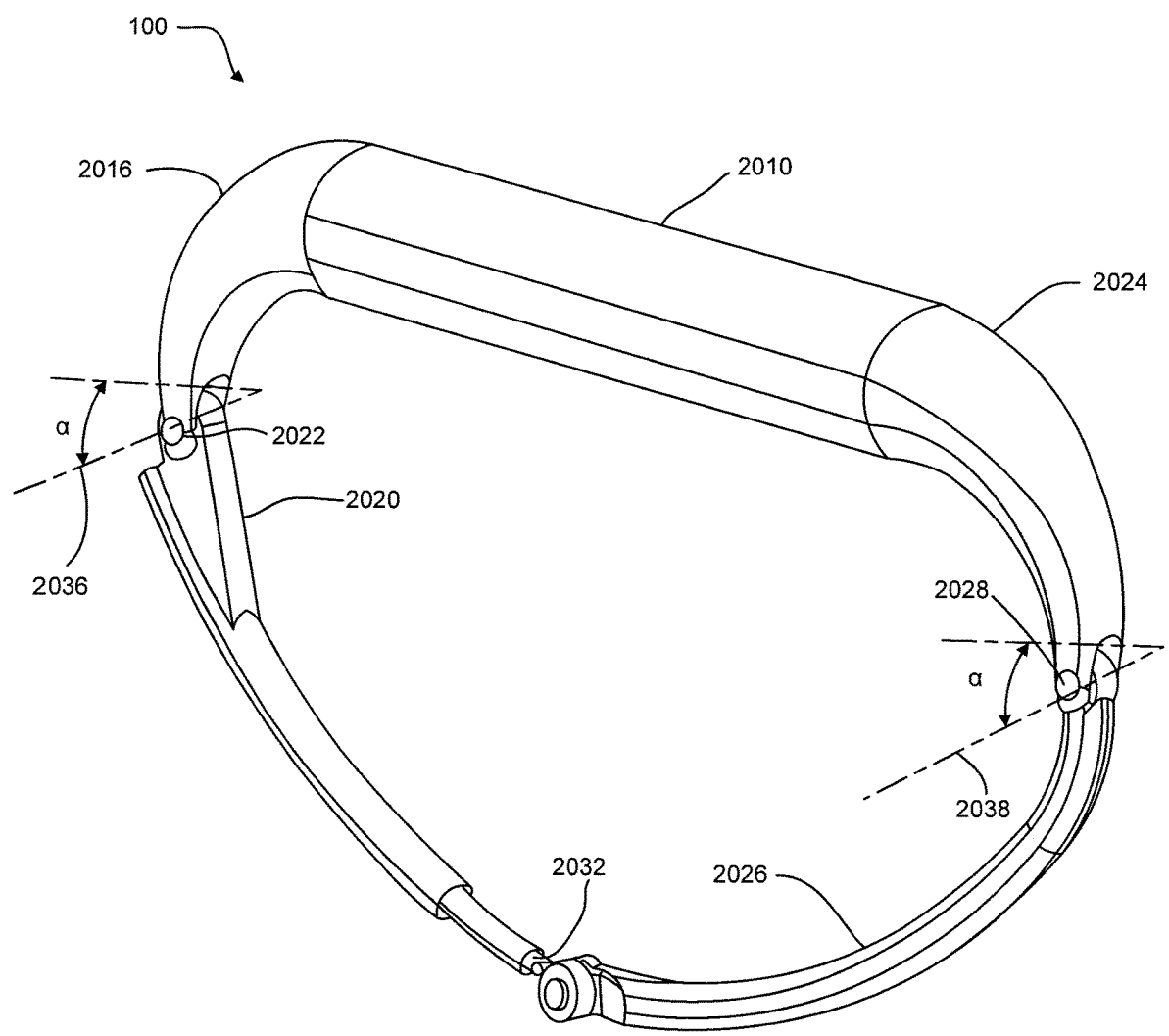
FIGS. 20A and 20B schematically illustrate an annuloplasty ring according to another embodiment.
Figure 20B:
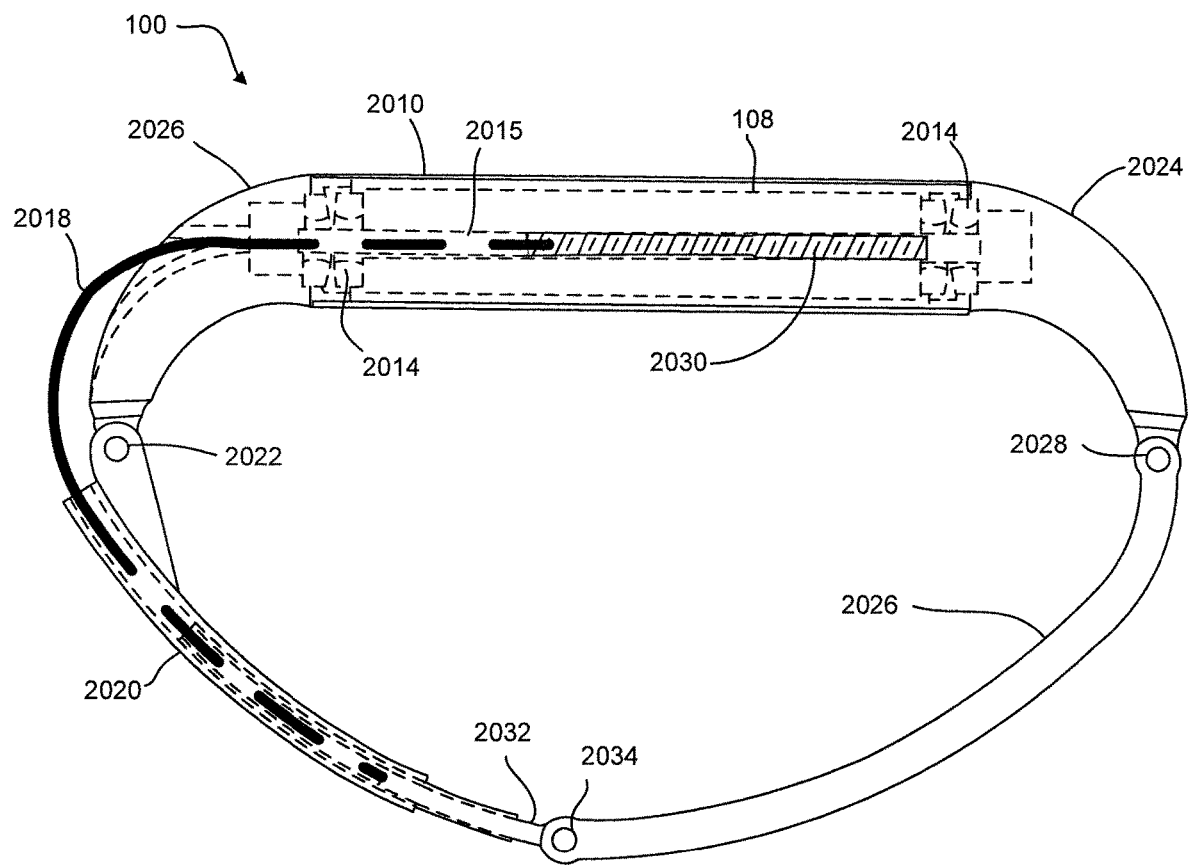

FIGS. 20A and 20B schematically illustrate an annuloplasty ring 100 according to another embodiment. FIG. 20A is a perspective view of the annuloplasty ring 100. FIG. 20B is a partially transparent top view of the annuloplasty ring 100. The annuloplasty ring 100 includes a body tube 2010 for enclosing a magnet 108. The magnet 108 is cylindrical and both ends thereof are coupled to bearings 2014 to allow the magnet 108 to rotate when exposed to a rotating magnetic field. The magnet 108 has magnetic poles divided along a plane that runs along the length of the cylinder. The magnet 108 includes a hollow region 2015 running along the length of the cylinder between the magnetic poles. The hollow region 2015 may be threaded or may include a threaded insert through which a lead screw 2030 is pulled (e.g., right and left as shown in FIG. 20B) through the magnet 108.

A first end of the body tube 2010 is connected to a first fixed arm 2016 and a first end of the lead screw 2030 crimps or otherwise attaches to a first end of a drive cable 2018. The first fixed arm 2016 is connected to a first swivel arm 2020 at a first pin joint 2022. A second end of the body tube 2010 is connected to a second fixed arm 2024 that is connected to a second swivel arm 2026 at a second pin joint 2028. A second end of the drive cable 2018 crimps or otherwise attaches to a push rod 2032. A second end of the push rod 2032 is connected to the second swivel arm 2026 at a third pin joint 2034.

When the magnet 108 is exposed to a rotating magnetic field (e.g., using the external magnetic adjustment device 102), the magnet 108 rotates. The connection of the drive cable 2018 between the lead screw 2030 and the push rod 2032 prevents the lead screw 2030 from rotating along with the magnet 108. Rather, the rotating magnet causes the lead screw 2030 to push and pull the drive cable 2018 into and out of the magnet 108, which causes the swivel arms 2020, 2026 to pivot at their respective pin joints 2022, 2028, 2034 to reduce or enlarge the size of the ring opening in the AP dimension. For example, the first pin joint 2022 may rotate around a first axis 2036 and the second pin joint 2028 may rotate around a second axis 2038 (which is parallel to the first axis 2036) such that the swivel arms 2020, 2026 move in a first plane.

In addition, or in other embodiments, the annuloplasty ring 100 is configured to change shape in a second plane. For example, one or more of the pin joints 2022, 2028, 2034 shown in FIG. 20B may be replaced by ball joints (or pin joints that rotate in a diff rent direction). In such an embodiment, the ball joints may be configured to rotate out of the first plane when the rotating magnet 108 pushes or pulls the drive cable 2018. For example, first joint 2022 and/or the second joint 2028 may rotate at an angle α with respect to the second axis 2038. In one such embodiment, the annuloplasty ring 100 is configured to form a saddle shape when the rotating magnet 108 pushes or pulls the drive cable 2018.

Figure 21:
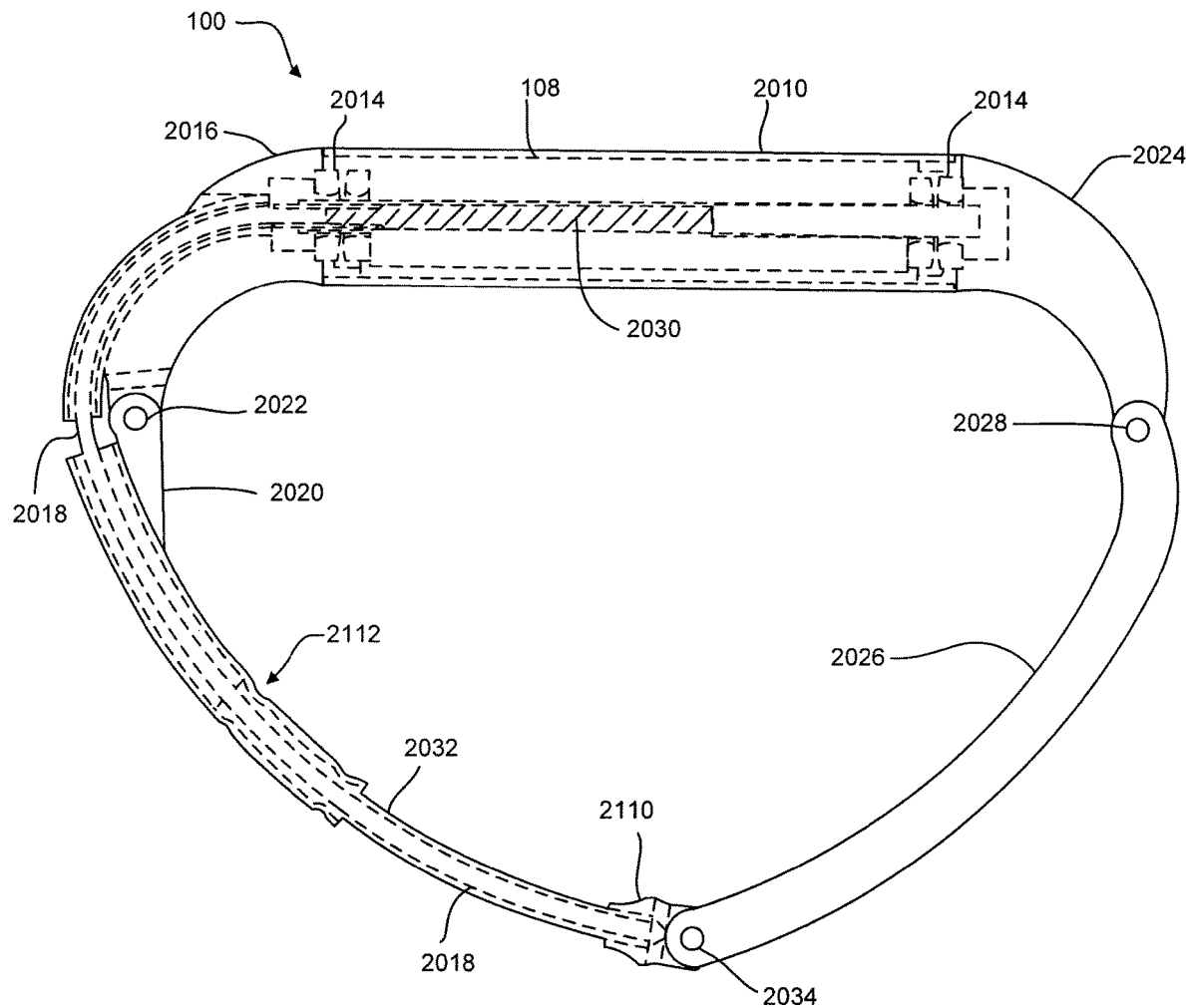
FIG. 21 schematically illustrates an annuloplasty ring according to another embodiment.

FIG. 21 schematically illustrates an annuloplasty ring 100 according to another embodiment. The embodiment illustrated in FIG. 21 is similar to the embodiment shown in FIGS. 20A and 20B, except that the push rod 2032 is hollow to allow the drive cable 2018 to be inserted and secured therein. The annuloplasty ring 100 in FIG. 21 also includes a coupler 2110 to attach the push rod 2032 and/or the drive cable 2018 to the second swivel arm 2026 at the third pin joint 2034. As the rotating magnet 108 pushes and pulls the drive cable 2018, the drive cable 2018 pushes and pulls the push rod 2032 through the first swivel arm 2020, which causes the swivel arms 2020, 2026 to pivot at their respective pin joints 2022, 2028, 2034 to reduce or enlarge the size of the ring opening in the AP dimension. As a safety feature, the first swivel arm 2020 includes one or more divots or crimps 2112 configured to engage the sliding end of the push rod 2032 to prevent it from exiting the second swivel arm 2020.

Figure 22:
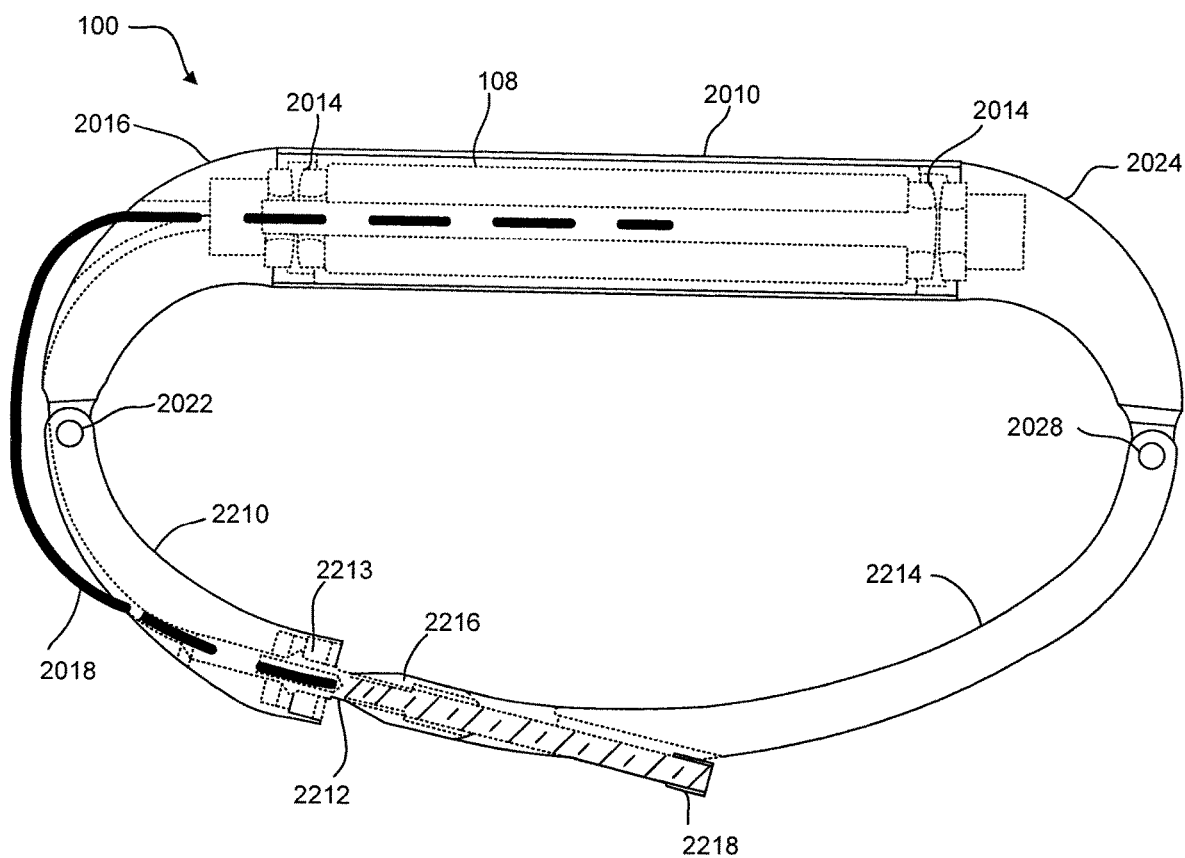
FIG. 22 schematically illustrates an annuloplasty ring according to another embodiment.

FIG. 22 schematically illustrates an annuloplasty ring 100 according to another embodiment. The annuloplasty ring 100 includes the body tube 2010, magnet 108, bearings 2014, first fixed arm 2016, second fixed arm 2024, drive cable 2018, first pin joint 2022, and second pin joint 2028 discussed above in relation to FIGS. 20A and 20B. In this embodiment, however, the magnet 108 need not be threaded, though it may or may not be hollow to facilitate attachment of the drive cable 2018. A first end of the drive cable 2018 is attached to either the magnet 108 such that rotating the magnet 108 causes the drive cable 2018 to rotate.

The annuloplasty ring 100 shown in FIG. 22 includes a first swivel arm 2210 attached to the first fixed arm 2016 at the first pin joint 2022. The first swivel arm 2210 is coupled to a lead screw 2212 using a bearing 2213. A second end of the drive cable 2018 is attached to a first end of the lead screw 2213 such that rotating the drive cable 2018 causes the lead screw 2212 to rotate about the bearing 2213. The bearing 2213 allows the lead screw to rotate freely without detaching from the first swivel arm 2210. A second swivel arm 2214 is attached to the second fixed arm 2024 at the second pin joint 2028. The second swivel arm 2214 includes a threaded drive nut 2216 that engages the threads of the threads of the lead screw 2212. As the lead screw 2212 screws into or out of the drive nut 2216, the swivel arms 2210, 2214 pivot at their respective pin joints 2022, 2028 to reduce or enlarge the size of the ring opening in AP dimension. The lead screw 2212 may include an end stop 2218 to prevent the lead screw 2212 from being removed (e.g., unscrewed) from the drive nut 2216.

Figure 23A:
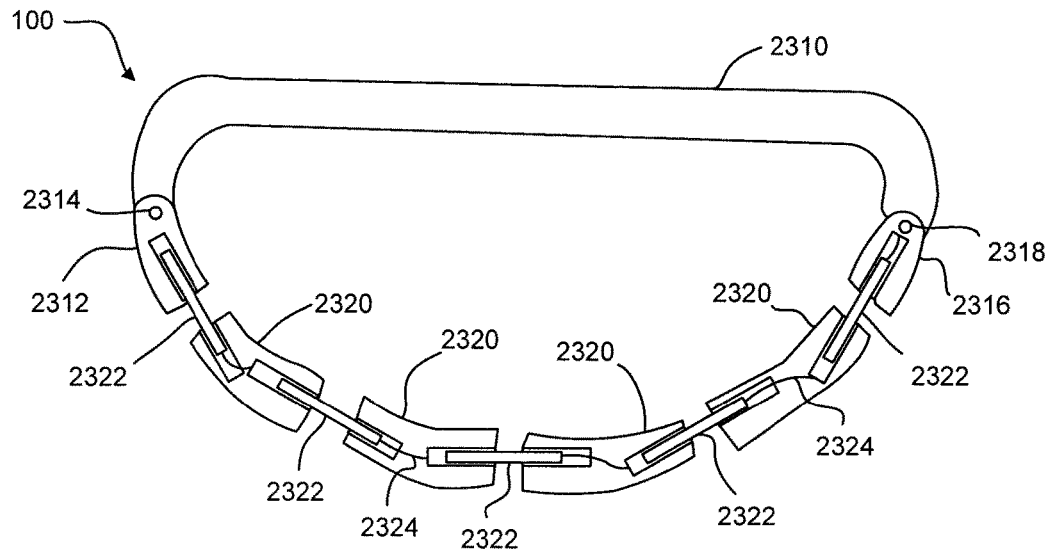
FIGS. 23A, 23B, and 23C schematically illustrate a multi-segment annuloplasty ring according to one embodiment.
Figure 23B:
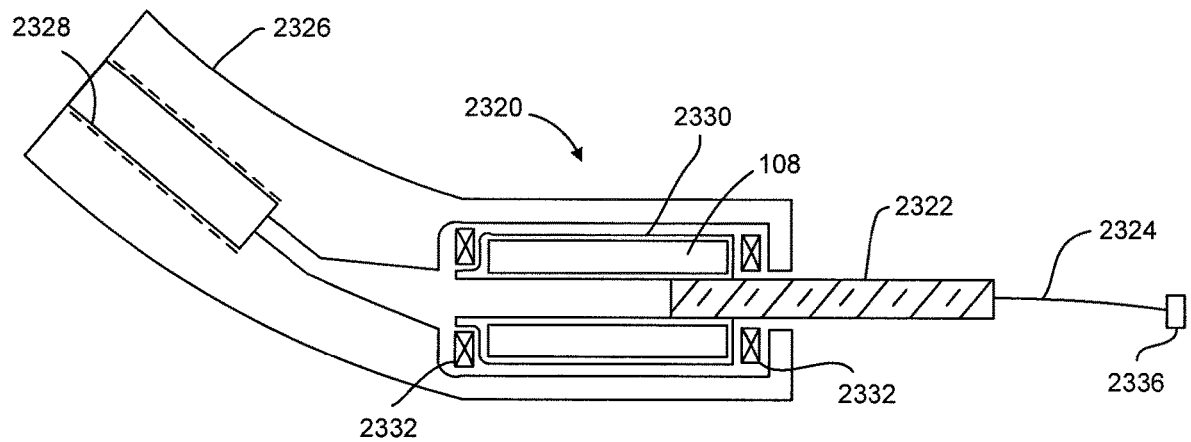
Figure 23C:
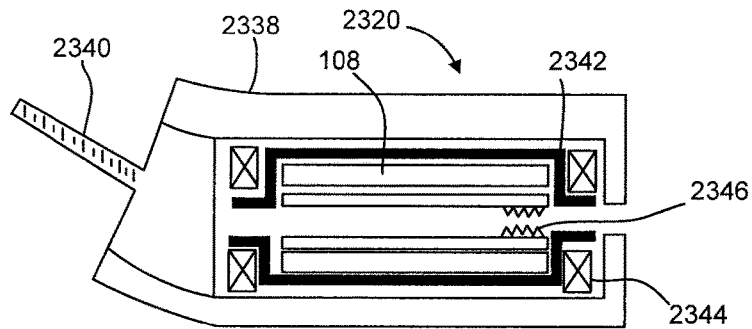

An artisan will recognize that many changes may be made to the annuloplasty ring embodiments disclosed herein. For example, FIGS. 23A, 23B, and 23C illustrate a multi-segment annuloplasty ring 100 according to one embodiment. The annuloplasty ring 100 includes a body tube 2310 attached to a first magnetic drive segment 2312 at a first pin joint 2314 and a second magnetic drive segment 2316 at a second pin joint 2318. The annuloplasty ring 100 may include one or more additional magnetic drive segments 2320 (four shown in the example of FIG. 23A) coupled between the first magnetic drive segment 2312 and the second magnetic drive segment 2316. The magnetic drive segments 2312, 2316, 2320 are coupled to one another with respective lead screws 2322 (five shown in the example of FIG. 23A). Safety wires 2324 (five shown in the example of FIG. 23A) are attached between each lead screw 2322 and a respective magnetic drive segment 2318, 2320. Each magnetic drive segment 2312, 316, 2320 includes a magnet 108 (FIGS. 23B and 23C) that may be rotated using a changing magnetic field to drive the respective lead screws 2322. Thus, the distance between adjacent magnetic drive segments 2312, 2316, 2320 may be selectively adjusted. In one embodiment, the position of each magnetic drive segment 2312, 2316, 2320 may be individually adjusted.

FIG. 23B schematically illustrates an example magnetic drive segment 2320 according to one embodiment. The magnetic drive segment 2320 include a link housing 2326 having a first end with a threaded drive nut 2328 for receiving a first lead screw 2322 (not shown in FIG. 23B). A second end of the link housing 2326 includes a hollow magnet 108 within a magnet housing 2330. The magnet 108 and magnet housing 2332 are attached to bearings 2332 that allow them to rotate in the presence of a rotating magnetic field. A second lead screw 2322 is connected to and rotates with the magnet 108, and is attached to a first end of a safety wire 2324. A second end of the safety wire 2324 is attached to a safety stop 2336 configured to attach to one of the other magnetic drive segments 2312, 2316, 2320 shown in FIG. 23A.

FIG. 23C schematically illustrates an example magnetic drive segment 2320 according to another embodiment. The magnetic drive segment 2320 shown in FIG. 23C includes a link housing 2338 having a first end fixed to a threaded stud 2340. The threaded stud 2340 is configured to be received by one of the other magnetic drive segments 2312, 2316, 2320 shown in FIG. 23A. Thus, in this embodiment, some or all of the separate drive screws 2322 are not used. A second end of the link housing 2338 includes a hollow magnet 108 within a magnet housing 2342. The magnet 108 and magnet housing 2342 are attached to bearings 2344 that allow them to rotate in the presence of a rotating magnetic field. An inner magnet housing 2346 is threaded to receive a lead screw 2322 or a threaded stud fixed to one of the other magnetic drive segments 2312, 2316, 2320 shown in FIG. 23A.

Figure 24:
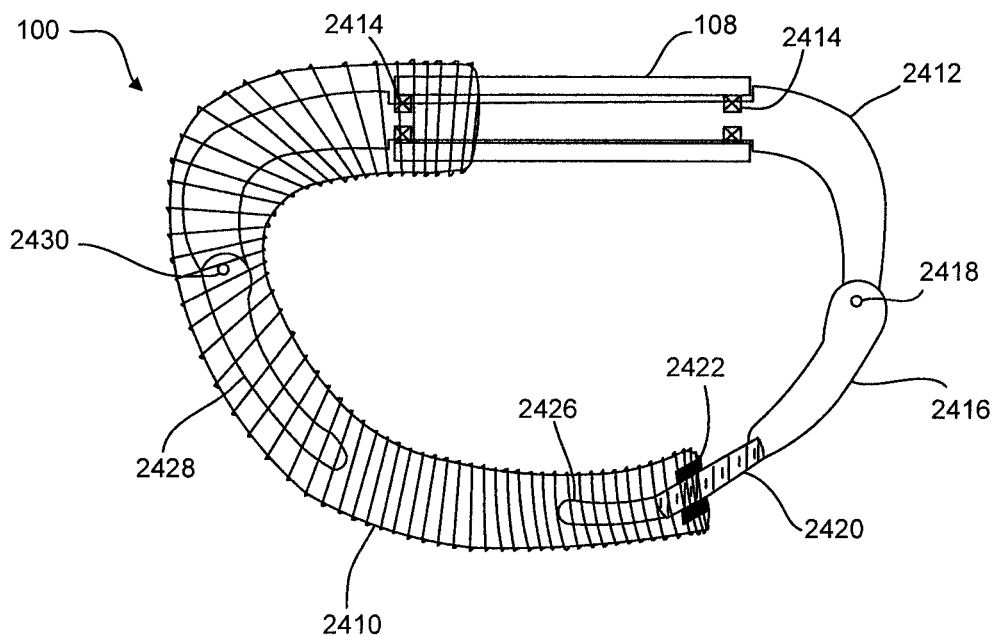
FIG. 24 is a schematic diagram of an annuloplasty ring that includes a bidirectional torsion drive cable according to one embodiment.
Figure 25:
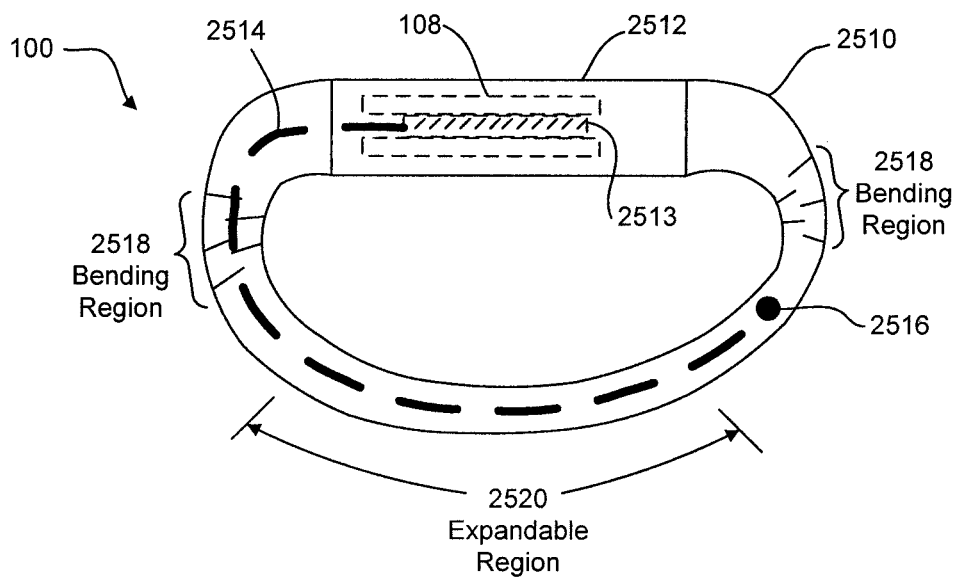
FIG. 25 is a schematic diagram of an annuloplasty ring that includes an elastic tube according to one embodiment.

FIG. 24 is a schematic diagram of an annuloplasty ring 100 that includes a bidirectional torsion drive cable 2410 according to one embodiment. The annuloplasty ring 100 includes a C-shaped base 2412 that passes through a hollow magnet 108. In the presence of a rotating magnetic field, the hollow magnet 108 rotates on bearings 2414 attached to the base 2412. A first end of the base 2412 is attached to a first swivel arm 2416 at a first pin joint 2418. The first swivel arm 2416 includes a threaded section 2420. A first end of the bidirectional torsion drive cable 2410 is attached to a first end of the magnet 108. A second end of the bidirectional torsion cable 2410 includes a drive nut 2422 that engages the threaded section 2420 of the first swivel arm 2416. In one embodiment, the first swivel arm 2416 includes a curved lead-in section 2426 to assist in controlling the shape of the bidirectional torsion drive cable 2410. In addition, or in other embodiments, the annuloplasty ring 100 may also include a second swivel arm 2428 connected to a second end of the base 2412 at a second pin joint 2430. The second swivel arm 2428 also assists in controlling the shape of the bidirectional torsion drive cable 2410. As the magnet 108 rotates, the drive nut 2422 draws the threaded section 2420 of the first swivel arm 2416 into and out of the bidirectional torsion drive cable 2410 to adjust the size of the annuloplasty ring 100. The bidirectional torsion drive cable 2410 may include, for example, a flexible shaft available from S.S. White Technologies, Inc., of Piscataway, N.J., FIG. 25 is a schematic diagram of an annuloplasty ring 100 that includes an elastic tube 2510 according to one embodiment. The elastic tube 2510 extends between the ends of a rigid base 2512 to form a D-shaped ring. A magnet 108 with internal threads (as discussed above) is configured to rotate within the base 2512 in the presence of a rotating magnetic field. A first end of a drive cable 2514 may be threaded so as to engage the internal threads of the magnet 108. In another embodiment, as shown in FIG. 25, the first end of the drive cable 2514 is attached to a threaded drive screw 2513 configured to engage the internal threads of the magnet 108. A second end of the drive cable 2514 is attached to an anchor point 2516 within the elastic tube 2510. As the magnet 108 rotates, the drive cable 2514 is drawn into and out of the magnet 108. The elastic tube 2510 includes bending regions 2518 and an expandable region 2520. The drive cable 2514 acts as a draw string to control the circumference of the expandable section 2520 of the elastic tube 2510. In one embodiment, the elastic tube 2510 comprises superelastic nitinol.

Figure 26:
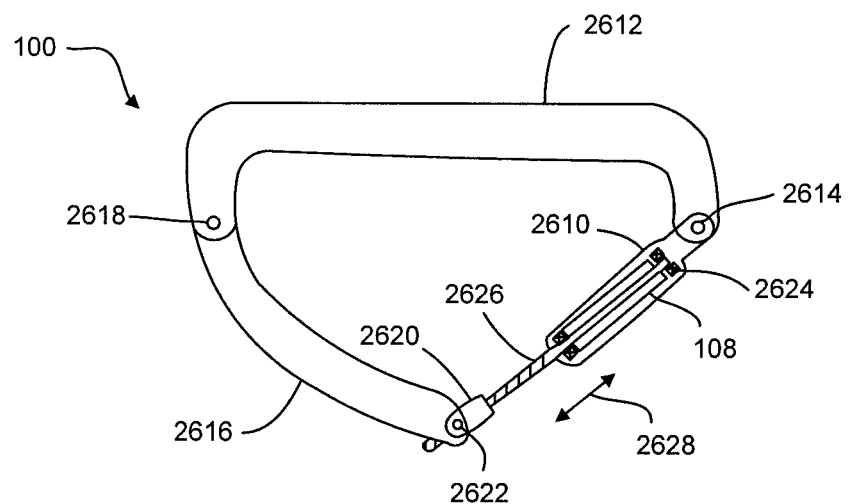
FIG. 26 is a schematic diagram of an annuloplasty ring that includes a rotatable magnet within a pivot arm according to one embodiment.

FIG. 26 is a schematic diagram of an annuloplasty ring 100 that includes a rotatable magnet 108 within a pivot arm 2610 according to one embodiment. The annuloplasty ring 100 includes a C-shaped base 2612 attached to a first end to the pivot arm 2610 at a first pin joint 2614. A second end of the base 2612 is attached to a first end of a second pivot arm 2616 at a second pin joint 2618. A second end of the second pivot arm 2616 is attached to a drive nut 2620 at a third pin joint 2622. As discussed above, the magnet 108 (or an attached magnet housing) may be coupled to bearings 2624 that allow the magnet 108 to rotate within the pivot arm 2610. The magnet 108 (or a magnet housing) is attached to a first end of a lead screw 2626. A second end of the lead screw 2626 interfaces with the drive nut 2620. Thus, as the magnet 108 rotates in the presence of a rotating magnetic field, the lead screw 2626 is drawn into and out of the drive nut 2020 in the direction of the illustrated arrow 2628 to adjust the size of the annuloplasty ring 100.

Figure 27:
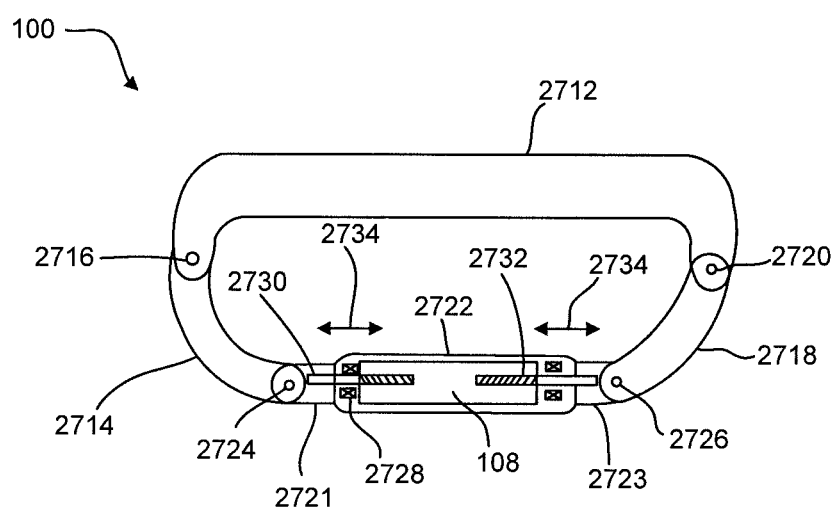
FIG. 27 is a schematic diagram of an annuloplasty ring according to another embodiment.

FIG. 27 is a schematic diagram of an annuloplasty ring 100 according to another embodiment. The annuloplasty ring 100 includes a C-shaped base 2712 having a first end attached to a first end of a first pivot arm 2714 at a first pin joint 2716. A second end of the base 2712 is attached to a first end of a second pivot arm 2718 at a second pin joint 2720. A second end of the first pivot arm 2714 is attached to a first coupler 2721 at a third pin joint 2724. A second end of the second pivot arm 2718 is attached to a second coupler 2723 at a fourth pin joint 2726. A magnet 108 is configured to rotate on bearings 2728 within a drive housing 2722. The first coupler 2721 is attached to a first lead screw 2730 and the second coupler 2723 is attached to a second lead screw 2732. Each lead screw 2730, 2732 is configured to interface with respective internal threads of the magnet 108. The first lead screw 2730 and the second lead screw 2732 are threaded in opposite directions. For example, the first lead screw 2730 may have left-hand threads and the second lead screw 2732 may have right-hand threads. Thus, as the magnet 108 rotates in the presence of a rotating magnetic field, both lead screws 2730, 2732 are either drawn into the magnet 108, or both lead screws 2730, 2732 are drawn out of the magnet 108 in the direction of the illustrated arrows 2734 to adjust the size of the annuloplasty ring 100.

Example External Magnetic Adjustment Device

Figure 28:
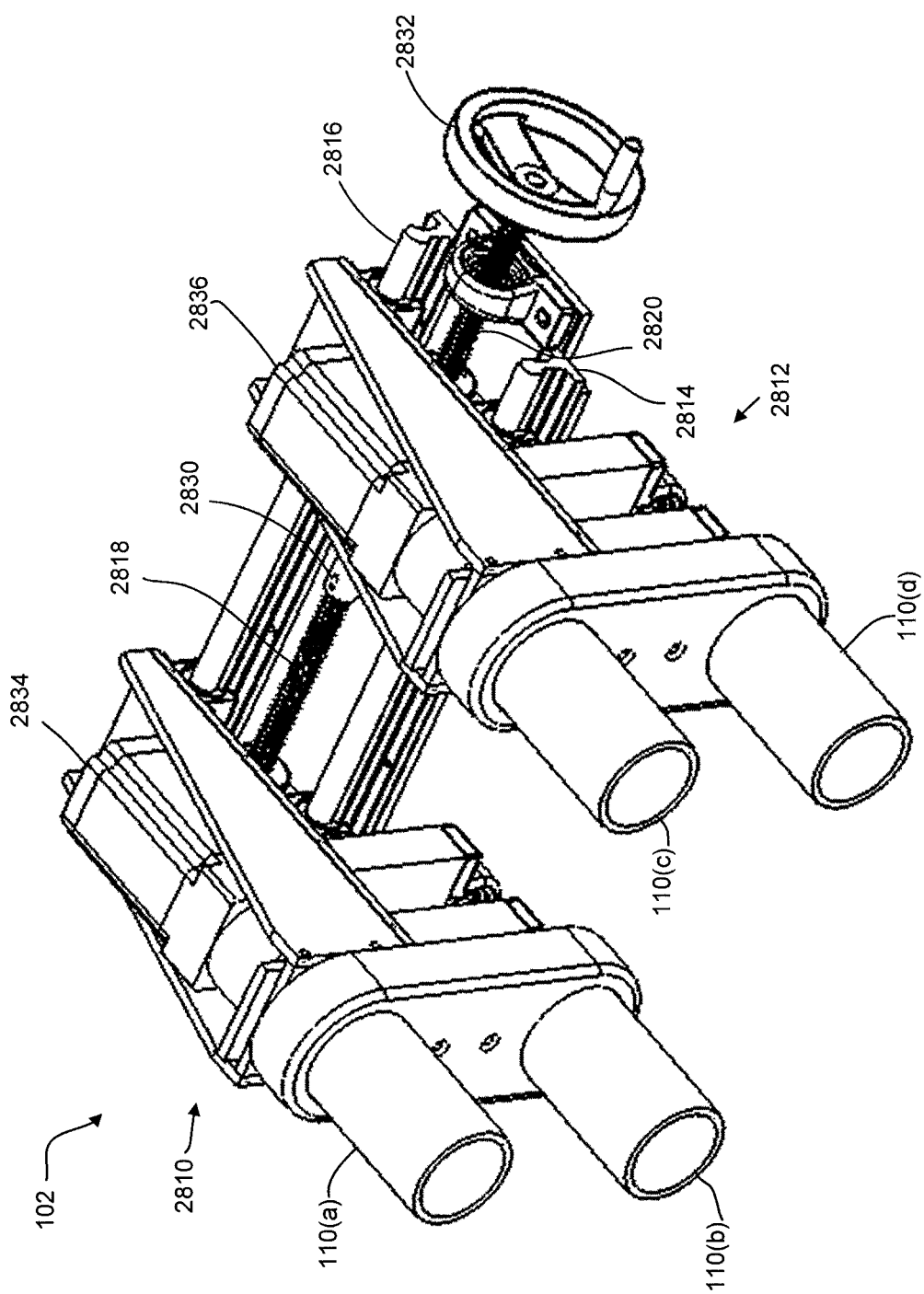
FIG. 28 is a perspective view of an external magnetic adjustment device according to one embodiment.

FIG. 28 is a perspective view of an external magnetic adjustment device 102 according to one embodiment. The external magnetic adjustment device 102 includes a first cylindrical magnet 110(a), a second cylindrical magnet 110(b), a third cylindrical magnet 110(c), and a fourth cylindrical magnet 110(d) (referred to collectively as magnets 110). In one embodiment, the magnets 110 are permanent magnets. In another embodiment, the magnets 110 are electromagnets configured in be selectively activated. The first magnet 110(a) and the second magnet 110(b) are attached to a first arm 2810. The third magnet 110(c) and the fourth magnet 110(d) are attached to a second arm. The first arm 2810 and the second arm 2812 are configured to slide relative to each other in opposite directions along a first rail 2814 and a second rail 2816. Thus, a patient's chest may be placed between the magnets 110 of the first arm 2810 and the second arm 2812 during adjustment of a magnetic annuloplasty ring (such as the annuloplasty rings 100 discussed above) implanted within the patient's heart, As shown in FIG. 28, the first arm 2810 may be connected to a first screw 2818 threaded in a first direction (e.g., right-hand threads) and the second arm 2812 may be connected to a second screw 2820 threaded in a second direction (e.g., left-hand threads). The first screw 2818 is connected to the second screw 2820 by a coupler 2830 such that both screws 2818, 2820 turn at the same time. A user may turn the screws 2818, 2820 using, for example, a hand crank 2832 to adjust the relative positions of the arms 2810, 2812. In another embodiment, a motor (not shown) under the control of a controller (such as the controller 624 shown in FIG. 6) may be used to turn the screws 2818, 2820.

The first arm 2810 includes a first stepper motor 2834 configured to rotate the first magnet 110(a) and the second magnet 110(b). For example, an axle (not shown) may be connected to the first magnet 110(a) and a coupling such as a drive chain (not shown may couple the first magnet 110(a) to the second magnet 110(b) such that the magnets 110(a), 110(b) rotate together in the same direction. Similarly, the second arm 2812 includes a second stepper motor 2834 configured to rotate the third magnet 110(c) and the fourth magnet 110(d). In other embodiments, additional stepper motors (not shown) may be used to independently rotate each magnet. In yet another embodiment ail of the magnets 110 are coupled to a single stepper motor (not shown). The stepper motors 2834, 2836 may be controlled by a host computer or controller (such as the controller 624 shown in FIG. 6) to coordinate the rotation of the magnets 110 at a desired frequency to generate a changing magnetic field suitable for adjusting the annuloplasty ring 100.

The strength of the magnetic field generated by the magnets 110 in the area between the first arm 2810 and the second arm 2812, and in surrounding areas, is based on the polar alignment (e.g., north and south poles) of each magnet 110. For example, FIGS. 29A, 29B, 29C, and 29D schematically illustrate end views of the magnets 110 of the external magnetic adjustment device 102 shown in FIG. 28 according to certain embodiments. In the illustrated examples, a first magnetic pole (e.g., north) is represented by a white semicircle and a second magnetic pole (e.g. south) is represented by a black semicircle. The illustrated examples also graphically illustrate the resulting magnetic field lines resulting from each polar alignment configuration.

Figure 29B:
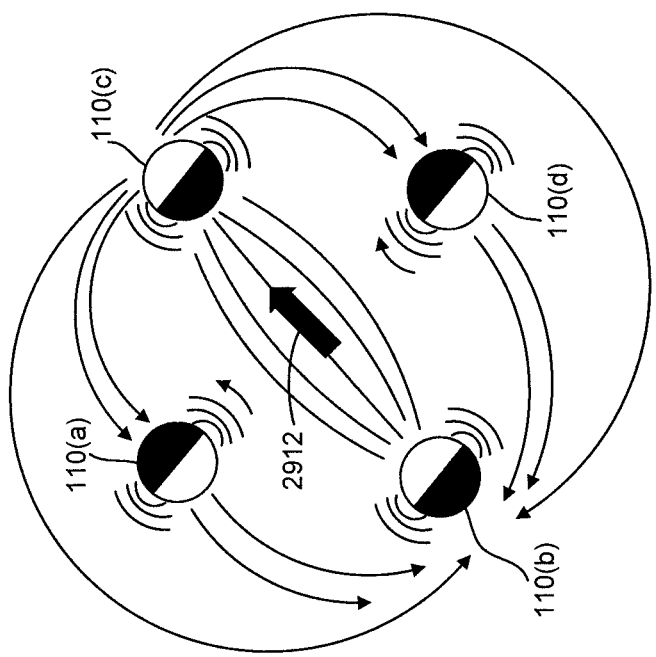
FIGS. 29A, 29B, 29C, and 29D schematically illustrate end views of the magnets of the external magnetic adjustment device shown in FIG. 28 according to certain embodiments.
Figure 29A:
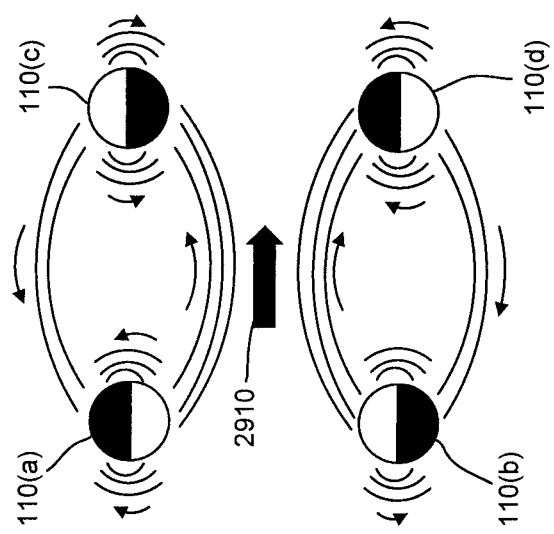

In FIG. 29A, the magnets 110 are in an anti-aligned (Halbach) arrangement with the line separating the magnetic poles in each magnet 110 set at a 0° offset from a horizontal direction. In this arrangement, the magnetic fields from each magnet 110 combine so as to augment the total magnetic field (as illustrated by the arrow 2910) in the central area of the magnet array, while reducing (or not augmenting) the magnetic field in areas outside of the magnet array. Thus, an annuloplasty ring located in the central area of the magnet array may be adjusted in a medical setting (e.g., hospital or physician's office) without the magnetic field altering nearby medical or non-medical devices. When the magnets 110 are rotated in unison, the magnetic field in the central area of the magnet array rotates in the opposite direction. For example, FIG. 29B illustrates the magnets 110 rotated 45° in a clockwise direction as compared to the arrangement of FIG. 29A. Accordingly, the total magnetic field in the central area of the magnet array (as illustrated by the arrow 2912) is also rotated 45°, but in the counterclockwise direction.

Figure 29D:
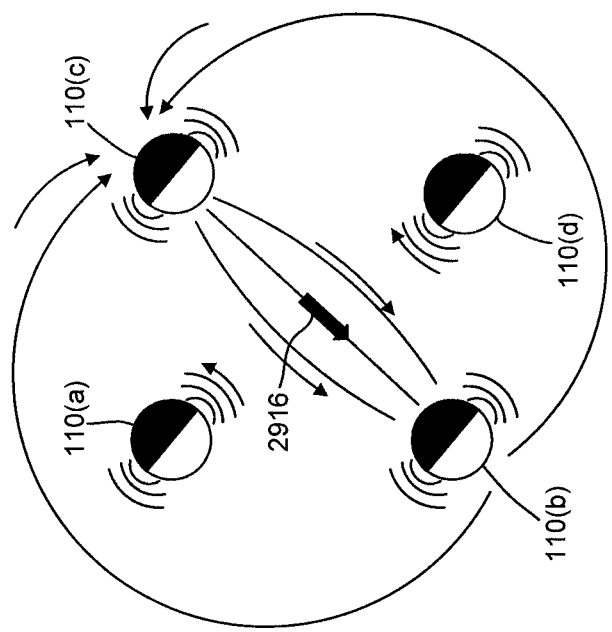
Figure 29C:
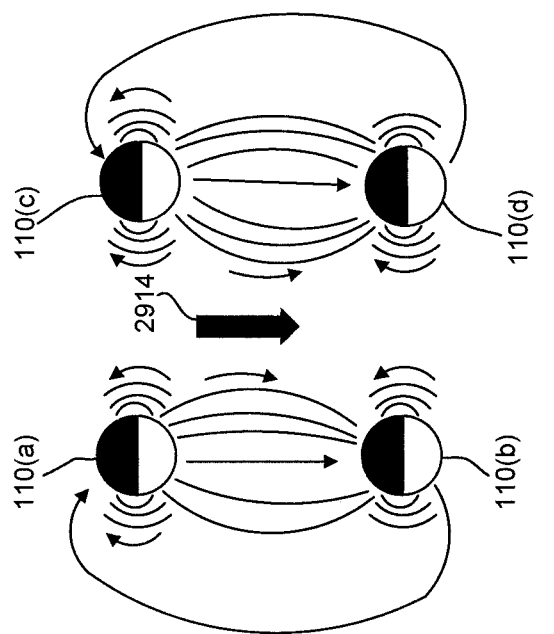

In FIG. 29C, the magnets 110 are in an aligned arrangement such that the magnetic poles are all facing the same direction. Further, the line separating the magnetic poles in each magnet 110 set at a 0° offset from a horizontal direction. In this arrangement, the magnetic fields from each magnet 110 also combine so as to augment the total magnetic field (as illustrated by the arrow 2914) in the central area of the magnet array. However, in some embodiments (see FIG. 30A), the total magnetic field generated in the central region by the aligned arrangement shown in FIG. 29C may not be as great as that of the Halbach arrangement shown in FIG. 29A. Further, the total magnetic field in central region of the magnet array may decrease as the magnets 110 are rotated. For example, FIG. 29D illustrates the magnets 110 rotated 45° in a clockwise direction as compared to the arrangement of FIG. 29C. Accordingly, the total magnetic field in the central area of the magnet array (as illustrated by the arrow 2916) is also rotated 45° in the clockwise direction. However, the magnitude of the total magnetic field in the central region of the magnet array is reduced due to counteracting magnetic fields generated by the first magnet 110(a) and the fourth magnet 110(d).

Figure 30A:
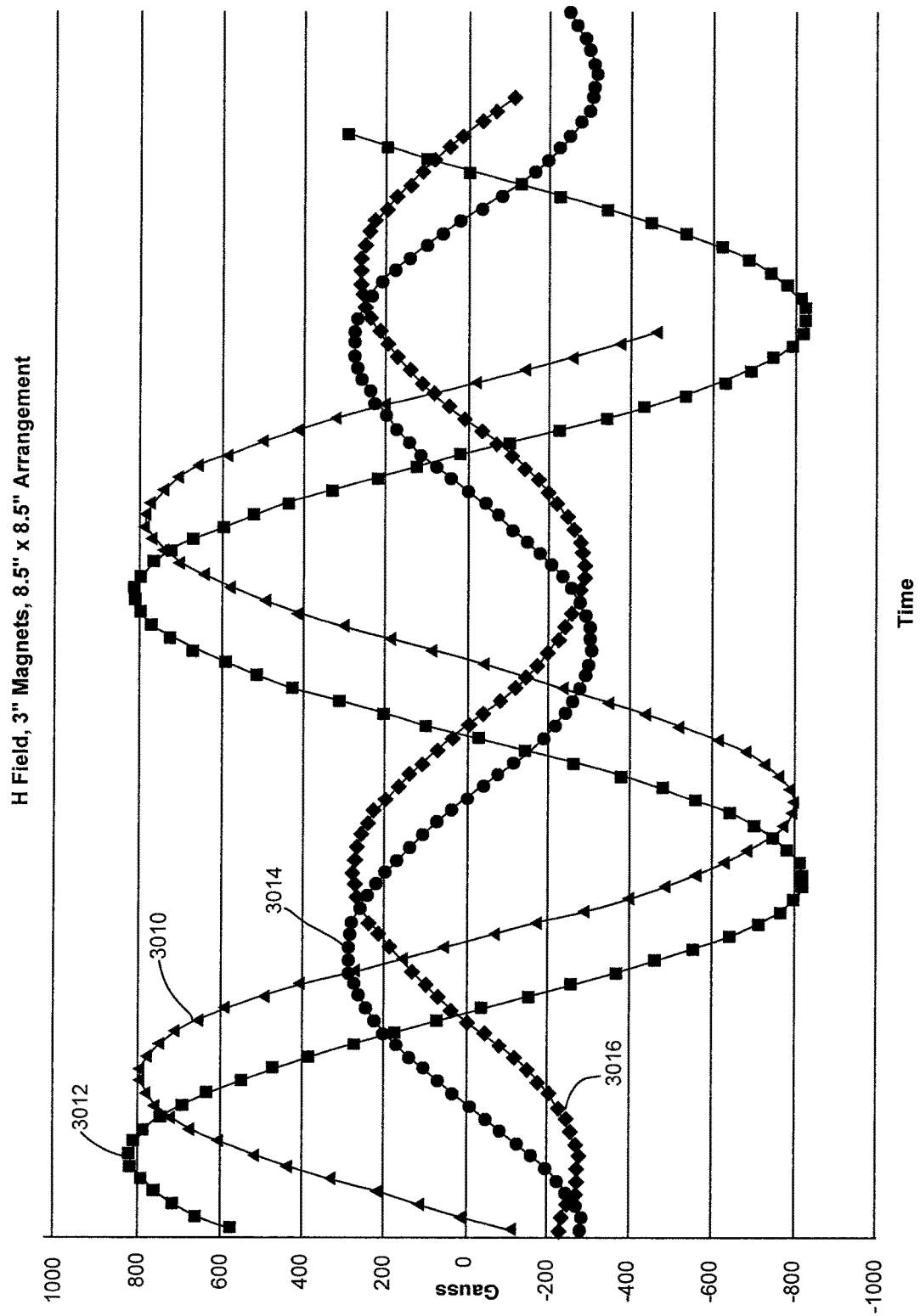
FIGS. 30A and 30B graphically represent example magnetic field measurements as the magnets of the external magnetic adjustment device are rotated according to certain embodiments.
Figure 30B:
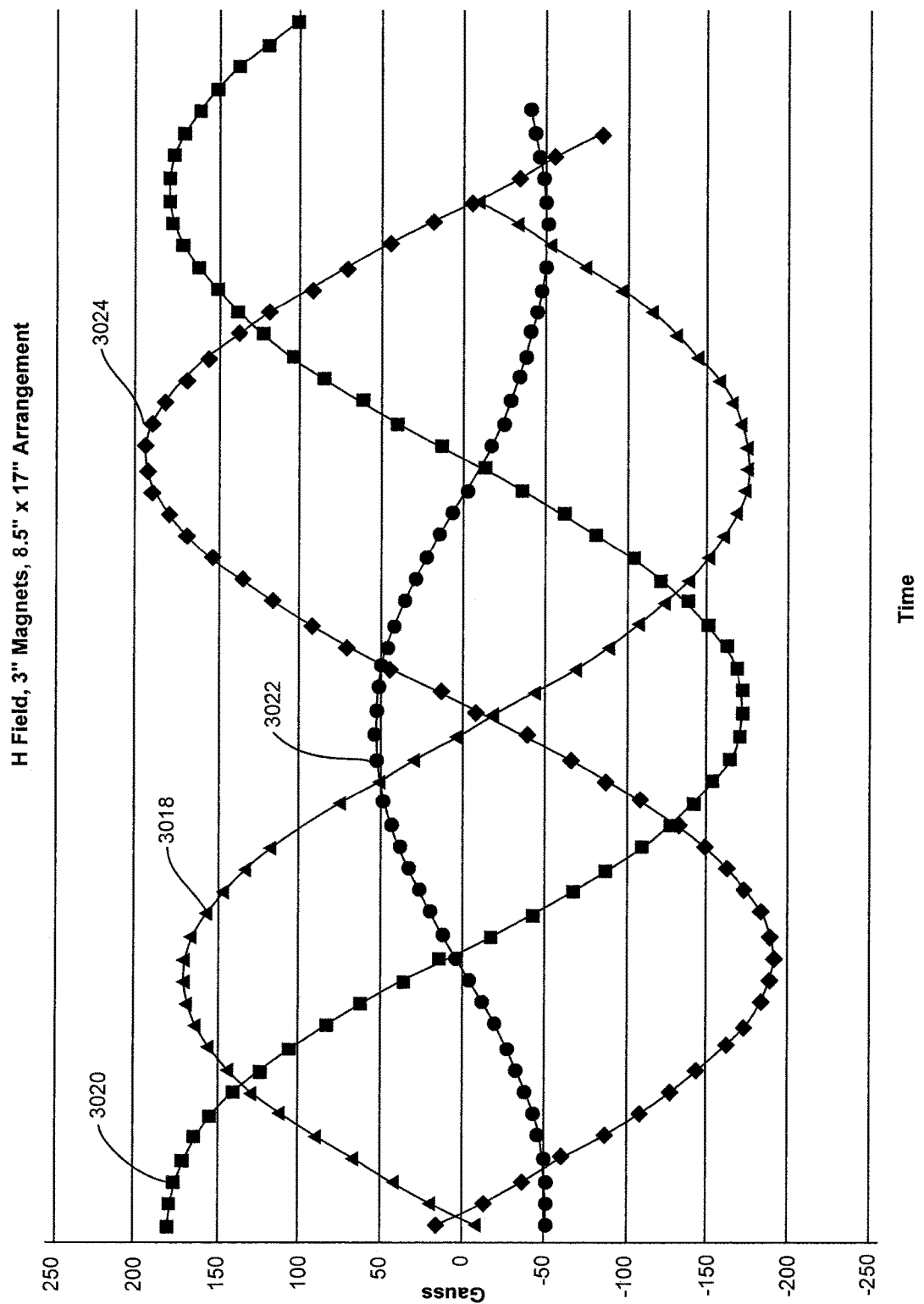

FIGS. 30A and 30B graphically represent example magnetic field measurements as the magnets 110 of the external magnetic adjustment device 102 are rotated according to certain embodiments. FIG. 30A represents data corresponding to aligning 3 inch magnets 110 in a square arrangement that is approximately 8.5 inches×8.5 inches. A first graph 3010 (with data points represented by triangles) corresponds to a Halbach arrangement (see FIGS. 29A and 29B) with a gauss meter aligned at 0° with respect to the horizontal direction. A second graph 3012 (with data points represented by squares) corresponds to the Halbach arrangement (see FIGS. 29A and 29B) with the gauss meter aligned at 45° with respect to the horizontal direction. A third graph 3014 (with data points represented by circles) corresponds to an aligned arrangement (see FIGS. 29C and 29D) with the gauss meter aligned at 0° with respect to the horizontal direction. A fourth graph 3016 (with data points represented by diamonds) corresponds to the aligned arrangement (see FIGS. 29C and 29D) with the gauss meter aligned at 45° with respect to the horizontal direction. As shown in FIG. 30A, the Halbach arrangement provides stronger magnetic fields in the central region of the magnet array, as compared to that of the aligned arrangement.

FIG. 30B represents data corresponding to aligning 3 inch magnets 110 in a rectangular arrangement tats approximately 8.5 inches×17 inches. A first graph 3018 (with data points represented by triangles) corresponds to a Halbach arrangement (see FIGS. 29A and 29B) with a gauss meter aligned at 0° with respect to the horizontal direction. A second graph 3020 (with data points represented by squares) corresponds to the Halbach arrangement (see FIGS. 29A and 29B) with the gauss meter aligned at 90° with respect to the horizontal direction. A third graph 3022 (with data points represented by circles) corresponds to an aligned arrangement (see FIGS. 29C and 29D) with the gauss meter aligned at 0° with respect to the horizontal direction. A fourth graph 3024 (with data points represented by diamonds) corresponds to the aligned arrangement (see FIGS. 29C and 29D) with the gauss meter aligned at 90° with respect to the horizontal direction. As shown in FIG. 30B, the differences between the third graph 3022 and the fourth graph 3024 illustrate that the aligned arrangement does not produce a consistent magnetic field in the central region of the magnet array as the magnets 110 are rotated.

Figure 31:
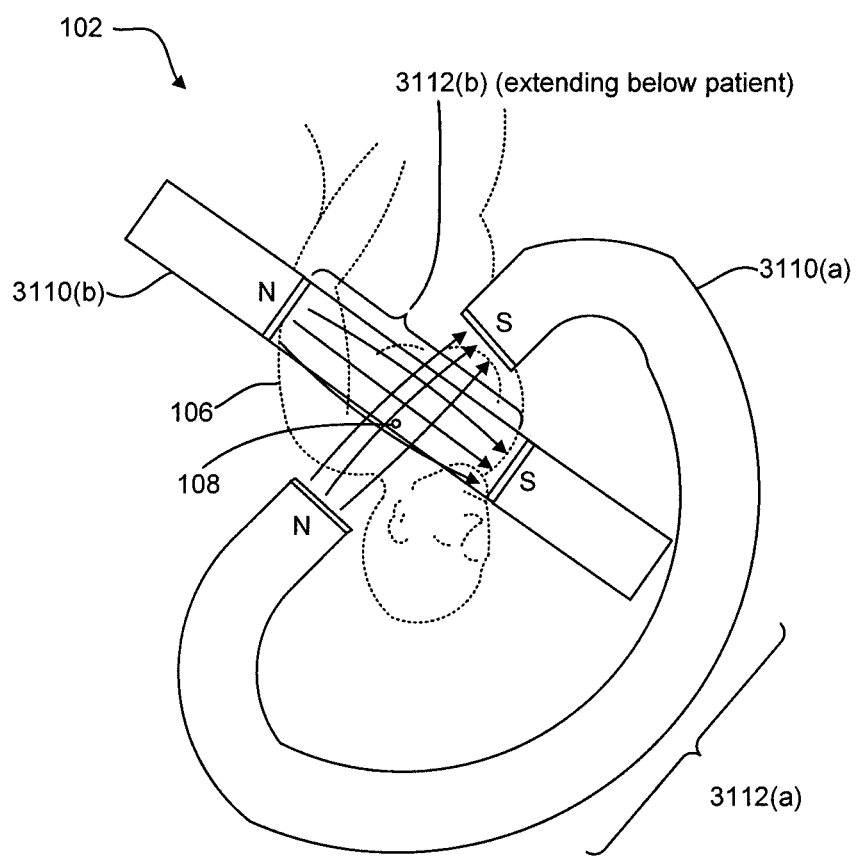
FIG. 31 is a schematic diagram of an external magnetic adjustment device that includes two electromagnets according to one embodiment.

FIG. 31 is a schematic diagram of an external magnetic adjustment device 102 that includes two electromagnets 3110(a), 3110(b) according to one embodiment. Using electromagnets 3110(a), 3110(b) allows the magnetic field generated by the external magnetic adjustment device 102 to be turned off when not in use. Further, in certain embodiments, the electromagnets 3110(a), 3110(b) are driven to provide a constant absolute value for the total magnetic field (as discussed below) as the direction of the total magnetic field is rotated at a selected frequency. In addition, or in other embodiments, the electromagnets 3110(a), 3110(b) may be electronically driven so as to selectively adjust the magnitude of the total magnetic field.

As shown in FIG. 31, the electromagnets 3110(a), 3110(b) according to one embodiment are C-shaped. The C-shape reduces or eliminates the magnitude of the magnetic field outside an area where a patient 106 is being treated. As illustrated by the magnetic field lines in FIG. 31, the magnetic field generated by each electromagnet 3110(a), 3110(b) is fairly well maintained between the opposite ends (e.g., a north "N" end and south "S" end) of the respective electromagnet 3110(a), 3110(b). Although not shown, each electromagnet 3110(a), 311(b) may include, for example, a ferromagnetic core (such as iron) wrapped with an electrically conductive wire. In certain embodiments, the gap between the ends of each C-shaped electromagnet 3110(a), 3110(b) is adjustable. For example, the respective backbones 3112(a), 3112(b) may each include a pivot or slide point.

A first electromagnet 3110(a) is positioned in a horizontal plane and a second electromagnet 3110(b) is positioned in a vertical plane. For example, the "backbone" of the first electromagnet 3110(a) may be in the horizontal plane with a patient table (not shown) and the "backbone" 3112 of the second electromagnet 3112 may pass beneath the patient table. All four magnet ends (two for each magnet 3110(a), 3110(b)) are positioned in the horizontal plane. A patient 106 may be placed on the table in an approximately 30° right-decubitus (right side downward) supine position on the table. In this position, the axis of the magnet 108 in the annuloplasty ring 100 (not shown in FIG. 31) is approximately vertical, and the combined magnetic field is approximately centered around the patient's heart.

Figure 32:
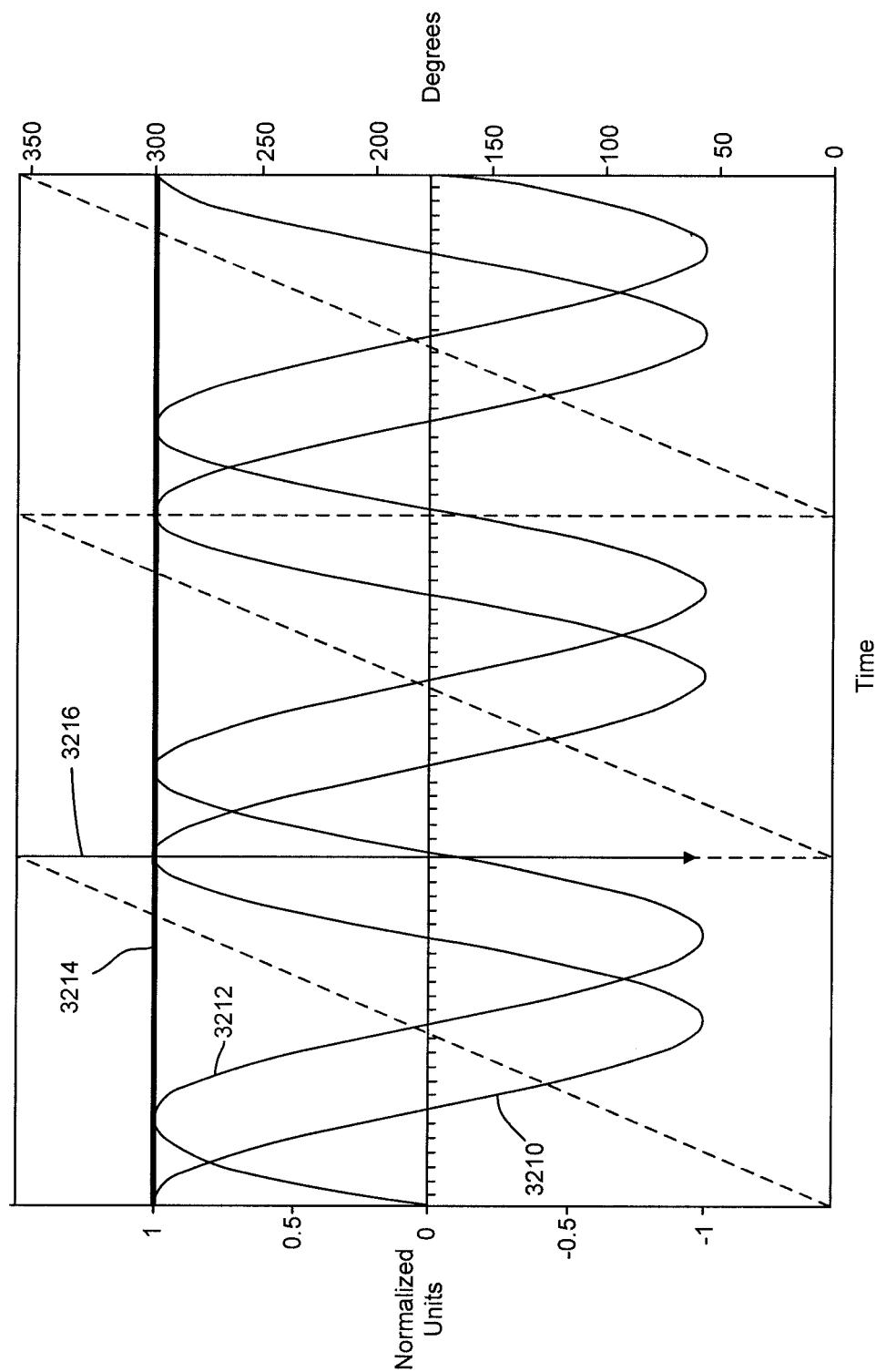
FIG. 32 graphically illustrates various parameters of the magnetic fields generated by the external magnetic adjustment device shown in FIG. 31 according to one embodiment.

FIG. 32 graphically illustrates various parameters of the magnetic fields generated by the external magnetic adjustment device 102 shown in FIG. 31 according to one embodiment. A first graph 3210 illustrates an X-direction component (e.g., that contributed by the magnet 3110(a)) of the combined magnetic field in arbitrary (normalized) units. A second graph 3212 illustrates a Y-direction component (e.g., that contributed by the magnet 3110(b)) of the combined magnetic field in arbitrary (normalized) units. As shown, the first graph 3210 and the second graph 3212 are 90° out of phase from one another. By driving the X and Y-directions of the magnetic fields in this manner, the absolute value of the total field strength of the magnetic field is constant, as illustrated by a third graph 3214. A fourth graph 3216 (shown as a dashed line) illustrates the direction of the total field in degrees. As time progresses, the direction of the total field cycles between 0° and 360° to turn the magnet 108 in the annuloplasty ring 100 implanted within the patient 106.

Example Magnetic Brake Embodiment

Figure 33A:
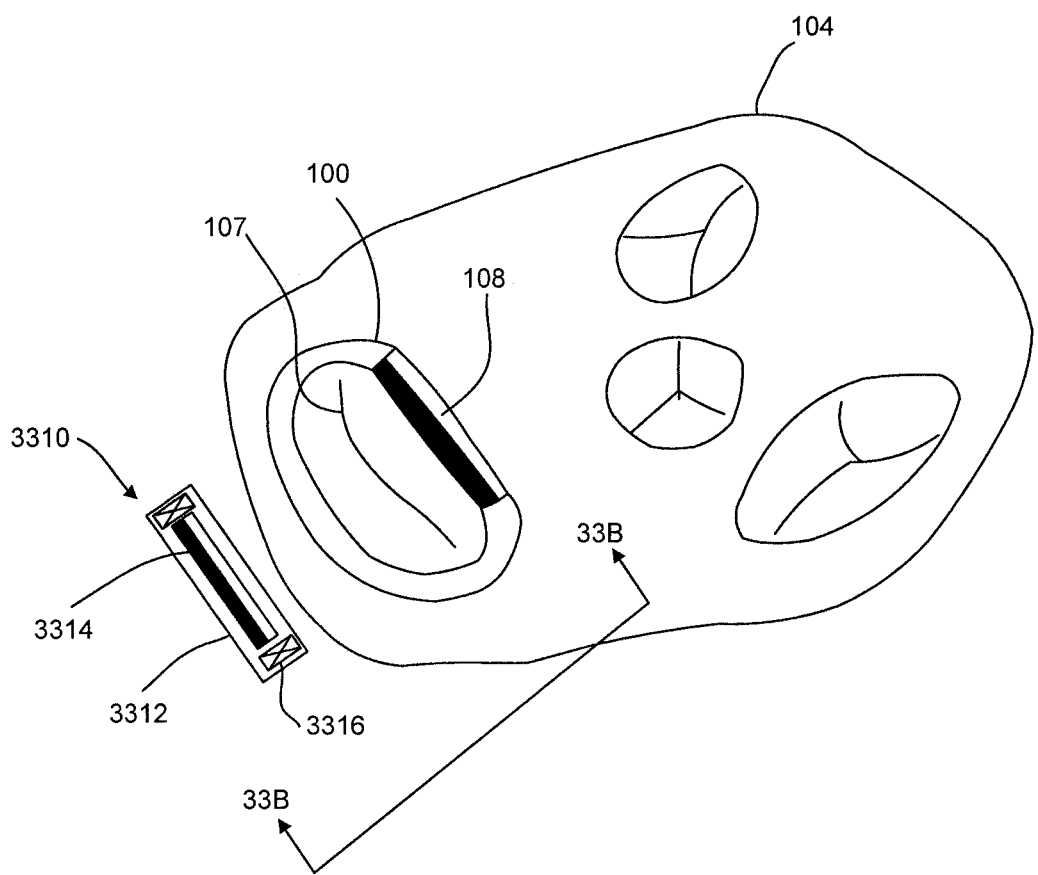
FIG. 33A is a schematic diagram of a superior section view of a heart rating an annuloplasty ring implanted in the heart and a magnetic brake assembly implanted outside of the heart according to one embodiment.

In certain embodiments, vibrations from a patient's beating heart may cause undesirable rotation of the magnet 108 and inadvertent adjustment of the annuloplasty ring 100. Thus, in one embodiment, a magnetic brake is implanted within a patient in an area outside of the patient's heart. For example, FIG. 33A is a schematic diagram of a superior section view of a heart 104 illustrating an annuloplasty ring 100 implanted in the heart 104 and a magnetic brake assembly 3310 implanted outside of the heart 104 according to one embodiment. The annuloplasty ring 100 is attached to or near the mitral valve 107 annulus.

Figure 33B:
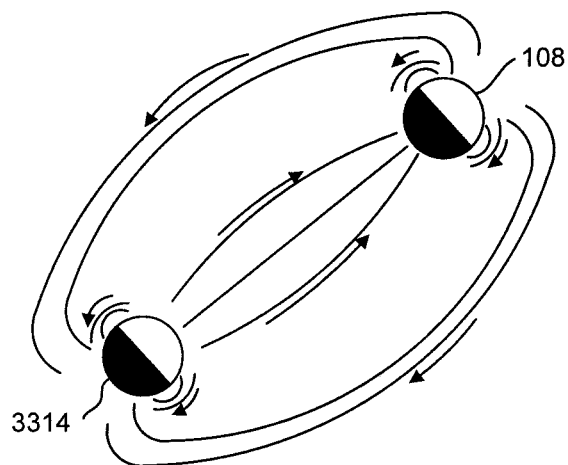
FIG. 33B is a schematic diagram illustrating an end view of a brake magnet and an internal magnet in the annuloplasty ring shown in FIG. 33A according to one embodiment.

The magnetic brake assembly 3310 includes a housing 3312 and a brake magnet 3316 coupled to bearings 3316 in the housing such that the brake magnet 3314 may rotate therein. As discussed above with respect to the internal magnet 108 of the annuloplasty ring 100 and the external magnets 110 of the magnetic adjustment device 102 (shown, e.g., in FIG. 1B, FIG. 3, FIG. 4, FIG. 6, and FIG. 28), the brake magnet 3314 may include a cylindrical magnet having magnetic poles divided along a plane running the length of the cylinder. As shown in FIG. 33B, which is a schematic diagram illustrating an end view of the brake magnet 3314 and the internal magnet 108 in the annuloplasty ring 100 shown in FIG. 33A, the magnetic field of the brake magnet 3314 interacts with the magnetic field of the internal magnet 108 of the annuloplasty ring 100 to prevent rotation of either magnet 3314, 108. Thus, in the absence of the external magnetic field generated by the external adjustment device 102, the internal magnet 108 and the brake magnet 3314 are in "phase lock." The annuloplasty ring 100 may still be adjusted when desired, however, because the external adjustment device 102 generates a sufficiently large rotating magnetic field to overcome the coupling between the internal magnet 108 and the brake magnet 3314.

Figure 34B:
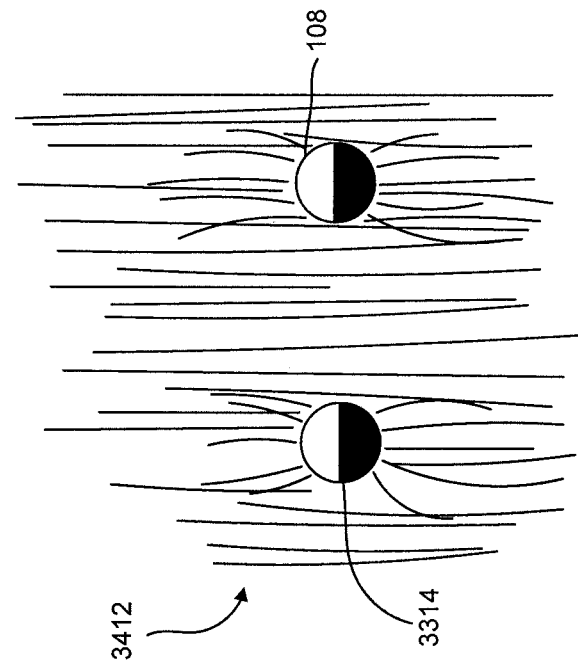
FIGS. 34A and 34B schematically illustrate end views of the brake magnet and the internal magnet of the annuloplasty device according to one embodiment.
Figure 34A:
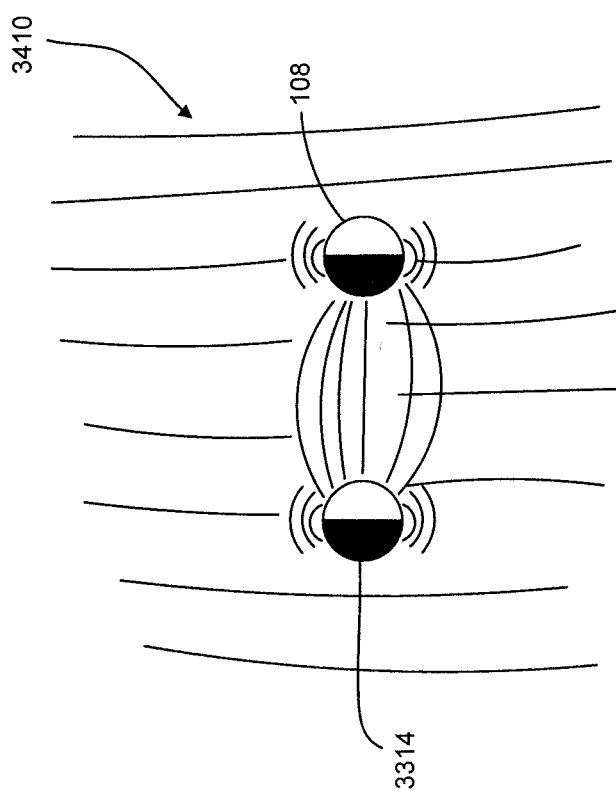

For example, FIGS. 34A and 34B schematically illustrate end views of the brake magnet 3314 and the interne magnet 108 of the annuloplasty device 100 according to one embodiment. In the illustrated examples, a first magnetic pole (e.g., north) is represented by a white semicircle and a second magnetic pole (e.g., south) is represented by a black semicircle. In FIG. 34A, field lines 3410 corresponding to an external magnetic field are represented as having a lower density than field lines 3412 shown in FIG. 34B. Thus, in the example of FIG. 34A the external magnetic field is relatively weak such that the magnetic poles of the magnets 3314, 108 may overcome the magnetic field to align with each other. In the example of FIG. 34A, however, the external adjustment device 102 may be activated to produce a relatively stronger external magnetic field that overcomes the attraction between the magnets 3314, 108. Accordingly, both magnets 3314, 108 align their respective poles with the strong external magnetic field. In other words, both the internal magnet 108 of the annuloplasty ring 100 and the brake magnet 3314 are rotated during selective adjustment of the annuloplasty ring's size.

It will be understood by those having skill in the art that many changes may be made to the details of the above-described embodiments without departing from the underlying principles of the invention. The scope of the present invention should, therefore, be determined only by the following claims.

What is claimed is:

1. A system for changing the dimension of a portion of a subject, the system comprising:
    an adjustable implant configured for implantation within a patient comprising:
      a tubular body member;
      an internal magnet disposed within the tubular body member, the internal magnet configured to rotate in response to a rotating external magnetic field originating external to the subject; and
      an adjustable member operatively coupled to the internal magnet, wherein the internal magnet is configured to rotate in response to the moving magnetic field and change a dimension of the adjustable implant as the internal magnet rotates;
      wherein the tubular body member and the adjustable member substantially form an annulus and are configured to be placed around at least the portion of the subject;
    and
    a magnetic brake positioned in proximity to the internal magnet, the magnetic brake being configured to prevent the internal magnet from rotating in absence of the moving magnetic field and the magnetic brake is configured to allow the internal magnet to rotate in the presence of the moving magnetic field.

2. The system of claim 1, wherein the adjustable member comprises one or more adjustable members.

3. The system of claim 1, wherein the internal magnet comprises a cylindrical magnet.

4. The system of claim 3, wherein the magnetic brake is configured for implantation within the subject.

5. The system of claim 1, wherein the adjustable implant further comprises a magnet housing attached to the internal magnet, the magnet housing rotating with the rotation of the internal magnet, the magnet housing coupling the internal magnet to the one or more adjustable members.

6. The system of claim 1, wherein the adjustable member comprises a wire.

7. The system of claim 6, wherein the wire comprises nitinol.

8. The system of claim 1, wherein the adjustable implant further comprises:
    a first lead screw coupled to a first end of the internal magnet by a first drive cable, wherein rotation of the internal magnet rotates the first drive cable which communicates said rotation to the first lead screw; and
    a drive nut coupled to the one or more adjustable members, wherein threads of the drive nut engage threads of the first lead screw, and wherein rotation of the first lead screw advances the first lead screw through the drive nut to pull or push the one or more adjustable members changing a dimension of the annulus.

9. The system of claim 8, wherein the adjustable implant further comprises:
    a first fixed arm coupled to a first end of the tubular body member; and
    a second fixed arm coupled to a second end of the tubular body member;
    wherein the adjustable member comprises a first swivel arm hinged to the first fixed arm at a first pivot point, and wherein rotation of the first lead screw results in the first swivel arm rotating around the first pivot point.

10. The system of claim 9, wherein the adjustable member further comprises a second swivel arm having a first end hinged to the second fixed arm at a second pivot point, and the second swivel arm having a second end hinged to the first drive nut at a third pivot point, wherein rotation of the first lead screw results in the second swivel arm rotating around the second pivot point and the drive nut rotating around the third pivot point.

11. The system of claim 9, wherein the adjustable member further comprises:
    a second swivel arm having a first end hinged to the second fixed arm at a second pivot point;
    a second lead screw; and
    a second drive cable to couple a second end of the internal magnet to the second lead screw;
    wherein rotation of the internal magnet results in rotation of the second lead screw;
    wherein the drive nut includes a first set of threads to engage the threads of the first lead screw and a second set of threads to engage the threads of the second lead screw; and
    wherein rotation of the second lead screw results in the second swivel arm rotating around the second pivot point.

12. The system of claim 1, wherein the internal magnet includes a hollow opening therein for coupling the internal magnet to the adjustable member.

13. The system of claim 12, wherein at least a portion of the hollow opening is threaded, and wherein the system further comprises a lead screw interfacing with the threads of the hollow opening to draw the lead screw into or out of the hollow opening as the internal magnet rotates.

14. The system of claim 13, wherein the lead screw comprises a flexible wire comprising threads cut or formed in a first end of the flexible wire, wherein the first end of the flexible wire is coupled to a first end of the internal magnet.

15. The system of claim 14, wherein the flexible wire further comprises threads cut or formed in a second end of the flexible wire, wherein the second end of the flexible wire is coupled to a second end of the internal magnet.

16. The system of claim 1, wherein the adjustable implant comprises an adjustable annuloplasty ring.

17. A system for treating a heart valve, the system comprising:
    an adjustable annuloplasty ring configured to be attached to or near a cardiac valve annulus, comprising:
      a tubular body member;
      one or more adjustable members, the tubular body member and the one or more adjustable members forming a ring shape;
      an internal magnet within the tubular body member, the internal magnet configured to rotate in response to a rotating external magnetic field;
      a first lead screw coupled to a first end of the internal magnet by a first drive cable, wherein rotation of the internal magnet rotates the first drive cable which communicates said rotation to the first lead screw; and a drive nut coupled to the one or more adjustable members, wherein threads of the drive nut engage threads of the first lead screw, and wherein rotation of the first lead screw advances the first lead screw through the drive nut to pull or push the one or more adjustable members changing a dimension of the ring shape; and a magnetic brake positioned in proximity to the internal magnet, the magnetic brake being configured to prevent the internal magnet from rotating in absence of the rotating external magnetic field and the magnetic brake is configured to allow the internal magnet to rotate in the presence of the rotating external magnetic field.

18. The system of claim 17, wherein the adjustable annuloplasty ring further comprises:

a first fixed arm coupled to a first end of the tubular body member; and a second fixed arm coupled to a second end of the tubular body member; wherein the one or more adjustable members comprise a first swivel arm hinged to the first fixed arm at a first pivot point, and wherein rotation of the first lead screw results in the first swivel arm rotating around the first pivot point.

19. The system of claim 18, wherein the one or more adjustable members further comprise:

a second swivel arm having a first end hinged to the second fixed arm at a second pivot point;

a second lead screw; and a second drive cable to couple a second end of the internal magnet to the second lead screw;

wherein rotation of the internal magnet results in rotation of the second lead screw;

wherein the drive nut includes a first set of threads to engage the threads of the first lead screw and a second set of threads to engage the threads of the second lead screw; and wherein rotation of the second lead screw results in the second swivel arm rotating around the second pivot point.

* * * * *